US005239062A

United States Patent [19]

Blattler et al.

[11] Patent Number: 5,239,062

[45] Date of Patent: Aug. 24, 1993

[54] BLOCKED LECTINS, METHODS AND AFFINITY SUPPORT FOR MAKING SAME USING AFFINITY LIGANDS, AND METHOD OF KILLING SELECTED CELL POPULATIONS HAVING REDUCED NONSELECTIVE CYTOTOXICITY

[75] Inventors: Walter A. Blattler, Brookline; John M. Lambert, Cambridge; Victor S. Goldmacher, Newton Center; Ravi V. J. Chari, Brookline; Charles F. Scott, Jr., Boston; Linda J. Kostuba, Jamaica Plain, all of Mass.; Simon E. Moroney, London, England; Albert R. Collinson, Boston, Mass.

[73] Assignee: Dana-Farber Cancer Institute, Inc., Boston, Mass.

[21] Appl. No.: 560,948

[22] Filed: Jul. 31, 1990

Related U.S. Application Data

[63] Continuation-in-part of Ser. No. 406,497, Sep. 13, 1989, abandoned, and a continuation-in-part of Ser. No. 150,358, Jan. 29, 1988, abandoned, said Ser. No. 406,497, is a continuation-in-part of Ser. No. 150,358, Jan. 29, 1988, abandoned, which is a continuation-in-part of Ser. No. 841,551, Mar. 20, 1986, abandoned.

[51] Int. Cl.[5] .......... C07K 9/00; C07K 15/14; C07K 15/28; A61K 39/395

[52] U.S. Cl. .......... 530/396; 530/370; 530/402; 530/408; 530/409; 530/391.7; 424/85.91

[58] Field of Search .......... 424/85.91; 514/8; 530/370, 388, 395, 396, 411, 389, 390, 391, 402, 408, 409, 388.22, 391.7

[56] References Cited

U.S. PATENT DOCUMENTS

| | | | |
|---|---|---|---|
| 4,206,094 | 6/1980 | Yen et al. | 523/205 |
| 4,289,747 | 9/1981 | Chu | 424/85.91 |
| 4,320,194 | 3/1982 | Bull | 435/174 |
| 4,340,535 | 7/1982 | Voisin | 424/85.91 |
| 4,359,457 | 11/1982 | Neville, Jr. | 424/85.91 |
| 4,371,515 | 2/1983 | Chu | 424/85.91 |
| 4,440,747 | 4/1984 | Neville, Jr. et al. | 424/85.91 |
| 4,450,154 | 5/1984 | Masuho et al. | 530/395 |
| 4,493,793 | 1/1985 | Chu | 530/303 |
| 4,590,071 | 5/1986 | Scannon et al. | 424/85.91 |
| 4,590,211 | 5/1986 | Voorhees et al. | 514/594 |
| 4,625,014 | 11/1986 | Senter et al. | 530/300 |
| 4,631,190 | 12/1986 | Shen et al. | 424/85.8 |
| 4,647,655 | 3/1987 | Axen et al. | 530/390 |
| 4,664,911 | 5/1987 | Uhr et al. | 424/85.91 |
| 4,689,311 | 8/1987 | Weltman | 530/389 |

FOREIGN PATENT DOCUMENTS

| | | |
|---|---|---|
| 0235116 | 9/1987 | European Pat. Off. . |
| 8705515 | 9/1987 | PCT Int'l Appl. . |

OTHER PUBLICATIONS

A. Huntley Blair et al., *J. of Immunological Methods* 59: 129–143, 1983.
Moroney et al., Biochemistry, 26, 8390–8398 (1987).
Houston, J. Biol. Chem., 258, No. 11, 7208–7212 (Jun. 1983).
Baenziger and Fiete, J. Biol. Chem., 257, 4421–4425 (1982).
Youle et al., Cell, 23, 551–559 (Feb. 1981).
Lee and Lee, Methods in Enzymology, 138, pp. 424–429, (1987).
Lee et al., Biochemistry, 23, 4255–4261 (1984).
Lee et al., J. Biol. Chem., 258, No. 1, 199–202 (Jan. 19, 1983).
Lee and Lee, Biochemistry 25, 6835–6841 (1986).
Townsend et al., Biochemistry 25, 5716–5725 (1986).
Martens, et al., Chemical Abstracts 101131 1984, No. 21690u.
Thorpe et al., Eur. J. Biochem. 140: 63–71 (1984).
Leonard et al., Hybridoma 6(2) pp. 135–149 (1987).
Lambert et al., Biochemistry 30 pp. 3234–3247 (1991).
Kabat et al., "Sequences of Proteins of Immunological Interest" 4th ed., p. xx (1987).

*Primary Examiner*—Robert A. Wax
*Assistant Examiner*—Stephen Walsh
*Attorney, Agent, or Firm*—Sughrue, Mion, Zinn, Macpeak & Seas

[57] ABSTRACT

An activated affinity ligand is described comprising: a ligand having (a) a region with affinity for binding sites (Abstract continued on next page.)

of a lectin; and (b) a reactive group capable of covalently linking the ligand to the lectin to thereby block one or more of the binding sites of the lectin. A blocked lectin is described comprising one or more affinity ligands covalently linked by means of a reactive group present on each of the ligands to a lectin such that one or more binding sites of the lectin is blocked. A cell-binding agent-blocked lectin conjugate is described comprising the above-described blocked lectin and a cell-binding agent covalently linked to: (a) one of the covalently linked affinity ligands; or (b) the lectin. A method of preparing a blocked lectin is described. A method of preparing the cell-binding agent-blocked lectin conjugate is described. An affinity support capable of binding to a lectin to form a blocked lectin is described comprising an activated affinity ligand covalently linked to a solid support. A method of preparing the affinity support capable of binding to a lectin to form a blocked lectin is described. A method of killing selected cell populations having reduced cytotoxicity to non-selected cell populations is described comprising contacting a cell population or tissue suspected of containing cells from said selected cell population with the above-described cell-binding agent-blocked lectin conjugate, wherein the lectin is a cytotoxic lectin. Medicaments and methods of treatment using the above-described cell-binding agent-blocked lectin conjugate also are described.

99 Claims, 24 Drawing Sheets

Affinity Ligand A

Affinity Ligand B

1 Alpha-Lactose

2 Ligand

3

4 Modified Gel Beads

5

6

3

11

12

Modified Gel Beads

1

Alpha-Lactose

13

Ligand

14

15

BLOCKED LECTINS, METHODS AND AFFINITY SUPPORT FOR MAKING SAME USING AFFINITY LIGANDS, AND METHOD OF KILLING SELECTED CELL POPULATIONS HAVING REDUCED NONSELECTIVE CYTOTOXICITY

This application is a continuation-in-part application of copending U.S. Ser. No. 7/406,497, filed Sep. 13, 1989, now abandoned, and of copending U.S. Ser. No. 07/150.358. filed Jan. 29, 1988 now abandoned. U.S. Ser. Serial No. 07/406,497 is a continuation-in-part application of U.S. Ser. No. 07/150.358 filed Jan. 29, 1988 which is a continuation-in-part application of U.S. Ser. No. 06/841.551, filed Mar. 20, 1986. now abandoned.

FIELD OF THE INVENTION

This invention relates to a blocked lectin having greatly diminished binding to cells due to covalent linkage of a novel affinity ligand, which can be provided on a solid support, to the binding site(s) of the lectin, as well as to methods of preparing the blocked lectin. This invention also relates to a cell-binding agent-blocked lectin conjugate capable of delivering the blocked lectin to a selected cell population which involves covalently linking a blocked lectin to a cell-binding agent specific for the selected cell population. This invention further relates to methods of preparing the cell-binding agent-blocked lectin conjugate and to a novel affinity support useful in making the blocked lectin and cell-binding agent-blocked lectin conjugate. This invention even further relates to a method of killing only those cells to which a cell-binding agent binds which employs the above-described conjugate comprising a cytotoxic lectin.

The present invention also relates to immunoconjugates and their application to methods for killing cells. More specifically, the present invention relates to an immunoconjugate comprising an antibody or portion thereof directed to the CD19 antigen, the CD33 antigen or the CD56 antigen and a cytotoxic lectin that has its non-specific cell-surface binding sites blocked by covalently bound ligands (sometimes referred to hereinafter simply as "anti-CD19-blocked lectin", "anti-CD33-blocked lectin" and "anti-CD56-blocked lectin", respectively) and to therapeutic and scientific methods using the immunoconjugate. The present invention also relates to a medicament employing the immunoconjugate.

BACKGROUND OF THE INVENTION

In many medical conditions, it is desirable to kill specifically a selected population of cells, for example, diseased or abnormal cells such as tumor cells, parasitic organisms, certain subgroups of cells of the immune system that may be responsible for autoimmune diseases or responsible for rejection of organ and tissue grafts, or cells infected by microorganisms or viruses (such as HIV, the infectious agent for acquired immunodeficiency syndrome). One strategy that is under current investigation is to use specific antibodies, preferably monoclonal antibodies, or other specific cell-binding molecules, to deliver toxic agents to specific cells in order to kill them selectively. For this approach to be successful, it is desirable that the toxic agent be extremely potent so that delivery of a few molecules to the target cell will be sufficient to kill the cell. However, the toxic agent must exhibit low toxicity towards non-target cells so that only the targeted cells will be killed.

Previously, several monoclonal antibodies have been identified that show specificity for tumor cells and many of these are summarized by Frankel et al., Ann. Rev. Med. 37, 125-142 (1986). Such monoclonal antibodies, and others that may be developed in future work, may be suitable candidates to be used to deliver toxic agents specifically to tumor cells. In principle, monoclonal antibodies can be made that can bind specifically to any particular antigen, including such antigens as may be concentrated on, or found exclusively on, a particular population of cells that it would be desirable to kill, and these antibodies can be linked to toxic agents in order to deliver the toxic agents to the specific cell population.

There are several known cytotoxic lectins such as ricin, abrin, modeccin, volkensin, viscumin and Shigella toxin which kill eucaryotic cells very efficiently. These cytotoxic lectins contain two different types of subunits. One type of subunit, designated the A-chain, exhibits cytotoxic activity by catalytic inactivation of ribosomes, while the other type of subunit, designated the B-chain, is a lectin portion with a recognition capacity, see "The Lectins: Properties, Functions and Applications in Biology and Medicine" (Liener et al., eds.) Academic Press, N.Y. (1986). Since molecules or receptors to which lectins will bind are ubiquitous on cell surfaces, the cytotoxic lectins are non-discriminating, and hence non-selective in their cytotoxicity. This characteristic greatly limits their utility for killing selected diseased, infected or abnormal cells such as tumor cells.

A high resolution X-ray structure for one of these cytotoxic lectins, ricin, has been published by Rutenber et al., *Nature,* 326, 624-626 (1987) and Montfort et al., *J. Biol. Chem.* 262, 5398-5403 (1987). These works show that the ricin B-chain has two galactose-binding sites that are well separated. Previously, cytotoxic lectins have been cleaved into their two types of subunits and the A-chains alone linked to monoclonal antibodies to provide toxic conjugates having selective cytotoxic activity. But such conjugated products display significantly reduced toxicity as compared to intact lectins. Vitetta et al., *Science* 219, 644-650 (1983); Vitetta et al., Transplant. 37, 535-538 (1984); Thorpe et al. in "Monoclonal Antibodies '84: Biological and Clinical Applications" (Pincheva et al., eds.) pp. 475-512, Editrice Kurtis s.r.l. (1985); Pastan et al., *Cell* 47, 641-648 (1986) and Frankel et al., *Ann. Rev. Med.* 37, 125-142 (1986) provide summaries of previous work using this approach. The A-chain of a cytotoxic lectin has also been linked to other specific cell-binding proteins, such as epidermal growth factor (Cawley et al., *Cell* 22, 563-570 (1980) and Simpson et al., *Cell* 29, 469-473 (1982)) and transferrin by Raso et al., *J. Exp. Med.* 160, 1234-1240 (1984). for example. These conjugates exhibited specific cytotoxic activity but also displayed significantly reduced toxicity as compared to the whole cytotoxic lectin.

Previously, conjugates have been made by covalently linking a whole cytotoxic lectin to monoclonal antibodies. Whole ricin has been linked to monoclonal antibodies by Youle et al., *Proc. Natl. Acad. Sci.* (USA) 77, 5483-5486 (1980); Neville et al., U.S. Pat. No. 4,539,457 and U.S. Pat. No. 4,440,747; Houston et al., *Canc. Res.* 41, 3913-3917 (1981); Thorpe et al., *Nature* 297, 594-596 (1982); Vallera et al., *Transplant.* 36, 73-80 (1983): Vallera et al., *Science* 222, 512-515 (1983); Quinones et al., *J. Imm.* 132, 678-683 (1984); Leonard et al., *Canc. Res.* 45, 5263-5269 (1985); Marsh et al., *Biochem.* 25, 4461-4467 (1986) and Goldmacher et al., *J. Biol. Chem.* 262 3205-3209 (1987). Whole ricin has also been linked to other cell-binding molecules such as epidermal growth factor by Herschman, *Biochem. Biophys. Res. Commun.* 124, 551-557 (1984) and monophosphopentamannose by Youle et al., *Proc. Natl. Acad. Sci. (USA)* 76, 5559-5562 (1979).

Conjugates made by linking a whole cytotoxic lectin, such as whole ricin in the examples cited above, to a specific cell-binding agent, exhibit the high cytotoxicity of the cytotoxic lectin. However, such conjugates only exhibit selective killing of the cells targeted by the monoclonal antibody or other cell-binding agent when the conjugates are incubated with cells in the continuous presence of high concentrations of a sugar, for example lactose or galactose, that can bind to the binding sites of the cytotoxic lectin. This is because the binding of the sugar to the binding sites of the lectin portion reduces the non-selective binding of the cytotoxic lectin to cell surfaces. The non-selective toxicity of these conjugates in the absence of high concentrations of sugar greatly limits their usefulness for killing selected cells, such as diseased or abnormal cells, in vivo. However, successful experiments have been performed with a human solid tumor in a nude mouse model system, where a ricin conjugate was injected intratumorally in a solution containing lactose and at the same time the animals received intravenous (i.v.) injections of solutions of lactose (Weil-Hillman et al., *Canc. Res.* 45, 1328-1336 (1985) and *Canc. Res.* 47, 579-585 (1987)).

Conjugates with a whole cytotoxic lectin such as whole ricin may be used in vitro in the presence of lactose or galactose to kill specific populations of cells. Filipovich et al., *The Lancet. Mar.* 3, 1984, pp. 469-472 report the clinical use of conjugates of whole ricin linked to monoclonal antibodies that were specific for human T cells for the ex vivo treatment of human bone marrow to prevent graft-versus-host disease.

Vitetta et al., *Proc. Natl. Acad. Sci.* (USA) 80, 6332-6335 (1983) and McIntosh et al., *FEBS Lett.* 164, 17-20 (1983) report the use of ricin B-chain to increase the potency of conjugates of monoclonal antibody linked to ricin A-chain. However, this approach may have limited utility in vivo because there is a chance that whole ricin will form, once the B-chain is mixed with the A-chain, which could then exhibit high toxicity towards non-target cells.

It would be desirable to block permanently the binding sites of cytotoxic lectins in a stable way, and thereby eliminate the ability of the cytotoxic lectins to kill cells without regard to selectivity, while preserving their ability to kill when, and only when, the blocked cytotoxic lectins are linked to a cell-binding molecule or substance which is selective for particular cells or cell populations. Selective killing of particular cells is, therefore, dependent on the cell-binding agent.

In one approach to interfere with the binding of cytotoxic lectins to cells, Sandvig et al., *Eur. J. Biochem.* 84, 323-331 (1978) treated abrin and ricin with various chemical reagents specific for various chemical functions that are found in proteins and glycoproteins, and demonstrated that acetylation of the cytotoxic lectins, primarily at tyrosine residues, with the reagent N-acetylimidazole, resulted in a 94% reduction in cell-binding activity of abrin and an 88% reduction in cell-binding activity of ricin together with a 94% reduction in toxicity of both lectins. Acetylation of tyrosine residues in wheat germ agglutinin and in lentil lectin, with concomitant loss of agglutination activity, has been, reported by Rice et al., *Biochem.* 14, 4093-4099 (1975) and Vancurova et al., *Biochim. Biophys. Acta* 453, 301-310 (1976), respectively. Acetylated ricin has been used by Leonard et al., *Canc. Res.* 45, 5263-5269 (1985) to form a conjugate with an anti-T cell monoclonal antibody. This preparation of acetylated ricin showed a 10-fold reduction in non-selective toxicity as compared to ricin. This toxicity was reduced further by 10-fold to 100-fold in the presence of 0.1M lactose suggesting that the binding ability of the ricin was, at best, only partially eliminated by acetylation. Vitetta. *J. Imm.* 136, 1880-1887 (1986) described the use of oxidation to alter the ricin B-chain so that its ability to bind as a lectin was greatly reduced. However, the oxidized B-chain of ricin was drastically altered by the oxidizing agent such that it could no longer associate with the ricin A-chain and therefore no whole ricin could form.

Another approach that has been taken with the goal to eliminate the binding of lectins to cell surfaces, has been to physically or sterically hinder their binding ability by covalent linkage of a large molecule to the cytotoxic lectins. Thorpe et al., *Eur. J. Biochem.* 140, 63-71 (1984) described conjugating a monoclonal antibody to intact ricin, then fractionating the product by affinity chromatography to isolate in 20% yield a fraction in which the monoclonal antibody by chance blocked the oligosaccharide-binding sites of the ricin thereby diminishing the capacity of the conjugate to bind non-specifically to cells.

Alternative approaches to reduce the non-selective cytotoxicity of cytotoxic lectins have been to attempt to interfere with binding site(s) of the lectin in more specific ways. In these approaches, molecules that can focus the chemical modification of lectins to the binding sites of the lectins have been used. Such molecules can be modified sugars or compounds containing carbohydrate that can react chemically with lectins at the binding site(s) of the lectins, thus blocking the binding site(s) of the lectin. In one approach, concanavalin A was treated with a photoactivatable arylazido derivative of mannose which binds specifically to the concanavalin A binding sites, followed by exposure to ultraviolet light to form a covalent bond between the concanavalin A and the sugar derivative, as described by Beppu et al., *J. Biochem.* 78, 1013-1019 (1975). The product retained binding activity at two of its four binding sites and displayed reduced haemagglutinating activity. Similar results were recorded by Fraser et al., *Proc. Natl. Acad. Sci. (USA)* 73, 790-794 (1976) using succinylated concanavalin A. and by Thomas, Meth. Enz. 46, 362-414 (1977) in an analogous procedure. A similar procedure has also been employed using ricin and a photoactivatable derivative of galactose as described by Houston. *J. Biol. Chem.* 258, 7208-7212 (1983). The product was found to be 280 times less toxic toward cells than untreated ricin, although the A-chain alone showed full activity in the inhibition of protein synthesis in cell lysates.

Photoactivatable derivatives of complex glycopeptide ligands having a higher affinity for lectins than simple monosaccharides and disaccharides have been described by Baenziger et al., *J. Biol. Chem.* 257, 4421-4425 (1982). The lectins concanavalin A, ricin, and lectin from liver were treated with appropriate photoactivatable derivatives of glycopeptides, and then exposed to light to form a covalent linkage between the lectin and the glycopeptide derivative. However, only 1–2% incorporation of the glycopeptide derivative was achieved in each case. There was, apparently, no attempt to determine the efficacy of the labelling of the lectins through measurements of either cytotoxicity (in the case of ricin) or of haemagglutination (in the case of concanavalin A).

The photoaffinity reagents described by Baenziger et al., *J. Biol. Chem.* 257, 4421–4425 (1982) were made by covalently linking a photoactivatable group to the peptide portion of the glycopeptide ligand. Lee et al., *Biochem.* 25, 6835–6841 (1986) disclose a photolabeling reagent made by covalently linking a photoactivatable group to the C-6 position of a galactosyl residue of a glycopeptide ligand derived from asialofetuin. Lee et al. (cited above) used this photoactivatable affinity labeling reagent to react with the binding site(s) of lectin from liver. However, less than 1% of the photoactivatable glycopeptide ligand could be incorporated into the lectin from liver even under conditions of binding site excess.

It is clear that the B-chain of ricin, abrin, and the like, which is the lectin portion of these cytotoxic lectins, has two functions. One of these functions relates to the binding capability of the molecule as a lectin (Olsnes et al., *Biochem.* 12, 3121–3216 (1973) and Robertus et al., *J. Biol. Chem.* 259, 13953–13956 (1984)), which enables these cytotoxic lectins to bind to lectin receptors on the surface of cells. The second function of the B-chain can be called a transport function, where the B-chain participates in, or facilitates, the process of translocation of the A-chain across a membrane of the cell into the cytoplasm of the cell to which the cytotoxic lectin is bound (Youle et al., *Proc. Natl. Acad. Sci.* (USA) 76, 5559–5562 (1979) and Youle et al., *J. Biol. Chem.* 257, 1598–1601 (1982)). Up until the present invention, there was no convincing evidence that these two functions could be uncoupled. Indeed, there are reports that these two functions of the B-chain, binding as a lectin and transport, cannot be separated from one another (Youle et al., *Cell* 23, 551–559 (1981)). One reason for the lack of convincing evidence that these two functions can be uncoupled is the poor yield and variability in end results in the attempts to block or to interfere with the binding sites of the cytotoxic lectins, either by using the approach of targeting chemical modification to the binding site(s) of the lectins with photoactivatable derivatives of compounds containing carbohydrate and simple sugars, or by interfering with the binding sites by steric hindrance or by non-specific chemical modification of the cytotoxic lectins.

Lee et al., *J. Biol. Chem.* 258, 199–202 (1983) and Lee et al., *Biochem.* 23, 4255–4261 (1984) have shown that a lectin from liver has a much higher affinity for certain branched oligosaccharides than for non-branched oligosaccharides and monosaccharides. Baenziger et al., *J. Biol. Chem.* 254, 789–795 (1979) describe the complete structure of the complex N-glycosidically-linked oligosaccharides of fetuin, the major glycoprotein in fetal calf serum, and the proposed structure for the branched oligosaccharide is represented in FIG. 1(A). This structure was largely confirmed by the evidence reported by Nilsson et al., *J. Biol. Chem.* 254, 4544–4553 (1979) except for one difference at a mannose branch point as represented in FIG. 1(B). More recent analyses by Takasaki et al., *Biochem.* 25, 5709–5715 (1986) and Townsend et al., *Biochem.* 2, 5716–5725 (1986) have shown that the branched oligosaccharides of fetuin are heterogeneous, but that the major species is that represented in FIG. 1(B), consistent with the structure reported by Nilsson et al., *J. Biol. Chem.* 254, 4544–4553 (1979). It was Baenziger et al., *J. Biol. Chem.* 254, 9795–9799 (1979), who determined that asialoglycopeptides, derived by removing sialic acid from glycopeptides derived from fetuin, bound to ricin with a high affinity, having association constants of about $10^7 M^{-1}$.

The work of Rutenber et al., *Nature* 26, 624–626 (1987), Montfort et al., *J. Biol. Chem.* 262, 5398–5403 (1987), Frénoy. *Biochem. J.* 240, 221–226 (1986) and Houston et al., *J. Biol. Chem.* 257, 4147–4151 (1982) suggest that ricin binds galactose at two distinct sites. There is, however, no direct evidence about whether ricin can bind more than one complex N-glycosidically-linked glycopeptide ligand, such as may be derived from asialofetuin (e.g., Baenziger et al., *J. Biol. Chem.* 254, 9795–9799 (1979)). Two galactose-binding sites on a ricin molecule may bind to two different galactose moieties of a single complex glycopeptide ligand, thus accounting for the high affinity of the association between ricin and such glycopeptide ligands.

The variability in end results using prior art blocking agents for the binding sites of lectins is eliminated by the present invention which provides effective and reproducible reduction of the non-selective action of lectins without excessive reduction of their cytotoxic or other desired properties when they are linked to a cell-binding agent.

The CD19 antigen, originally designated as the B4 antigen, is a 95 kd glycoprotein, which is B cell lineage-restricted within the hematopoietic system. B4 was defined originally by a monoclonal antibody clone 89B (=anti-B4; Nadler et al., *J. Imm.* 131, 244–250 (1983)) and the anti-B4 antibody has been accepted by the WHO in Geneva as a standard to define human B lymphocytes. Other laboratories have subsequently produced monoclonal antibodies against the B4 antigen and the antibodies and the antigens recognized thereby have been grouped into a cluster called CD19, ("Leukocyte Typing II, Human B Lymphocytes" (Reinherz et al., eds.) Vol. 2. Chaps. 12 and 13, pp. 155–175. Springer-Verlag (1986)) with anti-B4 being the prototype for this cluster.

The major diseases associated with B cells or pre-B cells where the CD19 antigen is expressed are leukemias and lymphomas. Because the CD19 antigen appears on early pre-B cells and lasts through all stages of B cell ontogeny (Freedman and Nadler, Sem. Onc., 14, 193–212 (1987)) it is expressed in all pre-B cell and B cell neoplasia, i.e. in 95% of all non-T cell ALL (acute lymphocytic leukemia), in 100% of all B-CLL (chronic lymphocytic leukemia of B cell origin), in all types of B cell-derived non-Hodgkin's lymphomas (Burkitt's lymphomas, nodular lymphomas and diffuse lymphomas) in hairy cell leukemias and in Waldenstrom's macroglobulinemia. (Freedman and Nadler. *Sem. Onc.*, 14, 193–212 (1987)). Additionally, although the multiple myeloma cell does not express the CD19 antigen, the clonogenic myeloma cell is CD19-positive, i.e., does express the CD19 antigen.

Although leukemias and lymphomas are very responsive to current conventional and high-dose chemotherapy, the actual cure rate is not very high. (DeVita et al. in "Cancer: Principles and Practice of Oncology" (DeVita et al., eds.) 2nd ed. (1985)). The treatment (radiation and chemotherapy) is limited largely by its non-specific toxic side effects. Accordingly, treatment with a medicament having increased specificity and much higher cytotoxicity, i.e. it kills cells at very low concentrations, is highly desired.

For example, a treatment for some leukemia and lymphoma patients is autologous bone marrow transplantation. In this procedure (Takvorian. T. et al., *New Eng. J. Med.* 316, 1499-1505 (1987)), bone marrow is removed from the patient and treated ex vivo to remove cancerous cells. The purged marrow is reinfused into the patient after his body has been treated by chemotherapy and total body irradiation. The current ex vivo purging of the marrow consists of three cycles of treatment of the mononuclear cells with monoclonal antibodies and baby rabbit complement. This treatment modality is very time consuming and suffers from the problem of variability in complement activity. Every new batch of complement must be screened for activity and non-specific toxicity. Many batches are rejected. A treatment that could achieve the same amount of purging in a single treatment cycle and does not have to be tested from batch to batch, because it shows consistent activity and specificity, would greatly simplify the current treatment.

Human B lymphocytes are also involved in many autoimmune diseases, such as lupus erythematosus, rheumatoid arthritis, myasthenia gravis, multiple sclerosis, immune thrombocytopenia and other autoimmune conditions. In these diseases, autoantibodies are produced by the patient.

Today these diseases are treated with general immunosuppressing drugs such as steroids, cyclophosphamide, rheumatrex (methotrexate) and imuran, which cause side effects such as increased susceptibility to infections. Again, a medicament and treatment that would be more specific and cause less side effects is greatly desired.

A third condition where the elimination of human B cells would be beneficial to patients is in the organ transplant setting. For example, a large number of patients awaiting renal transplantation are sensitized against HLA antigens and produce anti-HLA antibodies, leading to rejection of the transplanted kidney. Currently this reaction is suppressed by the administration of non-specific cytotoxic drugs, such as prednisolone and cyclophosphamide. However, this treatment is not very effective and in addition causes general immunosuppression. A more effective drug and most importantly, a drug that is very specific for the antibody-producing B cells which therefore would not cause all the side effects is much desired.

There are other diseases where increased amounts of immunoglobulin are produced, and which therefore are candidates for medicaments and methods of treatment that deplete B cells. These include conditions like idiopathic thrombocytopenic purpura and hemolytic anemias. It would be desirable to be able to destroy the abnormal B cell clones by treating the patients with an anti-CD19 medicament.

Another desired medicament is one that would block the humoral immune response to foreign proteins. When foreign proteins are administered to humans many develop antibodies against these foreign proteins, which diminishes or abolishes the beneficial effect of the proteins.

Additionally, a reagent that can be used as a research tool in vitro, when it is necessary to have highly purified populations of T cells, of granulocytes (neutrophils, eosinophils and basophils) or of monocytes is much desired. Typically such cell populations will be contaminated with B cells, even if they have been isolated by flow cytometry or panning. Treatment with an anti-CD19-specific cytotoxic reagent would eliminate B cells more thoroughly, would be easier than flow cytometry and could be used on large numbers of cells. Pure cell populations are necessary to study their characteristics such as lymphokine production, reaction and sensitivity to different stimuli and cell-specific expression of certain gene products.

The CD33 antigen, originally designated as the My9 antigen, is a 67 kd cell surface glycoprotein (gp 67) expressed exclusively on the surface of granulocytes, monocytes and their precursor cells in normal human bone marrow. CD33 was defined originally by antibody anti-My9 produced by hybridoma clone 906 (Griffin et al., *Leuk. Res.* 8, 521-534 (1984)). subsequently have made monoclonal antibodies which react with this antigen and the antibodies and the antigens recognized thereby have been grouped together in the cluster designation CD33.

In one study (Griffin et al., *Leuk. Res.* 8, 521-534 (1984)). 84% of 98 cases of AML (acute myelocytic leukemia) tested reacted with anti-My9 monoclonal antibody by immunofluorescence. Only small numbers of other types of leukemic cells reacted with this antibody. The finding of a high percentage of AML cells reactive with this antibody has been confirmed in many other studies, including a multi-institutional national trial conducted by the Cancer and Leukemia Group B (Griffin et al., *Blood* 68, 1232-1241 (1986)) in which it was demonstrated that the antibody reacted with leukemic cells from 71% of 196 cases. The antibody has been shown to be useful in making the diagnosis and confirming the diagnosis of AML, and it is distributed by Coulter Immunology. Hialeah, Fla.

As is the case for many human malignancies, the neoplastic cells in individual cases are heterogeneous. This is particularly true for acute myeloblastic leukemia where only a small fraction of cells is capable of proliferation and the majority of cells are nonproliferating cells which accumulate in the bone marrow and other organs. A current belief is that the proliferative cells act as stem cells for maintaining the leukemic state. A review of AML can be found in Griffin and Lowenberg, *Blood* 68, 1185-1195 (1986). Importantly. in a study of 20 patients with AML, it was shown that the CD33 antigen was expressed on the proliferative. clonogenic AML cells from at least 18 of the 20 patients tested. This study was done using complement lysis. This study suggests that the CD33 antigen is expressed at all stages of differentiation of myeloblastic leukemia cells. Thus, the removal of CD33-positive leukemic cells could eliminate the clonogenic (proliferative) fraction of leukemic cells. CD33 antibodies could form the basis for a rational approach to purging leukemic cells in this disorder.

AML is the most deadly leukemia and no efficacious treatment is available to date (Champlin & Gale. *Blood* 69, 1551 (1987); DeVita et al., supra and "Cancer Facts and Figures" (American Cancer Society) (1988)). Most patients will die within 2-3 years of prognosis of their disease, with 50% of the deaths occurring within 6 months (DeVita et al., supra).

From this data it is clear that the current therapies are not effective for treating AML. The most effective therapy is chemotherapy (Champlain and Gale, *Blood*

69, 1551 (1987) and DeVita et al., supra), which is severely limited by its toxic side effects and by the induction of drug resistance.

The CD56 antigen, originally designated as the N901 antigen or NKH-1 antigen (Knapp et al., *Int. J. Canc.* 44, 190–191 (1989), is a 200,000–220,000 molecular weight glycoprotein, which is considered a pan-natural killer (NK)-associated cell surface marker. The N901 antigen was defined originally by a monoclonal antibody produced by fusing NS-1 myeloma cells with spleen cells of a mouse immunized with human chronic myelogenous leukemic cells (Griffin et al., *J. Imm.* 130, 2947–2951 (1983)). The anti-N901 antibody is available commercially from Coulter Corporation under the name NKH-1. Another antibody has been produced against the N901 antigen and is referred to as anti-NKH1a (Hercend. et. al., *J. Clin. Invest.* 75, 932–943 (1985)).

CD56 is a specific marker for neuroendocrine-type tumors with a concordance rate of expression of nearly 100% (Gazdar, *2nd Ann. Symp. Coulter Imm.*, p. 26, CA (1986)). Neuroendocrine tumors include small cell lung cancer (SCLC), pituitary adenomas, medullary thyroid carcinoma, carcinoids, islet cell tumors, neuroblastomas and pheochromocytomas. Expression of CD56 on SCLC specimens has been documented with 100% concordance on both cell lines derived from SCLC tumors and primary biopsies from SCLC patients (Gazdar, supra: Koros et al., *Proc. Third Intl. Work. Conf. Hum. Leuk. Diff. Antigens* (1986) and Doria et al., Canc. 62, 1939–1945 (1988)). NKH-1 has been grouped into cluster 1 of SCLC determinants by the SCLC antigen workshop (Beverly et al., *Lung Canc.* 4, 15–36 (1988).

There are approximately 155,000 new cases of lung cancer and 142,000 deaths from this disease per year in the United States ("Cancer Facts and Figures" (American Cancer Society) pp. 8–9, (1989)). SCLC will account for 20–25% of these cases. The current treatment for SCLC primarily involves intensive combination chemotherapy and radiotherapy (Jackson and Case, *Sem. Onc.* 13, 63–74 (1986) and Postmus et al. in "High-Dose Chemotherapy for Small Cell Lung Cancer in Lung Cancer: Basic and Clinical Aspects" (Hansen. ed.) (1986)). While over 75% of patients will demonstrate an objective tumor response to therapy, the median survival of all patients from the onset of therapy is only 11 months. Limiting factors in the use of conventional chemotherapy for treatment is the degree of non-specific toxicity and the development of drug-resistant tumor cells.

An additional form of treatment for SCLC involves autologous bone marrow transplantation. In this procedure, bone marrow is removed from the patient and is cryopreserved, and then the body is purged of all cancer cells by large doses of chemotherapy and of total-body irradiation. After the body has been purged, the preserved bone marrow is reinfused. However, in many SCLC patients the bone marrow also contains cancerous cells and has to be treated ex vivo (Mabry et al., *J. Clin. Invest.* 75, 1690–1695 (1985)).

SUMMARY OF THE INVENTION

Accordingly, one object of the present invention is to provide novel methods for blocking the binding sites of lectins that work consistently and in good yield and provide an effective and stable block of the binding of the lectins.

A second object of the present invention is to provide a blocked lectin wherein the binding sites of the lectin are linked covalently to ligands in a permanent and stable way.

A third object of the present invention is to provide a blocked cytotoxic lectin where the ability of the lectin portion of the cytotoxic lectin to bind nonselectively to cells is blocked, thereby providing a new class of substances where the ligand is linked chemically to cytotoxic lectins in such a way that the ligand: (1) blocks the binding function of the lectin portion of the cytotoxic lectin molecule; (2) does not eliminate the transport function of the cytotoxic lectin and (3) does not affect the toxic activity of the cytotoxic lectin once the molecule gains access to the cytoplasm of a cell.

A fourth object of the present invention is to provide methods for preparing conjugates between blocked lectins, especially cytotoxic lectins, and cell-binding agents such as antibodies, especially monoclonal antibodies, lymphokines, hormones, growth factors, nutrient-transport molecules, or any other molecules or substances that bind selectively to the desired cells that the conjugate is to affect.

A fifth object of the present invention is to provide novel conjugates between blocked lectins, especially cytotoxic lectins, and cell-binding agents such as antibodies, especially monoclonal antibodies, lymphokines, hormones, growth factors, nutrient-transport molecules such as transferrin, or any cell-binding molecules or substances, so that the blocked lectins are delivered to particular cells, and only those cells, selected by the cell-binding agent.

A sixth object of the present invention is to provide a treatment for leukemia and lymphomas which is much more effective than the current methods of treatment, in that the method is more specific for the targeted cells and has a much higher cytotoxicity, i.e. the method kills cells at very low concentrations of the drug.

A seventh object is to provide a new method for treatment of autoimmune diseases which is more specific than the current methods and causes fewer side effects than the current methods.

An eighth object of the present invention is to provide a method to suppress production of anti-HLA antibodies in patients undergoing transplant wherein the method uses a more effective drug than is used currently and, most importantly, is very specific for the antibody producing B cells and therefore does not cause all of the side effects caused by the current drugs.

A ninth object of the present invention is to provide a new method for treatment of diseases where increased amounts of immunoglobulins are produced by abnormal B cell clones, wherein the abnormal B cell clones are destroyed.

A tenth object of the present invention is to provide a method for blocking the humoral immune response to foreign proteins administered to patients.

An eleventh object of the present invention is to provide a method of treatment for purging bone marrow of cancerous cells, wherein the method can be performed more easily and more consistently and the medicament does not have to be tested from batch to batch, because it shows consistent activity and specificity.

A twelfth object of the present invention is to provide an improved research tool to obtain populations of T cells, granulocytes or monocytes, which are devoid of B cells.

These and other objects are achieved by the present invention which provides an activated affinity ligand comprising a ligand having:

(a) a region with affinity for binding sites of a lectin; and (b) a reactive group capable of covalently linking the ligand to the lectin to thereby block one or more of the binding sites of the lectin, provided that the reactive group is not a photoactivatable group.

The present invention also provides a blocked lectin comprising one or more affinity ligands covalently linked by means of a reactive group present on each of the ligands to a lectin such that one or more binding sites of the lectin is blocked, provided that the reactive group is not a photoactivatable group.

Also provided by the present invention is a cell-binding agent-blocked lectin conjugate comprising:

(1) the above-described blocked lectin; and (2) a cell-binding agent covalently linked to:

(a) one of the covalently linked affinity ligands on the lectin via a moiety present on the affinity ligand capable of forming a covalent linkage to said cell-binding agent; or (b) the lectin via a moiety present on the lectin capable of forming a covalent linkage to a cell-binding agent.

The present invention further provides a method of preparing the blocked lectin, said method comprising the steps of:

(1) binding at least a region of one or more activated affinity ligands having affinity for the binding sites of the lectin to the lectin: and (2) covalently linking the ligands to the lectin via a reactive group on the ligands to thereby block one or more of the binding sites of the lectin, provided that if the method is conducted with all reactants free in solution, the reactive group is not a photoactivatable group.

This method can be carried out with all of the reactants free in solution.

The method can also be practiced by use of an affinity support such that the ligand reactant is linked covalently to a solid support.

The present invention even further provides a method of preparing the cell-binding agent-blocked lectin conjugate comprising the above steps (1) and (2) for preparing the blocked lectin and an additional step (3) of covalently linking a cell-binding agent to:

(a) one of the affinity ligands; or (b) the lectin.

A method of preparing the above-mentioned affinity support which is capable of binding to a lectin to form a blocked lectin is also provided by the present invention, which method comprises the steps of:

(1) covalently linking one or more affinity ligands to a solid support; and (2) activating the one or more affinity ligands to form a reactive group capable of covalently linking at least one of the one or more ligands to the lectin, provided that the steps (1) and (2) can be performed in either order.

In a preferred embodiment, the covalent linkage to the solid support is cleavable by a reagent not affecting the blocked lectin.

Even further provided by this invention is the above-mentioned affinity support capable of binding to a lectin to form a blocked lectin, comprising an activated affinity ligand covalently linked to a solid support, the activated affinity ligand comprising a ligand having:

(a) a region with affinity for binding sites of a lectin; and (b) a reactive group capable of covalently linking the ligand to the lectin to thereby block one or more of the binding sites of the lectin.

The present invention further provides a method of killing selected cell populations having reduced cytotoxicity to non-selected cell populations, the method comprising contacting a cell population or tissue suspected of containing cells from the selected cell population with a cell-binding agent-blocked cytotoxic lectin conjugate comprising:

(1) a blocked cytotoxic lectin comprising one or more affinity ligands covalently linked by means of a reactive group present on each of the ligands to a lectin such that one or more binding sites of the lectin is blocked, provided that the reactive group is not a photoactivatable group; and (2) a cell-binding agent covalently linked to:

(a) one of the covalently linked affinity ligands on the lectin via a moiety present on the affinity ligand capable of forming a covalent linkage to the cell-binding agent; or (b) the cytotoxic lectin via a moiety present on the lectin capable of forming a covalent linkage to a cell-binding agent.

In preferred embodiments, the lectins are cytotoxic lectins, especially ricin and abrin, and the cell-binding agent is a monoclonal antibody or monoclonal antibody binding site, especially from an anti-CD19 monoclonal antibody, an anti-My9 monoclonal antibody and an anti-N901 monoclonal antibody.

In one preferred embodiment, the present invention provides a medicament for treatment of medical conditions adversely associated with B cells or pre-B cells that express CD19 antigen, said medicament comprising:

(A) a pharmaceutically effective amount of an anti-CD19-blocked cytotoxic lectin immunoconjugate comprising:

(1) a blocked cytotoxic lectin comprising one or more affinity ligands covalently linked by means of a reactive group present on each of the ligands to the cytotoxic lectin such that one or more binding sites of the cytotoxic lectin is blocked, provided that the reactive group is not a photoactivatable group; and (2) an anti-CD19 monoclonal antibody or a CD19-binding site-containing fragment thereof covalently linked to:

(a) one or more of the covalently linked affinity ligands on the cytotoxic lectin via a moiety present on the affinity ligand capable of forming a covalent linkage to the anti-CD19 monoclonal antibody or fragment; or (b) the cytotoxic lectin via a moiety present on the cytotoxic lectin capable of forming a covalent linkage to the anti-CD19 monoclonal antibody or fragment; and (B) a pharmaceutically acceptable carrier. diluent or excipient.

The present invention also provides a method for treatment of medical conditions adversely associated with B cells or pre-B cells that express CD19 antigen, the method comprising treating a subject in need of said treatment with a pharmaceutically effective amount of an anti-CD19-blocked cytotoxic lectin immunoconjugate comprising:

(1) a blocked cytotoxic lectin comprising one or more affinity ligands covalently linked by means of a reactive group present on each of the ligands to the cytotoxic lectin such that one or more binding sites of the cytotoxic lectin is blocked, provided that the reactive group is not a photoactivatable group; and (2) an anti-CD19 monoclonal antibody or a CD19-binding site-containing fragment thereof covalently linked to:

(a) one or more of the covalently linked affinity ligands on the cytotoxic lectin via a moiety present on the affinity ligand that is capable of forming a covalent linkage to the anti-CD19 monoclonal antibody or fragment; or (b) the cytotoxic lectin via a moiety present on the cytotoxic lectin capable of forming a covalent linkage to the anti-CD19 monoclonal antibody or fragment.

Additionally, the present invention provides an in vitro method of purifying cell populations contaminated with B cells or pre-B cells that express CD19 antigen, the method comprising culturing the cell populations in the presence of a cytotoxic amount of an anti-CD19-blocked cytotoxic lectin immunoconjugate comprising:

(1) a blocked cytotoxic lectin comprising one or more affinity ligands covalently linked by means of a reactive group present on each of the ligands to the cytotoxic lectin such that one or more binding sites of the cytotoxic lectin is blocked, provided that the reactive group is not a photoactivatable group: and (2) an anti-CD19 monoclonal antibody or a CD19-binding site-containing fragment thereof covalently linked to:

(a) one or more of the covalently linked affinity ligands on the cytotoxic lectin via a moiety present on the affinity ligand capable of forming a covalent linkage to the anti-CD19 monoclonal antibody or fragment; or (b) the cytotoxic lectin via a moiety present on the cytotoxic lectin capable of forming a covalent linkage to the anti-CD19 monoclonal antibody or fragment.

In a second preferred embodiment, the present invention provides a medicament for treatment of medical conditions adversely associated with cells that express CD33 antigen, said medicament comprising:

(A) a pharmaceutically effective amount of an anti-CD33-blocked cytotoxic lectin immunoconjugate comprising:

(1) a blocked cytotoxic lectin comprising one or more affinity ligands covalently linked by means of a reactive group present on each of the ligands to the cytotoxic lectin such that one or more binding sites of the cytotoxic lectin is blocked, provided that the reactive group is not a photoactivatable group; and (2) an anti-CD33 monoclonal antibody or a CD33-binding site-containing fragment thereof covalently linked to:

(a) one or more of the covalently linked affinity ligands on the cytotoxic lectin via a moiety present on the affinity ligand capable of forming a covalent linkage to the anti-CD33 monoclonal antibody or fragment; or (b) the cytotoxic lectin via a moiety present on the cytotoxic lectin capable of forming a covalent linkage to the anti-CD33 monoclonal antibody or fragment: and (B) a pharmaceutically acceptable carrier, diluent or excipient.

The present invention also provides a method for treatment of medical conditions adversely associated with cells that express CD33 antigen, the method comprising treating a subject in need of said treatment with a pharmaceutically effective amount of an anti-CD33-blocked cytotoxic lectin immunoconjugate comprising:

(1) a blocked cytotoxic lectin comprising one or more affinity ligands covalently linked by means of a reactive group present on each of the ligands to the cytotoxic lectin such that one or more binding sites of the cytotoxic lectin is blocked, provided that the reactive group is not a photoactivatable group: and (2) an anti-CD33 monoclonal antibody or a CD33-binding site-containing fragment thereof covalently linked to:

(a) one or more of the covalently linked affinity ligands on the cytotoxic lectin via a moiety present on the affinity ligand capable of forming a covalent linkage to the anti-CD33 monoclonal antibody or fragment or (b) the cytotoxic lectin via a moiety present on the cytotoxic lectin capable of forming a covalent linkage to the anti-CD33 monoclonal antibody or fragment.

Additionally, the present invention provides an ex vivo method of purifying cell populations contaminated with cells that express CD33 antigen, the method comprising culturing the cell populations in the presence of a cytotoxic amount of an anti-CD33-blocked cytotoxic lectin immunoconjugate comprising:

(1) a blocked cytotoxic lectin comprising one or more affinity ligands covalently linked by means of a reactive group present on each of the ligands to the cycotoxic lectin such that one or more binding sites of the cytotoxic lectin is blocked, provided that the reactive group is not a photoactivatable group: and (2) an anti-CD33 monoclonal antibody or a CD33-binding site-containing fragment thereof covalently linked to:

(a) one or more of the covalently linked affinity ligands on the cytotoxic lectin via a moiety present on the affinity ligand that is capable of forming a covalent linkage to the anti-CD33 monoclonal antibody or fragment: or (b) the cytotoxic lectin via a moiety present on the cytotoxic lectin capable of forming a covalent linkage to the anti-CD33 monoclonal antibody or fragment.

In a third preferred embodiment, the present invention provides a medicament for treatment of medical conditions adversely associated with cells that express CD56 antigen, said medicament comprising:

(A) a pharmaceutically effective amount of an anti-CD56-blocked cytotoxic lectin immunoconjugate comprising:

(1) a blocked cytotoxic lectin comprising one or more affinity ligands covalently linked by means of a reactive group present on each of the ligands to the cytotoxic lectin such that one or more binding sites of the cytotoxic lectin is blocked, provided that the reactive group is not a photoactivatable group: and (2) an anti-CD56 monoclonal antibody or a CD56-binding site-containing fragment thereof covalently linked to:

(a) one or more of the covalently linked affinity ligands on the cytotoxic lectin via a moiety present on the affinity ligand that is capable of forming a covalent linkage to the anti-CD56 monoclonal antibody or fragment: or (b) the cytotoxic lectin via a moiety present on said lectin capable of forming a covalent linkage to the anti-CD56 monoclonal antibody or fragment; and (B) a pharmaceutically acceptable carrier, diluent or excipient.

The present invention also provides a method for treatment of medical conditions adversely associated with cells that express CD56 antigen, the method comprising treating a subject in need of said treatment with a pharmaceutically effective amount of an anti-CD56-blocked cytotoxic lectin immunoconjugate comprising:

(1) a blocked cytotoxic lectin comprising one or more affinity ligands covalently linked by means of a reactive group present on each of the ligands to the cytotoxic lectin such that one or more binding sites of the cytotoxic lectin is blocked, provided that the reactive group is not a photoactivatable group: and (2) an anti-CD56 monoclonal antibody or a CD56-binding site-containing fragment thereof covalently linked to:

(a) one or more of the covalently linked affinity ligands on the cytotoxic lectin via a moiety present on the affinity ligand that is capable of forming a covalent linkage to the anti-CD56 monoclonal antibody or fragment; or (b) the cytotoxic lectin via a moiety present on the cytotoxic lectin capable of forming a covalent linkage to the anti-CD56 monoclonal antibody or fragment.

Additionally, the present invention provides for an ex vivo method of purifying cell populations contaminated with cells that express CD56 antigen, the method comprising culturing the cell populations in the presence of a cytotoxic amount of an anti-CD56-blocked cytotoxic lectin immunoconjugate comprising:

(1) a blocked cytotoxic lectin comprising one or more affinity ligands covalently linked by means of a reactive group present on each of the ligands to the cytotoxic lectin such that one or more binding sites of the cytotoxic lectin is blocked, provided that the reactive group is not a photoactivatable group: and (2) an anti-CD56 monoclonal antibody or a CD56-binding site-containing fragment thereof covalently linked to:

(a) one or more of the covalently linked affinity ligands on the cytotoxic lectin via a moiety present on the affinity ligand capable of forming a covalent linkage to the anti-CD56 monoclonal antibody or fragment: or (b) the cytotoxic lectin via a moiety present on the cytotoxic lectin capable of forming a covalent linkage to the anti-CD56 monoclonal antibody or fragment.

BRIEF DESCRIPTION OF THE DRAWINGS

FIG. 13 shows the inhibition of protein synthesis in a cell-free system from rabbit reticulocytes (Lambert et al. *Biol Chem.* 260, 12035–12041).

FIG. 19(A) shows cytotoxicity for CD19-positive Namalwa cells. FIG. 19(B) shows the cytotoxicity for CD19-negative Molt-4 cells. The experiment is described in Example 30.

FIG. 21 comprises graphs showing the in vivo effects of anti-B4-bR as described in Example 32. The arrows in each panel of FIG. 21 indicate days on which anti-B4-bR was administered.

Figure 1A:
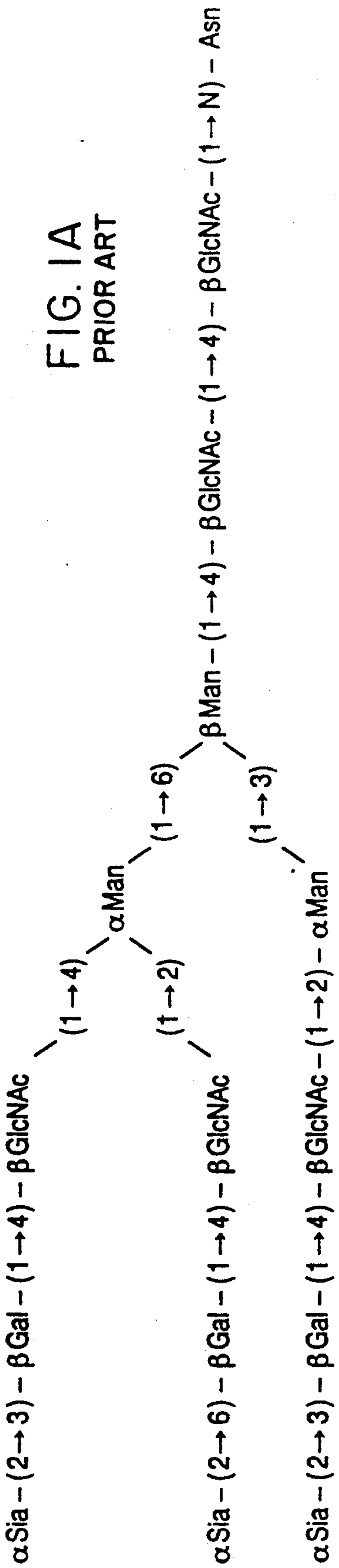
FIG. 1(A) is a representation of the structure of glycopeptides containing N-glycosidically-linked branched oligosaccharides from fetuin as proposed by Baenziger et al., *J. Biol. Chem.* 254, 789–795 (1979).

The symbols used in FIGS. 2 to 6 and 14 have the following definitions:

●=sialic acid

∇=D-galactose

○=N-acetyl-D-glucosamine (2-acetamido-2-deoxy-D-glucose)

■=D-mannose $^+NH_3$▲$CO_2^-$=peptide portion of the glycopeptide, with chemical symbols representing the amino terminus and the carboxyl terminus of the peptide $\nabla^{CHO}$=6-deoxy-6-oxo-D-galactose $\nabla^{CH_2-NH-CH_3}$=N-methyl-6-amino-6-deoxy-D-galactose (MADG)

py=pyridyl

For simplicity, only one possible structure of several similar structures is drawn in the figures after "partial" desialation. Also, only one alternative structure is represented in the ensuing reactions, modifying the terminal galactose residue.

DETAILED DESCRIPTION OF THE INVENTION

This application is a continuation-in-part application of copending applications U.S. Ser. No. 7/406,497, filed Sep. 13, 1989 and U.S. Ser. No. 7/150,358, filed Jan. 29, 1988, U.S. Ser. No. 7/406,497 is a continuation-in-part application of U.S. Ser. No. 07/150.358 which is a continuation-in-part application of U.S. Ser. No. 06/841,551, filed Mar. 20, 1986, now abandoned. The entire disclosure of each of the above-listed U.S. applications is expressly incorporated herein by reference.

Preparation of the Immunoconjugate

As used herein, the following terms and phrases have the definitions given below.

Affinity Binding or Binding—an affinity interaction or affinity association which can result in an affinity complex.

Covalent Linking or Linking—an interaction that results in a covalent bond referred to herein as a "covalent linkage" or simply a "linkage".

Lectin—a term of art. Lectins bind sugars or sugar-like molecules which can be part of many different macromolecules including, but not limited to, oligosaccharides, glycoproteins and glycolipids.

Binding Site of a Lectin—the portion of a lectin delineated by the area that binds sugars or sugar-like molecules.

Blocking—covalently linking an affinity ligand to a lectin in such a way that the ligand is specifically associated with a binding site of the lectin.

Blocked Lectin—a lectin which has one or more affinity ligands covalently linked to the lectin such that each covalently-linked ligand is specifically associated with one of the binding site(s) of the lectin. The phrase includes a lectin that has as few as one to as many as all of its binding sites blocked.

In the case of cytotoxic lectins, blocking leads to a reduction in the cytotoxicity of the cytotoxic lectin, which can be measured by conventional means.

According to the present invention, there is provided a new method of preparing a blocked lectin. The new method is based on the new finding that the chemical reaction leading to a blocked lectin can be carried out by means other than using photoactivation, such as by changes in the pH of the reaction solution and/or changes in the temperature of the reaction solution containing activated ligand and lectin, such that blocked lectin can be formed in much higher yields than if photoactivation is used to covalently link ligands to the binding sites of lectins, and the thus formed blocked lectin retains more of its natural activity and/or exhibits much less binding than if formed by photoactivation.

The method can be carried out with the activated ligand and the lectin free in solution or with the activated ligand covalently linked to a solid support.

Further, use of the activated ligand covalently linked to a solid support is, in itself, novel even when photoactivation is used to covalently link the ligand to the binding sites of the lectin to form the blocked lectin, but use of photoactivation even when the activated ligand is covalently linked to a solid support is much less preferred, due to lower yields of blocked lectin and less efficient blocking of the binding sites of the lectin.

Thus according to the present invention, the method of preparing a blocked lectin comprises the steps of:

(1) binding at least a region of one or more activated affinity ligands having affinity for the binding sites of the lectin to the lectin: and (2) covalently linking the ligands to the lectin via a reactive group on said ligands to thereby block one or more of the binding sites of the lectin, provided that if the method is conducted with all reactants free in solution, the reactive group is not a photoactivatable group.

After the blocked lectin is formed, a further step can be provided of covalently linking the blocked lectin to a monoclonal antibody or other cell-binding agent that can bind selectively to certain cells, for example tumor cells, in order to affect selectively these cells, such as to kill these cells when the lectin is a cytotoxic lectin. The covalent linkage can be to a group on the lectin itself or to a group on one of the ligands covalently linked to the lectin.

In preferred embodiments, after the blocked lectin is formed, the blocked lectin is linked covalently to a monoclonal or polyclonal antibody that binds the CD19, CD33 or CD56 antigen. As described above, the covalent linkage can be to a group on the lectin itself or to a lectin.

The nature of the covalent linkage formed between the affinity ligand and the lectin is important since it must not be cleaved until the cell-binding agent-blocked lectin conjugate is associated with the target cells or otherwise the selectivity of the conjugate comprised of the monoclonal antibody (or other cell-binding agent) and the blocked lectin will be lost. In this latter case, the lectin would again be able to bind to any cell and thus exert high non-specific effects such as toxicity towards all cells.

The blocked lectin comprises one or more affinity ligands covalently linked by means of a reactive group present on each of the ligands to a lectin such that one or more binding sites of the lectin is blocked, provided that the reactive group is not a photoactivatable group. If the lectin has more than one binding site that can be blocked, it is preferred to link more than one affinity ligand to the lectin.

Unexpectedly, it has been found that the blocked lectin of the present invention, although having one or more of its binding sites blocked, still retains its transport function and other functions, such as its full ribosome-inactivating capability. Until this invention, it was believed that the non-selective binding activity could not be uncoupled from the other functions of the lectin without seriously affecting the other functions.

As the lectin for use in the present invention there can be used any lectin having a desired effect on cells.

Especially preferred as the lectin for use in preparing the immunoconjugate, a lectin having cytotoxic activity is used.

Examples of lectins having cytotoxic activity include ricin, abrin, modeccin, volkensin, viscumin or Shigella toxin, or modified derivatives of these lectins that may be produced by genetic manipulation.

Examples of modified derivatives of the lectins include deglycosylated lectins such as produced in bacteria by genetic engineering (see Lamb et al., Eur. *J. Biochem.* 148, 265-270 (1985) and Griffin et al., *Canc. Res.* 47, 4266-4270 (1987)): produced by enzymic methods (Foxwell et al., *Biochim. Biophys. Acta* 840, 193-203 (1985); Skilleter et al., *FEBS Lett.* 196, 344-348 (1986); Foxwell et al., *Biochim. Biophys. Acta* 923, 59-65 (1987) and Wawrzynczak et al., *FEBS Lett.* 207, 213-216 (1986)), or lectins with altered carbohydrates or amino acids such as produced by chemical modification (Thorpe et al., *Eur. J. Biochem.* 146, 197-206 (1985); Simeral et al., *J. Biol. Chem.* 255, 11098-11101 (1980); Blakey et al., *Canc. Drug Del.* 3, 189-196 (1986) and Sandvig et al., *Eur. J. Biochem.* 84, 323-331 (1978)). Modified derivatives of lectins may also be produced by site-directed mutagenesis of lectins produced in bacteria or eucaryotic cells by genetic engineering techniques (see Lamb et al., cited above; Chang et al., *Proc. Natl. Acad. Sci.* (USA) 84, 5640-5644 (1987); WO89/01037 and WO89/04839).

The novel activated affinity ligand according to the present invention comprises a ligand having:

(a) a region with affinity for binding sites of a lectin; and (b) a reactive group capable of covalently linking the ligand to the lectin to thereby block one or more of the binding sites of the lectin, provided that the reactive group is not a photoactivatable group.

As previously mentioned, when the blocked lectin is made using an activated affinity ligand covalently linked to a solid support, the method itself is novel even if the reactive group is photoactivatable, and thus in this case the reactive group can be a photoactivatable group. However, a photoactivatable group is not suitable as a reactive group for the novel activated affinity ligand or the novel blocked lectin of the present invention. Preferably the activated affinity ligand is an oligosaccharide or glycopeptide prepared from fetuin, or other glycoproteins (for examples see Montreuil. *Adv. Carb. Chem. Biochem.* 37, 157-223 (1980)), by enzymic cleavage using endoglycosidases or peptide:N-glycosidases (Hirani et al., *Anal. Biochem.* 162, 485-492 (1987) and Foxwell et al., *Biochim. Biophys. Acta* 840, 193-203 (1985)); by chemical cleavage, for example by treatment with alkali and borohydride (Spiro et al., *J. Biol. Chem.* 249, 5704-5717 (1974) and Nilsson et al., *J. Biol. Chem.* 254, 4545-4553 (1979)) or hydrazinolysis (Takasaki et al., *Biochem.* 25, 5709-5715 (1986) and exhaustive proteolysis of the protein portion of the glycoprotein (Baenziger et al., *J. Biol. Chem.* 254, 789-795 (1979); Lee et al., *Biochem.* 25, 6835-6841 (1986); Townsend et al., *Biochem.* 25, 5716-5725 (1986) and Finne et al., *Meth. Enz.* 83, 269-277 (1982)). Fetuin contains suitable N-glycosidically-linkedoligosaccharidemoieties at three different sites in the fetuin molecule (Spiro. *J. Biol. Chem.* 237, 382-389). Many other glycoproteins that are readily available, for example α-acid glycoprotein, may be used beside s fetuin as the source of affinity ligand (see Lee et al., *J. Biol. Chem.* 258, 199-202 (1983); Fournet et al., *Biochem.* 17, 5206-5214 (1978); and Montreuil. *Adv. Carb. Chem. Biochem.* 37, 157-223 (1980)).

Preferably, the activated affinity ligand contains at least one terminal galactose residue or galactose derivative for affinity binding to the binding sites of a lectin such as the cytotoxic lectin ricin. Terminal galactose derivatives may be generated from the sialic acid-containing oligosaccharides of fetuin and the like by desialation of the glycoprotein, or glycopeptides derived from fetuin, or oligosaccharides derived from fetuin, with dilute acid as described by Warren. *J. Biol. Chem.* 234, 1971-1975 (1959), or by treating these substances with the enzyme neuraminidase (Baenziger et al., *J. Biol. Chem.* 254, 789-795 (1979)), both processes resulting in cleavage of the glycosidic bond between sialic acid and galactose. These methods are well known in the art.

More specifically, the glycopeptide used to make the activated affinity ligand is prepared by digestion of fetuin with pronase (protease of *Streotomyces griseus*), typically using from 1/10th part to 1/100th according to the method of Baenziger et al., *J. Biol. Chem.* 254, 709-795 (1979). Any other proteinases could be used that will result in cleavage of fetuin into small peptides and glycopeptides. For pronase digestion, the pH of the mixture should be buffered near 8 and the mixture should contain millimolar concentrations of $Ca^{2+}$. Digestion is typically for 24 hours at 37° C. Glycopeptides are then purified by gel filtration, for example, using a column of BioGel P-6 and fractions containing glycopeptide are located by assay of hexose (Ashwell, *Meth. Enz.* 8, 85-95 (1966)). If necessary, fractions can be combined for a further cycle of digestion by pronase followed by repurification by gel filtration, and/or a cycle of digestion with carboxypeptidase Y and leucine aminopeptidase or other appropriate proteases followed by repurification by gel filtration using conditions described by Lee et al. (*J. Biol Chem.* 258, 199-202 (1983)) for purifying glycopeptides from glycoproteins. Final purification of glycopeptides is by ion-exchange chromatography, for example, using DEAE-cellulose equilibrated in pyridineacetate buffer at a pH between 4 and 6, eluting the glycopeptide bound to the column with a buffer gradient of increasing ionic strength. These methods are well known in the art (Baenziger et al., *J. Biol. Chem.* 254, 789-795 (1979)). Glycopeptide is recovered from the solvent, such as aqueous pyridine-acetate buffer pH 5, by conventional methods such as rotary evaporation of the solvent.

Synthetic glycopeptide analogues can also be used. These can be prepared by known methods such as, for example, those described by Lee et al, in *J. Biol. Chem.* 258, 199-202 (1983) and in Biochem. 23, 4255-4261 (1984), and in references cited in these papers.

Oligosaccharides, which can also be used to make the activated affinity ligand according to the present invention, can be prepared by enzymatic cleavage of oligosaccharide-containing molecules from glycoproteins using endoglycosidases such as endoglycosidase D. endoglycosidase F, endoglycosidase H and N-endoglycosidase F (also called N-glycanase), using reaction conditions such as described by Hirani et al., *Anal. Biochem.* 162, 485-492 (1987) and references cited therein. The enzymes are commercially available (e.g., Boehringer Mannheim GmbH, Mannheim, FRG; Genzyme, Boston. Mass.). Oligosaccharide moieties that are linked to protein via alkaline borohydride-labile bonds (O-glycosidic linkages) can be cleaved from the glycoprotein by treatment with 0.1N NaOH containing 0.8M $NaBH_4$ at 37° C. for 68 hours according to the method of Spiro et al., *J. Biol. Chem.* 249, 5704-5717 (1974). Oligosaccharide-containing molecules can also be released by hydrazinolysis using standard chemical methods described by Takasaki et al., *Meth. Enz.* 83, 263-268 (1982). Purification of oligosaccharide moieties released by all of these methods is effected by standard biochemical methods such as ion-exchange chromatography and gel filtration (see for example. Hirani et al., *Anal. Biochem.* 162, 485-492 (1987); Spiro et al., *J. Biol. Chem.* 249, 5704-5717 (1974) and Takasaki et al., *Biochem.* 25, 5709-5715 (1986)).

Synthetic oligosaccharide analogues can also be used to make the activated affinity ligand according to the present invention, and these can be prepared by published methods as described, for example, by Lee et al, in *J. Biol. Chem.* 258, 199-202 (1983) and Biochem. 23, 4255-4261 (1984), and in references cited in these papers.

Oligosaccharides from which an affinity ligand can be synthesized may also be derived from other natural sources, such as from glycolipids, from natural oligosaccharide-containing structures found in microorganisms, algae, yeasts, fungi, plants and animals, or may be isolated from the urine of patients having certain diseases (see Montreuil. *Adv. Carb. Chem. Biochem.* 37, 157-223 (1980)).

Four representative methods of synthesizing activated affinity ligand from glycopeptide derived from fetuin are illustrated generally in FIGS. 2, 3, 4, 5 and 6 and are described in detail in Examples 1, 2, 3, 4 and 5.

Once the glycopeptide or oligosaccharide-containing molecule is prepared for use as an affinity ligand, it is necessary to make sure that the affinity ligand contains the terminal carbohydrate moiety appropriate for the particular lectin binding site. For example, an affinity ligand for a cytotoxic lectin such as ricin should have at least one terminal galactose residue, or an affinity ligand for wheat germ agglutinin should have at least one terminal residue of N-acetyl-D-glucosamine. The carbohydrate specificity of these two examples and of many other lectins is summarized in Goldstein et al., *Adv. Carb. Chem. Biochem.* 35, 127-340 (1978); Lis et al., *Ann. Rev. Biochem.* 55, 35-67 (1986) and in Liener et al., supra.

By way of example, if an affinity ligand is being prepared in order to block the binding site of a cytotoxic lectin such as ricin, an affinity ligand having a terminal galactose moiety is synthesized. Glycopeptides or oligosaccharides having terminal sialic acid residues are treated with neuraminidase to expose terminal galactose residues. Neuraminidases can be purified from several different organisms, for example *Clostridium perfrinoens. Vibrio cholerae* and Newcastle Disease Virus (Paulson et al., *J. Biol. Chem.* 257, 12734-12738 (1982)) and many enzymes are available commercially (for example. Boehringer Mannheim GmbH. Mannheim. FRG; British Drug Houses, Poole, England and Sigma Chemical Co., St. Louis, Mo.). Usual conditions for neuraminidase action may vary but generally a buffer between pH 4 and 7, often acetate buffer pH 5.0 (±0.5), containing $CaCl_2$ (in the range of from 1-20 mM) is used (for example, see Baenziger et al., *J. Biol. Chem.* 254, 789-795 (1979) and Hirani et al., *Anal. Biochem.* 162 485-492 (1987)).

One skilled in the art can readily determine analogous procedures for removal of undesired terminal saccharide moieties in order to expose the desired terminal saccharide moieties appropriate for various different lectins.

Compounds containing oligosaccharides lacking galactose may be altered by addition of galactose residues. This may be accomplished by enzymic action, for example using the enzyme UDP-galactose:N-acetyl glucosamine-β-1,4-galactosyltransferase which is capable of transferring galactose from UDP-galactose to N-acetyl-D-glucosamine or to other compounds containing oligosaccharide, including glycopeptides and glycoproteins, having terminal N-acetyl-D-glucosamine (for an example of purification and assay of this enzyme see Schachter et al., *Meth. Enz.* 98, 98-134 (1983)). Addition of galactose residues to compounds containing oligosaccharides such as glycopeptides, may be accomplished also by chemical methods for the synthesis of oligosaccharides as described by Lee, *Carb. Res.* 67, 509–514 (1978); Arnarp et al., *Carb. Res.* 97, 307–313 (1981); Lee et al., *Meth. Enz.* 138, 424–429 (1987); Flowers. *Meth. Enz.* 138, 359–404 (1987); Lee et al., *J. Biol. Chem.* 258, 199–202 (1983) and Lee et al., *Biochem.* 23, 4255–4261 (1984).

One skilled in the art can readily determine analogous procedures for the addition of other carbohydrate moieties appropriate for various different lectins.

Many carbohydrate-containing compounds, such as glycopeptides or oligosaccharides derived from glycoproteins, already have the correct terminal carbohydrate moiety appropriate for the particular lectin. For example, glycopeptides already containing terminal sialic acid residues bind to a lectin from *Limax flavus* (Liener et al, supra) while glycopeptides already containing terminal galactose residues bind to cytotoxic lectins such as ricin. Further, terminal galactose residues may be identified by the ability of such structures to bind to columns of immobilized ricin (Sigma Chemical Co.) or by their ability to be substrates for the action of galactose oxidase using assay procedures described by Amaral et al., *Meth. Enz.* 9, 87–92 (1966).

A very few lectins also bind to non-terminal saccharides in an oligosaccharide moiety, for example, concanavalin A (Goldstein et al., *Biochem. Biophys. Acta* 317, 500–504 (1973)). The presence of the appropriate carbohydrate moiety for specific binding of the affinity ligand to any particular lectin, whether a terminal or internal moiety, can be readily determined by one skilled in the art by using conventional biochemical techniques.

Additional ligands that can be used according to the present invention are described below with reference to preparing the affinity support.

In order to prepare the activated affinity ligand according to the present invention, a reactive group is introduced into the thus-prepared affinity ligand.

The reactive group must be introduced into the affinity ligand at a site on the ligand that will allow the formation of a covalent linkage between the reactive group of the ligand and the lectin.

The nature of the covalent linkage formed between the affinity ligand and the lectin is important since it must not be cleaved until the blocked lectin cell-binding agent conjugate is associated with the target cells or otherwise the selectivity or the conjugate comprised of the cell-binding agent and the blocked lectin will be lost. In this latter case, the lectin would again be able to bind to any cell and thus be able to exert high non-specific effects such as toxicity towards all cells. Further, when the blocked lectin cell-binding agent conjugate is used in vivo the covalent linkage formed between the affinity ligand and the cytotoxic lectin cannot be cleaved readily by any of the conditions likely to be encountered in biological systems. If they were, the improved selectivity would be lost.

Whether a reactive group will be introduced at a site or sites on the ligand that will allow the formation of a covalent linkage between the reactive group of the ligand and the lectin is determined empirically by determining the yield of blocked cytotoxic lectin obtained with any particular affinity ligand containing a reactive group or groups introduced into the ligand in a particular way.

So long as the above requirement is met, it is possible that a reactive group can be introduced int an oligosaccharide ligand by using any suitable cross-linking agent, many of which are known, for example 1,1'-carbonyldiimidazole (Bethel et al., *J. Biol. Chem.* 254, 2572–2574 (1979)); benzoquinone (Brandt et al., *Biochim. Biophys. Acta,* 386, 196–202 (1975)); organic sulfonyl chlorides (Nilsson et al., *Meth. Enz.* 104, 56–69 (1984)); cyanylating agents (Kohn et al., *FEBS Lett.* 154, 209–210 (1983)) and nitrogen mustards such as chlorambucil (Thorpe et al., *Imm. Rev.* 62, 119–158 (1982)). A reactive group may also be introduced into an oligosaccharide by using reagents such as cyanuric chloride (Kay et al., *Nature* 216, 514–515 (1967)) or dichloro-S-triazines such as 2-amino-4,6-dichloro-S-triazine (Kay et al., *Biochim. Biophys. Acta* 198, 276–285 (1970)) and 2,4-dichloro-6-methoxy-S-triazine (Lang et al., *J. Chem. Soc. Perkin* 1, 2189–2194 (1977)). All these cross-linking reagents can be first reacted with the oligosaccharide of the affinity ligand to form an activated affinity ligand, and subsequently the activated affinity ligand can be reacted with a chemical group of the lectin after binding of the activated affinity ligand to the lectin.

An example of a rationale for introducing the cross-linking reagents at specific locations is the identification of specific residues or a specific residue in the lectin that would react readily with a particular cross-linking reagent and that comes close to a specific location of the affinity ligand upon binding of the affinity ligand to the lectin as may be determined by X-ray crystallography. Another example of a reason for introducing the cross-linking reagents at specific locations is less interference with the affinity of the ligand for binding to the cytotoxic lectin as may be determined in binding assays (see Baenziger et al., *J. Biol. Chem.* 254, 9795–9799 (1979) for examples of binding assays).

Cross-linking agents can be introduced into the affinity ligand at specific site(s) by the introduction of amino groups at those site(s) because the cross-linking reagents react much more readily with amino groups than with hydroxyl groups of sugar or sugar derivatives. If a primary or secondary amino group can be introduced into the affinity ligand, preferably at specific locations on the molecule, a covalent bond can be formed between the lectin and the activated affinity ligand by any conventional chemical cross-linking reagent that can react with proteins and amino groups. Many such cross-linking reagents are known and are commercially available. Examples include 1,1'-carbonyldiimidazole (Bethel et al., *J. Biol. Chem.* 254, 2572–2574 (1979)), cyanuric chloride and dichloro-S-triazines (Kay et al., *Nature,* 216, 514–515 (1967) and Kay et al., *Biochim. Biophys. Acta.* 198, 276–285 (1970)), nitrogen mustards such as chlorambucil (Thorpe et al., *Imm. Rev.* 62, 119–158 (1982)), bisimidoesters such as dimethylsuberimidate and bis-N-hydroxysuccinimide esters such as disuccinimidyl tartrate (Ji, *Meth. Enz.* 91, 580–609 (1983)). Also carbodiimides can be used as described by Inman, Meth. Enz. 34, 30–58 (1974) to form cross-links between an amino group on the ligand and a carboxyl group from the cytotoxic lectin (or, alternatively, a carboxyl group on the ligand, as available on a glycopeptide for example and an amino group on the cytotoxic lectin).

Further, cyanuric chloride will react preferentially with a primary or secondary amino group introduced into the affinity ligand, the reaction proceeding to completion in seconds at alkaline pH to form a cyanuric chloride-activated affinity ligand. The activated affinity ligand can then react to form a covalent linkage with the lectin after binding of the activated affinity ligand to the lectin, thus forming a blocked lectin.

Introduction of an amino group into the affinity ligand can be accomplished by reductive amination at the reducing end of an oligosaccharide with ammonium hydroxide or an aliphatic or aromatic primary amine such as methylamine and a reducing agent such as sodium cyanoborohydride. Alternatively, the affinity ligand can be a glycopeptide that already contains an amino group at the N-terminal amino acid of the peptide portion of the ligand.

In another alternative, when the ligand contains a carboxyl group such as found in sialic acid residues of oligosaccharides, or found at the C-terminus of the peptide portion of the affinity ligand when the ligand is a glycopeptide, an amino group can be introduced by reaction of the carboxyl group by, for example, reaction with a large excess of diamine such as ethylene diamine or polyoxyethylene bis(amine) and a carbodiimide, using reaction conditions for carbodiimides as described by Inman, *Meth. Enz.* 34, 30–58 (1974).

Other reactions for modifying carboxyl groups are well known in the art and are summarized by Albertson, *Org. React.* 12, 157–355 (1962) and Klausner and Bodansky, *Synth.* 453–463 (1972). Another alternative is that the compound comprising the ligand can contain amino sugars having free amino groups.

Amino groups can be introduced into oligosaccharide or glycopeptide ligands by reductive amination following the introduction of carbonyl groups into such ligands. Carbonyl groups can be introduced into oligosaccharide or glycopeptide ligands by oxidation with periodate, which will cleave vicinal hydroxyl groups. The extent of oxidation can be measured by the assay of periodate consumption by the method of Knowles, *Biochem. J.* 95, 180–184 (1966), or by measuring the appearance of aldehydo groups using an assay for reducing groups, for example the assay described by Somogyi, *J. Biol. Chem.* 195, 19–23 (1952). Sialic acid residues are particularly sensitive to oxidation by periodate and the introduction of carbonyl groups into oligosaccharides or glycopeptides can be largely limited to oxidation at sialic acid by using mild conditions for example, low reagent concentration, low temperature, short reaction times and the like.

As well as allowing for the introduction of amino groups into oligosaccharide or glycopeptide ligands by reductive amination, carbonyl groups can themselves serve to activate the affinity ligand so that it can react with an amino group of the lectin to form a Schiff's base after the activated ligand has bound to the binding sites of the lectin. In a second step, a stable covalent bond can then be formed between the activated affinity ligand and the lectin by treating the ligand-lectin complex with a reducing agent such as sodium cyanoborohydride or sodium borohydride. If the affinity ligand itself contains an amino group, such as an amino group in the peptide portion of a glycopeptide ligand, this must first be blocked or protected, for example by acylation, so that the aldehyde formed in the affinity ligand can only participate in the desired reaction with an amino group of the lectin.

Figure 1B:
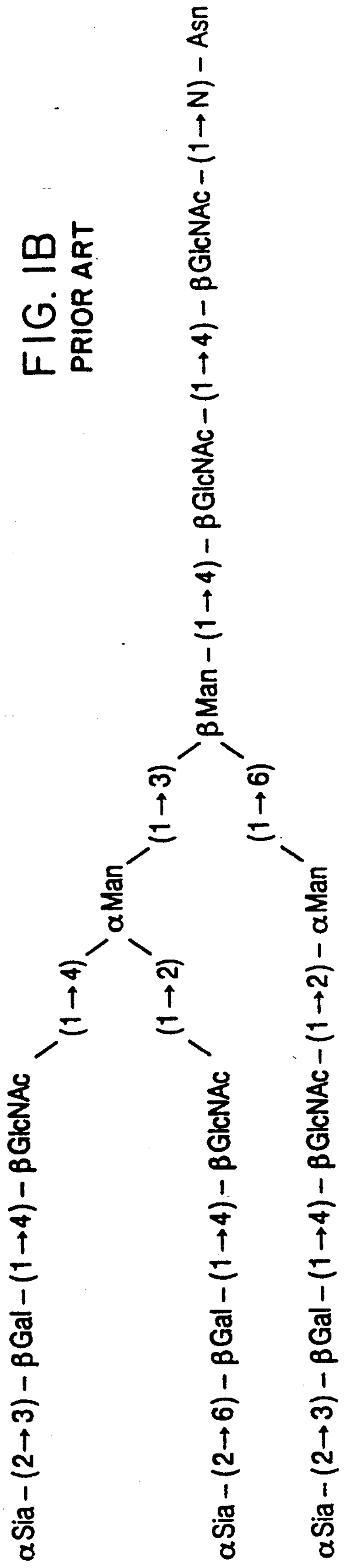
FIG. 1(B) is a representation of the structure of glycopeptides that contain N-glycosidically-linked branched oligosaccharides from fetuin as proposed by Nilsson et al., *J. Biol. Chem.* 254, 4545–4553 (1979). which differs from the structure represented in FIG. 1(A) at one branch point. The structure represented in FIG. 1(B) has been confirmed by more recent analyses done by Takasaki et al., *Biochem.* 25, 5709–5715 (1986) and Townsend et al., *Biochem.* 25, 5716–5725 (1986) as being the predominant form of N-linked oligosaccharide in fetuin. The N-linked glycopeptides made from fetuin are the starting compounds for the reactions leading to the production of the affinity ligands A, B and C of the Examples.

Preferably the terminal galactose residues of the affinity ligand can be oxidized at carbon-6 of the galactose by the enzyme galactose oxidase to create an aldehydo function, preferably only at one or two residues of galactose in a glycopeptide such as shown in FIG. 1(B), since at least one unmodified galactose in the ligand is desirable to maintain the specific binding of the ligand to the lectin. The specificity of the enzyme galactose oxidase ensures the integrity of the ligand, which can still bind to lectins such as ricin as long as the enzyme reaction is limited to preserve at least one non-oxidized galactose in the ligand. A covalent linkage to give a blocked lectin can be formed between the aldehyde introduced into the ligand in this way and the lectin by reduction of a Schiff's base as described above.

Preferably, amino groups can be introduced into the ligand at the aldehydo functions generated by galactose oxidase, by reductive amination with ammonium hydroxide or aliphatic or aromatic primary amines, preferably methylamine, and a reducing agent, preferably sodium cyanoborohydride. The affinity ligand containing one or more amino groups following such treatment can then be covalently linked to the lectin to form a blocked lectin by the procedures described above for linking an amino group-containing ligand to a lectin after specific binding of the ligand to the lectin.

More preferably, the amino group-containing ligand is activated by cyanuric chloride to form an activated affinity ligand, which can then react with the lectin to form a covalent linkage between the ligand and the lectin after specific binding of the activated affinity ligand to the oligosaccharide-binding site of the lectin, thereby giving a blocked lectin.

Examples of reactive groups that can be used to form covalent linkages between the affinity ligand and the cytotoxic lectin such that cleavage outside of cells does not readily occur in biological systems include, for example, groups that form amide bonds such as N-hydroxysuccinimide esters of carboxyl groups, imidate groups, carbonylimidazole groups, chloro-S-triazine groups and 2-substituted quinone groups. All these classes of reactive groups can react with nucleophilic groups such as amino groups found on proteins or glycoproteins to form covalent linkages that are stable in aqueous solutions at the temperatures (37° C.) and pH (pH 6.5 to 8.5) likely to be encountered in biological systems. Many of these examples are described in Goldstein et al, in "Applied Biochemistry and Bioengineering, Immobilized Enzyme Principles" Vol. 1, pp. 1–126 Academic Press. N.Y. (1976).

The level of activation of the affinity ligand can be estimated by three different biochemical assays. In the first, the ultraviolet (UV) spectrum of a sample of the affinity ligand before activation can be compared with a UV spectrum of a sample after activation and purification; activation with cyanuric chloride creates a chromophore with absorption maxima at 242 nm and 280 nm, with molar extinction coefficients of 19,680 at 242 nm and 1405 at 280 nm. The second method determines the level of activation by reacting the activating group introduced into the ligand with a 100-fold to 10,000fold molar excess of radiolabeled amine, for example methylamine of known specific radioactivity (obtained from Amersham International. Amersham. U.K.). The incorporation of radioactivity into the affinity ligand is measured by standard biochemical techniques and is proportional to the level of activation. The third method measures the decrease in the level of amino groups present in the affinity ligand as a consequence of their reaction with the activating reagent. This can be done. for example, using Sanger's reagent according to published methods (*Biochem. J.* 45, 563–574 (1949)).

All of the above methods for introducing reactive groups into the affinity ligand and then linking the affinity ligand to the lectin by forming a covalent linkage and the particular reaction conditions are well known to or can readily be determined by the skilled artisan.

The blocked lectin which can be prepared as described above can be recovered from non-blocked lectin and unreacted activated affinity ligand by numerous methods well known to those skilled in the art.

Suitable examples of recovery methods include the standard biochemical techniques of gel filtration, dialysis or ion-exchange chromatography to remove the activated affinity ligand that did not react with the lectin from the blocked and non-blocked lectin. Then affinity chromatography using columns of immobilized lactose or asialofetuin (or other ligands having terminal galactose residues) is used in order to separate blocked lectin from any non-blocked lectin using procedures such as those described by Thorpe et al., *Eur. J. Biochem.* 140, 63–71 (1984) and Houston. *J. Biol. Chem.* 258, 7208-7212 (1983). Blocked lectin will not be retarded by these columns while non-blocked lectin will be retained by these affinity columns. The best separations between blocked and non-blocked cytotoxic lectins are obtained at 0°–4° C. These procedures are well known and are used in the preparation and purification of lectins from other substances (e.g., Olsnes et al., *Meth. Enz.* 50, 323–330 and 330–335 (1978)).

The number of covalently linked ligands blocking binding sites of the lectin can be determined by hydrolyzing a sample of the preparation of blocked lectin with 3M HCl as described by Fanger and Smyth, *Anal. Biochem.* 34, 494–499 (1970) for analysis of amino sugars. Additional residues of glucosamine or galactosamine derived from covalently bound ligand can then be measured using an amino acid analyser, from which it can be calculated how many ligands are bound to the protein. Alternatively, sugars are analyzed by gas chromatography after first hydrolyzing the blocked lectin and then converting sugars to trimethyl sialyl derivatives for analysis (Spiro. *Meth. Enz.* 8, 3–26 (1966) and Sweeley analysis of the blocked lectin, non-blocked lectin and the affinity ligand itself, and comparison of the values obtained for the content of different sugars in these molecules, allows the calculation of the number of ligands that are blocking binding sites of the lectin.

As mentioned above, the blocked lectin can also be prepared by first making an affinity support capable of binding to a lectin, the affinity support comprising an activated affinity ligand covalently linked to a solid support.

This method is preferred when the affinity between the activated affinity ligand and the lectin is so low that the method performed with all reactants free in solution, i.e, the ligand is not linked to a solid support, gives so low a yield of blocked lectin and/or such high background of non-specifically covalently linked ligand that practical use of the blocked lectin is not reasonably possible.

The solid support employed in this method may be any of the solid supports commonly used for affinity chromatography, such as cross-linked polyacrylamide and derivatives thereof, for example aminoethyl polyacrylamide, derivatized porous glass beads, latex beads, polyvinyl alcohol beads and the like.

The activated ligand employed in the method may be any of those discussed above in addition to those having photoactivatable reactive groups, although photoactivatable reactive groups are less preferred. Preferably the ligand contains a polysaccharide group such as a disaccharide or higher polysaccharide and it preferably contains a terminal galactose derivative.

The covalent linkage between the ligand and the solid support to provide the affinity support can be formed in any conventional manner. Any suitable heterobifunctional cross-linking agents, many of which are known and commercially available, can be used. The cross-linking agent must be cleavable when subjected to selected conditions or reagents to allow separation from the solid support of the blocked lectin after it is formed, although in some cases the blocked lectin may remain linked to the solid support during subsequent use.

Alternatively one or both of the support and the ligand may be modified to include a functional group reactive with the other to form a covalent linkage between the ligand and the solid support, avoiding the need for using a discrete cross-linking agent. The moiety providing cleavability of the ligand from the solid support to which it is covalently linked may take the form of a disulfide group preferentially cleavable by reduction under selected conditions under which the internal disulfide linkage of the lectin itself is not so readily cleaved a thioester group that is cleavable by aminolysis, an azo group that is cleavable by reduction preferentially with dithionite, an orthonitrobenzyl ester or orthonitrobenzyl carbamate cleavable by light of a wavelength of about 360 nm, a vicinal glycol group cleavable by oxidation with periodate and the like.

Similarly the covalent linkage between the ligand and the lectin can be formed by conventional chemical procedures for linking proteins or polypeptides to other compounds or groups, for example, by using appropriate cross-linking agents, as discussed above.

The covalent linkage between the ligand and the solid support as well as the covalent linkage between the ligand and the lectin can each be formed in two or more successive stages, if it is desired. For example, 2-pyridyldithiopropionic acid can be reacted with a solid support such as aminoethylpolyacrylamide to provide a solid support having 2-pyridyldithio groups linked to it. A ligand containing a disaccharide moiety can be prepared by modifying lactose to form N-(2'-mercaptoethyl)lactamine, also known as 1-deoxy-4-O-β-D-galactopyranosyl-1-(2-mercaptoethylamino)-D glucitol, which can be synthesized by conventional methods as exemplified in Example 26. The N-(2'-mercaptoethyl)-lactamine can then replace the 2-mercaptopyridyl groups on the solid support by disulfide interchange, and the residual amino group of the lactamine can then be employed as a functional group to form a covalent linkage with the lectin. This can be accomplished by using a bifunctional cross-linking agent such as 2.4-dichloro-6-methoxytriazine, one chlorine atom of which is very reactive with amino groups at about pH 8, the reaction proceeding to completion in minutes; the remaining chlorine atom being reactive with amino groups much more slowly requiring 24 hours or more at a pH of about 8.5 or more. This cross-linking agent can be first reacted with the residual amino group of the lactamine at about pH 8. and subsequently reacted at higher pH with an amino group of the lectin after it has been properly positioned by specific binding of the lectin to the galactose moiety of the lactamine.

This second cross-linking agent need not be cleavable since it is desired that the ligand remain permanently linked to the lectin to block the binding sites of the latter.

In another embodiment the ligand itself can be chemically modified to include a functional group reactive with lectins to form a covalent linkage therewith.

In the case where the ligand itself is modified to include two functional groups, one capable of forming the covalent linkage with the solid support, another capable of forming a covalent linkage to the lectin, the two functional groups are preferably different in reactivity or conditions of reaction, so that the ligand can be linked to the solid support under one set of conditions, and linked to the lectin under another set of conditions. In this case, the ligand itself may be regarded as a heterobifunctional cross-linking agent containing a disaccharide or polysaccharide moiety capable of binding specifically to the oligosaccharide binding sites of lectins. The two functional groups incorporated in the ligand may be the same as those present in any conventional heterobifunctional cross-linking agent.

Further, in making the affinity support, the ligand can be covalently linked to the support before or after activating the ligand. However, from a chemical standpoint it is preferred to covalently link the ligand to the support before activating the ligand.

In one preferred embodiment, as illustrated in Example 27, the ligand (as well as the resultant blocked lectin) is linked to the solid support through the use of a photocleavable group, such as an orthonitrobenzylcarbamate cleavable by radiation, and there is employed a bifunctional cross-linking reagent to form covalent linkages stable to radiation between the lectin and the ligand of the affinity support.

In another preferred embodiment, as illustrated in Example 28. the ligand is linked to the solid support via an azo group cleavable by preferential reduction with sodium dithionite, while the lectin-ligand covalent linkage is formed by a bifunctional cross-linking agent forming linkages inert to such reduction.

After the ligand has been linked to the solid support to form an affinity support, the lectin has been positioned on the affinity support by specific binding, and then covalently linked to the ligand to form a blocked lectin, the blocked lectin may if desired, be severed from the solid support by cleavage of the ligand-support linkage by conventional procedures.

According to the present invention, the binding sites of the blocked lectin are blocked by covalently linking the activated affinity ligand, which is either free or linked to the solid support, to the lectin and consequently the lectin has a lower affinity for binding to cells and displays reduced non-selective effects, such as cytotoxicity, toward cells in comparison to the corresponding native lectins.

According to the present invention, there is also provided a cell-binding agent-blocked lectin conjugate which renders the blocked lectin selective for the particular cells which it is desired to attack by covalent linkage of the blocked lectin, via the lectin itself or a covalently linked ligand, to a selected cell-binding agent, such as a monoclonal antibody, which has the capacity to bind selectively to particular cells. The result is the cell-binding agent-blocked lectin conjugate of the present invention, which comprises;

(1) a blocked lectin comprising one or more affinity ligands covalently linked by means of a reactive group present on each of the ligands to a lectin such that one or more binding sites of said lectin is blocked, provided that said reactive group is not a photoactivatable group; and (2) a cell-binding agent covalently linked to, (a) one of said covalently linked affinity ligands on the lectin via a moiety present on said affinity ligand capable of forming a covalent linkage to said cell-binding agent; or (b) said lectin via a moiety present on said lectin capable of forming a covalent linkage to a cell-binding agent.

Examples of cell-binding agents that can be used to prepare the conjugate include monoclonal antibodies; lymphokines such as IL-2, IL-3 and interferons (e.g. $\alpha$, $\beta$, $\gamma$); hormones such as insulin. TRH (thyrotropin-releasing hormones) and MSH (melanocyte-stimulating hormone); growth factors and colony-stimulating factors such as TGF, G-CSF and GM-CSF (Burgess. *Imm. Today* 5, 155–158 (1984)); transferrin (O'Keefe et al., *J. Biol. Chem.* 260, 932–937 (1985)) and fragments of antibodies such as Fab, Fab' and $F(ab')_2$ (Parham. J. Imm. 131, 2895–2902 (1983); Spring et al., *J. Imm.* 113, 470–478 (1974) and Nisonoff et al., Arch. Biochem. Biophys. 89, 230–244 (1960)).

Selection of the appropriate cell-binding agent is a matter of choice that depends upon the particular cell population that is to be targeted, but in general monoclonal antibodies are preferred if an appropriate one is available.

For example, the monoclonal antibody J5 is a murine $IgG_{2a}$ antibody that is specific for Common Acute Lymphoblastic Leukemia Antigen (CALLA) (Ritz et al., *Nature*, 283, 583–585 (1980)) and can be used if the target cells express CALLA such as in acute lymphoblastic leukemia. Similarly, the monoclonal antibody anti-B4 is a murine $IgG_1$ that binds to the CD19 antigen on B cells (Nadler et al., *J. Imm.* 131, 244–250 (1983)) and can be used if the target cells are B cells or diseased cells that express CD19 such as in non-Hodgkin's lymphoma or chronic lymphoblastic leukemia. The monoclonal antibody anti-My9 binds to CD33 (Griffin et al., *Leuk. Res.* 8, 521–534 (1984)) and can be used if the target cells are bone marrow cells or monocytes or diseased cells that express CD33 such as in acute myelocytic leukemia. The monoclonal antibody anti-N901 binds to CD56 (Griffin et al., *J. Imm.* 130, 2947–2951 (1983)) and can be used if the target cells are natural killer (NK) cells or diseased cells that express CD56 such as in neuroendocrine tumors including small cell lung cancer.

GM-CSF, which binds to myeloid cells, can be used for targeting blocked cytotoxic lectins to the diseased cells in acute myelogenous leukemia. IL-2. which binds to activated T cells, can be used for prevention of transplant graft rejection, for therapy and prevention of graft-versus-host disease and for treatment of acute T cell leukemia. MSH, which binds to melanocytes, can be used for the treatment of melanoma.

In order to prepare the immunoconjugate which renders the blocked lectin selective for cells that express the CD19. CD33 or CD56 antigen, the blocked lectin is covalently linked to a cell-binding agent that comprises the CD19-binding site, CD33-binding site or CD56-binding site of an anti-CD19. anti-CD33 or anti-CD56 antibody, respectively. The covalent linkage is via the lectin itself or a covalently linked ligand.

The cell-binding agent of the immunoconjugate can be any cell-binding agent as long as it comprises at least one CD19-binding site. CD33-binding site or CD56-binding site of an anti-CD19 anti-CD33 or anti-CD56 antibody, respectively.

These include monoclonal and polyclonal antibodies that react with the CD19. CD33 and CD56 antigens, as well as fragments of these antibodies such as fragments from IgG, Fab$\gamma$, F(ab')$_2\gamma$ and Fab'$\gamma$; and fragments from IgM: Fab$\mu$, F(ab')$_2\mu$ and Fab'$\mu$.

The procedures for the preparation of these fragments are described in numerous textbooks of preparative immunology or immunochemistry. Treatment of IgG with papain leads to Fab$\gamma$ fragments and treatment with pepsin gives F(ab')$_2\gamma$ fragments, which can be reduced with dithiothreitol to Fab'$\gamma$ fragments. Treatment of IgM with papain gives Fab$\mu$ while treatment with trypsin gives F(ab')$_2\mu$ which again can be cleaved reductively to Fab'$\mu$. Methods are well described, e.g., in "Immunochemistry in Practice" (Johnstone and Thorpe, eds.) 2nd ed., pp. 55–73, Oxford (1987).

Fab'-containing immunoconjugates are expected to be especially useful in that a higher degree of tumor localization has been observed for these immunoconjugates (Fulton et al., *Canc. Res.* 48, 2618–2625 and 2626–2631 (1988)).

Also useful are chimeric antibodies, where the variable regions of a human antibody, preferably of the IgG class, have been replaced by an anti-CD19 variable region from an antibody of a different species, for example, from a murine antibody or a rat antibody. The construction of such a chimeric antibody is well described in, for example, Schagan et al., *J. Imm.* 137, 1066–1074 (1986).

More useful are reshaped human antibodies, where the hypervariable regions of a human antibody, preferably of the IgG class, have been replaced by anti-CD19 hypervariable region from an antibody of a different species, for example from a murine antibody or a rat antibody. The construction of such a reshaped antibody is well described in for example, Riechmann et al., *Nature,* 332, 323–327 (1988).

Additionally, so-called single chain antibodies or Fv fragments can be used. In such molecules the light chain and heavy chain variable domains have been linked together by a peptide linker, forming a single chain binding unit of an antibody. This can be done as described, for example, by Bird et al., *Science,* 242, 423–426 (1988) or Houston et al., *Proc. Nat. Acad. Sci.* (USA). 85, 5879–5883 (1988).

As described in the Background of the Invention section, the CD19 antigen is a 95 kd glycoprotein with a pattern of expression that is restricted to cells of B cell lineage within the hematopoietic system and was originally designated as the B4 antigen. The B4 antigen, in turn, was originally defined by monoclonal antibody clone 89B described by Nadler et al., *J. Imm.,* 131, 244–250 (1983). The antibody is a murine $IgG_1$ monoclonal antibody known as "anti-B4" and is commercially available from Coulter Immunolgy, Hialeah, Fla. Other CD19 antibodies are also commercially available such as Leu12 from Becton-Dickinson, Mountain View, Calif. Monoclonal antibody anti-B4 is preferably used as the cell-binding agent comprising a CD19-binding site.

Other laboratories have subsequently produced more monoclonal antibodies against the CD19 antigen, and these antibodies and the antigens recognized thereby, which have been grouped into a cluster called CD19 (Reinherz et al., supra) can also be used as the cell-binding agent. Examples of such antibodies include those designated B8, B28, B43 and L17. Of course, any antibody meeting the criteria used to classify it as belonging to the CD19 is suitable for use in preparing the immunoconjugate. That is, any antibody which binds to the same 95 kd glycoprotein as anti-B4 does, is suitable for use in one preferred embodiment of the present invention.

Also as described in the Background of the Invention section, the CD33 antigen, originally designated as the M9 antigen, is a 67 kd cell surface glycoprotein (gp 67) expressed exclusively on the surface of granulocytes, monocytes and their precursor cells in the normal bone marrow. The My9 antigen, in turn, was originally defined by monoclonal antibody clone 906 described by Griffin et al., *Leuk. Res.* 8, 521–534 (1984). The antibody is known as "anti-My9" and is commercially available from Coulter Immunology.

Subsequently other laboratories have produced more monoclonal antibodies against CD33, and these antibodies and the antigens recognized thereby, which have been grouped into a cluster called CD33 (Reinherz et al., supra) can also be used as the cell-binding agent.

Of course, any antibody meeting the criteria used to classify it as belonging to the CD33 cluster is suitable for use in preparing the immunoconjugate. That is, any antibody which binds to the same 67 kd cell surface glycoprotein as anti-My9 does, is suitable for use in, this preferred embodiment of the present invention.

Further, the Background of the Invention section also pointed out that the CD56 antigen is a 200.000 to 220,000 molecular weight glycoprotein, which is considered a pan-NK-associated cell surface marker and was originally designated as the N901 antigen. The N901 antigen, in turn, was originally defined by a monoclonal antibody produced by fusing NS-1 myeloma cells with spleen cells of a mouse immunized with human chronic myelogenous leukemic cells (Griffin et al., *J. Imm.* 130, 2947–2951 (1983)). The anti-N901 antibody is available commercially from Coulter Corporation. Hialeah, Fla. under the name NKH-1.

Another antibody has also been produced against the N901 antigen and has been designated as anti-NKHla (Hercend et al., *J. Clin. Invest.* 75, 932–943 (1985)). This monoclonal antibody, as well as any others produced against the CD56 antigen and referred to herein collectively as "anti-CD56 monoclonal antibodies", can be used as the cell-binding agent comprising the CD56-binding site. This includes some of the antibodies that have been grouped into cluster 1 of SCLC determinants by the SCLC antigen workshop (Beverly et al., *Lung Canc.* 4, 15–36 (1988)). That is, any antibody which binds to the same 200–220 kD molecular weight glycoprotein as anti-N901 (NKH-1) does, is suitable for use in this preferred embodiment of the present invention. Anti-N901 (NKH1) is preferred.

In the embodiment wherein the cell-binding agent is covalently linked to the lectin itself (rather than to a ligand), the covalent linking of the lectin to the cell-binding agent can be carried out either before or after the lectin is treated with the activated affinity ligand to block the binding site(s) of the lectin, and, if the blocked lectin was formed on an affinity support, either before or after the blocked lectin is cleaved from the solid support, using any of the conventional procedures or cross-linking agents, for example using reagents available from Pierce Chemical Company. Rockford. Ill., or reagents described by Ji, *Meth. Enz.* 91, 580–609 (1983); Blättler et al., *Biochem.* 24, 1517–1524 (1985); in U.S. Pat. Nos. 4,542,225, 4,569,789 and 4,618,492 and in commonly assigned U.S. patent application Ser. No. 908,388, filed Sep. 17, 1986 and references cited therein.

Uses of this approach are illustrated in Examples 8 to 28 herein.

If a non-blocked lectin is covalently linked to the cell-binding agent, the covalently linked non-blocked lectin is blocked after linkage to the cell-binding agent by the same methods described above for preparing the blocked cytotoxic lectin.

In order to covalently link the cell-binding agent to the lectin, the cell-binding agent must be modified by introducing a reactive group, if such is not already present, capable of forming a covalent linkage to the lectin, and, similarly, the blocked or non-blocked lectin must also be modified, if an appropriate moiety capable of forming a covalent linkage to the cell-binding agent is not already present in the lectin.

As mentioned above, various procedures and cross-agents for forming the cell-binding agent-lectin linkage are known in the art.

By way of example, glutaraldehyde can be used to join two different proteins or glycoproteins together by covalent bonds, also bisimidoesters such as dimethylsuberimidate and bifunctional N-hydroxysuccinimide esters such as disuccinimidyl tartrate also can join covalently two proteins or glycoproteins, as reviewed by Ji, *Meth. Enz.* 91, 580–609 (1983). Sulfhydryl groups can be introduced into both molecules by reagents such as 2-iminothiolane (Jue et al., *Biochem.* 17, 5399–5406 (1978)) and methyl 3-mercaptopropionimidate (Perham et al., *J. Mol. Biol.* 62, 415–418 (1971)). Then these can be allowed to oxidize to form disulfide bonds, some of which can link the two different molecules. Sulfhydryl groups can also be cross-linked by bismaleimides (e.g., bismaleimidohexane. manufactured by Pierce Chemical Co.). Disulfide bonds can be formed efficiently between two different molecules if the sulfhydryl group of one of the molecules is activated with a 2-mercaptopyridyl group or a mercaptonitrobenzoate group, as two examples, and then subsequently reacted with the second molecule having a sulfhydryl group.

For example, in order to form conjugates of monoclonal antibody and lectin, activated sulfhydryl groups can be introduced into the monoclonal antibody by reaction with reagents such as N-succinimidyl 3-(2-pyridyldithio)propionate (SPDP), and the monoclonal antibody modified with SPDP can be linked to lectins having a sulfhydryl group using conventional methods such as described for linking monoclonal antibodies to gelonin or other proteins (Lambert et al., *J. Biol. Chem.* 260, 12035–12041 (1985)). In some cases, sulfhydryl groups need to be introduced into the lectin by reaction with. for example. 2-iminothiolane. However, in other cases, a sulfhydryl group is already present in the molecule. For example, the ricin A-chain contains a free sulfhydryl group and can react with molecules such as monoclonal antibodies into which have been introduced pyridyldisulfide groups by reaction with SPDP to form conjugates linked by a disulfide bond (Bjorn et al., *Canc Res.* 45, 1214–1221 (1985)).

In some cases, sulfhydryl groups for cross-linking are already present on both molecules that are to be conjugated, as in the example of joining ricin A-chain to an Fab' fragment of antibody, one of the sulfhydryl groups is activated with dithionitrobenzoate to effect the conjugation (Masuho et al., *J. Biochem.* (Tokyo) 91, 1583–1591 (1982)). Sulfhydryl groups on one protein or glycoprotein can also efficiently react with maleimido groups, or groups containing an α-iodocarbonyl function or an α-bromocarbonyl function, to form thioether linkages. For example, ricin that is modified with 2-iminothiolane to introduce sulfhydryl groups can form conjugates with monoclonal antibodies modified with succinimidyl-4-(N-maleimidomethyl)cyclohexane-3-carboxylate (SMCC) to introduce maleimido groups (Goldmacher et al., *J. Biol. Chem.* 262, 3205–3209 (1987)). In another example, ricin having a maleimido group by reaction with m-maleimidobenzoyl-N-hydroxysuccinimide ester can react with sulfhydryl groups introduced into an antibody by mild reduction of the antibody (Youle et al., *Proc. Natl. Acad. Sci.* (USA) 77, 5483–5486 (1980)) or by reaction with 2-iminothiolane (Marsh et al., *Biochem.* 25, 4461–4467 (1986)).

After forming the conjugate, the conjugate can be recovered by know methods for purifying proteins such as, for example, gel filtration, ion-exchange chromatography and affinity chromatography. Such methods are well known in the art and are summarized in Scopes. "Protein Purification, Principles And Practice" Springer-Verlag. Heidelberg (1982).

In the second embodiment of the cell-binding agent-blocked lectin conjugate of the present invention, the cell-binding agent is linked covalently to one of the activated affinity ligands. In this embodiment, the activated affinity ligand can contain two reactive groups. One reactive group forms a covalent linkage between the affinity ligand and the lectin thus forming a blocked lectin and the second reactive group forms a covalent linkage between the ligand (now covalently bonded to the lectin) and a cell-binding agent such as a monoclonal antibody. For this purpose, any of the reagents described above for cross-linking the ligand to the lectin can also be used for linking the ligand to the cell-binding agent. In addition, any of the reagents described above for cross-linking a lectin to a cell-binding agent can also be used for linking the ligand to the cell-binding agent.

For example, 1,1'-carbonyldiimidazole and cyanuric chloride can react with hydroxyl groups or amino groups that may be present on the affinity ligand, and then react with an amino group of the cell-binding agent. Other chemical functions, such as maleimido groups. sulfhydryl groups, α-iodocarbonyl groups, α-bromocarbonyl groups or disulfide groups can be introduced into the affinity ligand using conventional reagents (for example. Ji, *Meth. Enz.* 91, 580–609 (1983)) for cross-linking reactions with appropriate chemical groups present on a cell-binding agent, or introduced into a cell-binding agent by conventional means (for example Ji, cited above). Also, amino groups or carboxyl groups on the ligand, for example, when a glycopeptide is used as the affinity ligand, can be used to form cross-links to carboxyl groups or amino groups, respectively, of the cell-binding agent using carbodiimide as described by Inman, *Meth. Enz.* 34, 30–58 (1974).

Chemical functions can be introduced into the affinity ligand together with a spacer to increase the distance between the affinity ligand and the cell-binding agent. The spacer can comprise carbon-carbon chains. polypeptide chains, polyether chains, polysaccharide chains and the like. For example. Greenfield et al. (*J. Cell Biochem., Suco* 10B. 52 (1986)) disclose a polypeptide chain of 14 amino acids between a fragment of diphtheria toxin and a cysteine residue which provides a sulfhydryl group that can be cross-linked to a cell-binding agent modified to contain a complimentary reactive group for linking to such a sulfhydryl group (e.g. a maleimido group, a pyridyldisulfide group or an α-iodocarbonyl group using reagents available from Pierce Chemical Co.).

In one preferred embodiment, as illustrated in Examples 2, 3 and 4 herein, a second functional group on the affinity ligand is a pyridyldisulfide group that is introduced at the α-amino group of the peptide portion of a glycopeptide that serves as the affinity ligand with a 3-carbon spacer (Example 2) and a 4-carbon spacer (Examples 3 and 4) between the pyridyldesulfide group and the amino group of the glycopeptide used as the affinity ligand in these examples. Introduction of such a functional group conveniently blocks the α-amino group of the peptide portion of the ligand thus preventing reaction of this amino group with the activating reagent and with reactive functional groups introduced elsewhere in the ligand at more preferred sites for efficient cross-linking of the ligand to the binding sites of the lectin.

A pyridyldisulfide group can be introduced by the methods described in Examples 2, 3 and 4 herein, at other amino groups that may be introduced into a carbohydrate-containing compound that is an affinity ligand using methods described above for introducing amino groups for reaction with the activating or cross-linking reagent.

In one preferred embodiment, the thiopyridyl group is replaced by 2-mercaptoethanol, as illustrated in Example 5. Once the affinity ligand has become covalently linked with the lectin and is blocking the binding site of the lectin, the pyridyldisulfide group or the 2-hydroxyethyldisulfide group on the ligand can be reduced under mild conditions to liberate a sulfhydryl group on the ligand of the blocked lectin. A functional group is introduced into a monoclonal antibody (or other cell-binding agent) that can react with the above mentioned sulfhydryl group to form a covalent linkage in order to enable the cell-binding agent, e.g. comprising the CD19-binding site, to be linked directly to the ligand portion of the blocked lectin. For example, in this case when the functional group on the blocked lectin is a sulfhydryl group, an antibody may be reacted with a reagent such as SMCC to provide a maleimido group on the antibody that can subsequently react with the sulfhydryl group on the blocked lectin to link the blocked lectin to the antibody.

One skilled in the art can readily determine and prepare other suitable bifunctional cross-linking agents capable of reacting with the ligand and with a chemical group of the cell-binding agent, for example, comprising the CD19-binding site.

For example, N-succinimidyliodoacetate can introduce iodoacetyl groups into an antibody that can subsequently react with the above-mentioned sulfhydryl groups on the blocked lectin. Also, pyridyldisulfide groups can be introduced into antibodies by reaction with SPDP and then these groups can react with the above-mentioned sulfhydryl group on the blocked lectin which will result in a cross-link containing a disulfide bond (see Lambert et al., *J. Biol. Chem.* 260, 12035-12041 (1985)). Sulfhydryl groups can be introduced into an antibody by using 2-iminothiolane (Blättler et al., *Biochem.* 24, 1517-1524 (1985)) or by mild reduction (Youle et al., *Proc. Natl. Acad. Sci.* (USA) 77, 5483-5486 (1980)) and, such a group can react with the pyridyldisulfide group of the activated affinity ligand (as in Examples 2, 3 and 4, herein) of the blocked lectin to form a covalent linkage containing a disulfide bond.

In this embodiment of the present invention, it is preferred, but not necessary, that the two functional groups be different in reactivity or use different reaction conditions. In this way, the activated affinity ligand can be linked to the oligosaccharide-binding sites of the lectin under one set of conditions and to the cell-binding agent under another set of conditions.

In one preferred embodiment, illustrated in Example 26, the blocked lectin is linked through the ligand to the solid support via a disulfide group cleavable by reduction. The resulting residual sulfhydryl group left on the ligand is then used as a functional group to form a covalent bond with the antibody. For this purpose any suitable bifunctional cross-linking agent capable of reacting with the sulfhydryl group and also with an amino or other group of the antibody may be employed. Preferably a functional group reactive with the sulfhydryl group to form the covalent linkage is introduced in the antibody to enable it to react directly with the functional group of the blocked lectin. For example, when the functional group on the blocked lectin is a sulfhydryl group, an antibody may be reacted with a reagent such as SMCC to provide a maleimido group on the antibody.

By the above methods, the blocked cytotoxic lectin has a reduced capacity to bind to molecules containing carbohydrate that are found on cell surfaces owing to the covalently linked affinity ligand(s) that blocks the site(s) of the lectin by a covalent linkage. Thus the blocked lectin has reduced capacity to bind to cells and its effect, e.g. high toxicity, on cells has been reduced. Conjugation of the blocked lectin to an antibody (or other cell-binding agent, e.g., one containing the CD19-binding site) that can bind to antigens found on particular populations of cells then provides a new means for the blocked lectin to bind to cells. Binding the blocked lectin to cells via an antibody, e.g. a CD19-binding site, restores the ability of the blocked lectin to exert its effects, e.g. high toxicity in the case of cytotoxic lectins. However, the effect, e.g., high toxicity, is now selective and specific for cells which carry the particular antigen to which the antibody, e.g., the CD19 antibody, will bind.

The improved specificity as well as other benefits and characteristics of the products according to the present invention are demonstrated in Example 29.

The improved specificity as well as other benefits and characteristics of the anti-CD19-blocked lectin immunoconjugates according to the present invention are demonstrated in Examples 30, 31 and 32.

The method of killing selected cells according to the present invention comprises contacting a cell population or tissue suspected of containing cells from the selected cell population with the above-described cell-binding agent-blocked cytotoxic lectin conjugate, wherein the lectin is a cytotoxic lectin.

The method can be practiced ex vivo, in vivo or in vitro.

Examples of ex vivo uses include treatments of autologous bone marrow prior to their transplant into the same patient in order to kill diseased or malignant cells; treatments of bone marrow prior to their transplantation in order to kill competent T cells and prevent graft-versus-host disease (GVHD); treatments of cell cultures in order to kill all cells except for desired variants that do not express the target antigen or to kill variants that express undesired antigen.

For clinical ex vivo use to remove tumor cells or lymphoid cells from bone marrow prior to autologous transplantation in cancer treatment or in treatment of autoimmune disease, or to remove T cells and other lymphoid cells from autologous or allogeneic bone marrow or tissue prior to transplant in order to prevent GVHD or other autoimmune diseases such as systemic lupus. rheumatoid arthritis and multiple sclerosis, treatment can be carried out as follows. Bone marrow is harvested from the patient or other individual and then incubated in medium containing serum to which is added a cell-binding agent-blocked cytotoxic lectin conjugate, concentration range about 10 μM to 1 pM, for about 30 minutes to about 48 hours at about 37° C. The exact conditions of concentration and the time of incubation (=dose) are readily determined by the skilled artisan. After incubation, the bone marrow cells are washed with medium containing serum and returned to the patient by i.v, infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

Examples of medical conditions that can be treated according to the in vivo method to kill selected cell populations include malignancy of any type including, for example, cancer of the lung, breast, colon, prostate, kidney and lymphatic organs; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft-versus-host disease viral infections, such as CMV infection, HIV infection, AIDS etc, and parasite infections, such as giardiasis, amoebiasis, shistosomiasis etc.

For clinical in vivo use, cell-binding agent-blocked cytotoxic lectin conjugates will be supplied as solutions that are tested for sterility and for endotoxin levels. Suitable protocols of conjugate administration are known readily to one of ordinary skill in the art. For example, conjugates are given daily for 5 days either as an i.v, bolus each day for 5 days or as a continuous infusion for 5 days. Bolus doses are given in 50-100 mL of normal saline to which 5-10 mL of human serum albumin has been added. Continuous infusions are given in 250-500 mL of normal saline, to which 25-50 mL of human serum albumin has been added, per 24 hour period. Dosages will be 1-100 μg/kg of body weight per day, i.v. (with a range of 1 ng to 10 mg/kg per day). A second course of treatment may be given to the patient 2-4 weeks later. Specific clinical protocols with regard to route of administration, excipients, diluents, dosages, times etc., can be determined by the skilled artisan as the clinical situation warrants.

One further important aspect of the present invention when used in vivo is that the covalent linkage formed between the affinity ligand and the cytotoxic lectin cannot be readily cleaved by any of the conditions likely to be encountered in biological systems. If they were, the improved selectivity would be lost.

Examples of reactive groups that can be used to form covalent linkages between the affinity ligand and the cytotoxic lectin such that cleavage outside of cells does not readily occur in biological systems include, for example, groups that form amide bonds such as imidate groups. N-hydroxysuccinimide esters of carboxyl groups, carbonylimidazole groups, chloro-S-triazine groups and 2-substituted quinone groups. All those classes of reactive groups can react with nucleophilic groups such as amino groups found on proteins or glycoproteins to form covalent linkages that are stable in aqueous solutions at the temperatures (37° C.) and pH (pH 6.5-8.5) likely to be encountered in biological systems. Many of these examples are described in Goldstein et al, in "Applied Biochemistry and Bioengineering. Immobilized Enzyme Principles" pp. 1-126, Academic Press NY (1976).

The conditions of non-clinical in vitro use are readily determined by the skilled artisan.

In preferred embodiments, the present invention is also directed to methods for treating medical conditions adversely associated with cells that express the CD19, CD33 or CD56 antigens, in vitro or ex vivo methods of purifying cell populations contaminated with cells that express the CD19, CD33 or CD56 antigens, and to medicaments for in vivo, ex vivo, or in vitro treatment of medical conditions adversely associated with cells that express the CD19, CD33 or CD56 antigen.

For the purpose of this invention, the phrase "adversely associated with cells" means those diseases which are caused by cells that express the designated antigen, and, in particular, medical conditions "adversely associated with B cells or pre-B cells" means those diseases which are caused by pre-B or mature B cells as well as those neoplastic diseases which are derived from pre-B and mature B cells.

According to this invention, it has been found that anti-CD19-blocked lectin immunoconjugates, anti-CD33-blocked lectin immunoconjugates and anti-CD56-blocked lectin immunoconjugates are capable of selectively killing cells expressing the CD19, CD33 and CD56 surface antigens, respectively, to which anti-CD19, anti-CD33 and anti-CD56 antibodies, respectively, bind. Therefore. these immunoconjugates are useful in all circumstances where it is beneficial to eliminate cells expressing the CD19, CD33 or CD56 antigens.

According to one preferred embodiment, the present invention further provides a medicament for treatment of medical conditions adversely associated with B cells or pre-B cells that express CD19 antigen, wherein the medicament comprises:

(A) a pharmaceutically effective amount of anti-CD19-blocked lectin immunoconjugate; and (B) a pharmaceutically acceptable carrier, diluent or excipient.

The method for treatment of medical conditions adversely associated with B cells or pre-B cells that express CD19 antigen according to the present invention comprises in vivo or ex vivo treatment of a subject in need of such treatment with a pharmaceutically effective amount of anti-CD19-blocked lectin immunoconjugate.

Examples of medical conditions that can be treated in include leukemias and lymphomas wherein the disease causing cells express the CD19 antigen such as non-T cell acute lymphocyte leukemia, chronic lymphocytic leukemia of B cell origin, B cell-derived non-Hodgkin's lymphoma such as Burkitt's lymphomas, nodular lymphomas diffuse lymphomas, hairy cell leukemia, multiple myeloma and Waldenstrom's macroglobulinemia.

Human B lymphocytes are also involved in many autoimmune diseases, such as lupus erythematosus, rheumatoid arthritis, myasthenia gravis, multiple sclerosis, immune thrombocytopenia and many others. These diseases would also advantageously be treated in vivo with the medicament and by the method of the present invention in order to deplete B lymphocytes.

In vivo treatment with the medicament and by the method of the present invention to eliminate human B cells would also be beneficial to patients undergoing organ transplants.

Other diseases where increased amounts of immunoglobulin are produced and which therefore would benefit from in vivo treatment with the medicament and by the method of the present invention to eliminate human B cells include conditions like idiopathic thrombocytopenic purpura and hemolytic anemias.

Finally, when foreign proteins are administered to humans, many develop antibodies against these foreign proteins which diminishes or abolishes their beneficial effects. For example, it has been shown that humans make anti-murine IgG antibodies and anti-toxin antibodies to immunotoxins. Again, depletion of B cells by in vivo treatment with the medicament and by the method of the present invention is expected to be beneficial.

Examples of medical conditions that can be treated ex vivo with the medicament and by the method of the present invention include cancer, autoimmune diseases such as systemic lupus, rheumatoid arthritis and multiple sclerosis, and pre-transplant states to prevent GVHD upon transplant.

Many other clinical applications of the medicament and method of treating medical conditions adversely associated with B cells or pre-B cells can readily be determined by the skilled artisan simply by assaying for the presence of the CD19 antigen in tissue specimens by methods known in the art or by assaying for production of unwanted antibodies, also by methods known in the art. These clinical conditions can be identified by the presence of CD19-positive pre-B or B cells by techniques including ELISA, flow cytometric analysis. immunohistochemical staining and molecular biological techniques such as in situ hybrdization and PCR.

For clinical in vivo treatment, the anti-CD19-blocked lectin immunoconjugates are supplied as solutions that are tested for sterility and for endotoxin levels.

The immunoconjugate is administered as an infusion of one hour to continuous infusion, which is maintained until the MTD (maximal tolerated dose) is achieved. This can be different in each individual patient and can be monitored by end-organ toxicity, including for example elevation in liver function test results or changes in hematologic parameters.

One specific example of a suitable protocol is to administer the immunoconjugate daily for 5 days either as an i.v, bolus each day for 5 days, or as a continuous infusion for 5 days. Bolus doses are given in 100 mL of normal saline containing 1 mg/mL of human serum albumin through a Hickman central venous line. Continuous infusions are given in 250–500 mL of normal saline, to which 25–50 mL of human serum albumin has been added, per 24 hour period. Dosages range from 10 μg/kg of body weight to 100 μg/kg of body weight per day, i.v. The patient may receive a second course of treatment 2–4 weeks later.

Specific clinical protocols with regard to route of administration, carriers, diluents, excipients, dosages, times, etc., can be determined by the skilled artisan as the clinical situation warrants.

Examples of suitable carriers, diluents and/or excipients include: (1) Dulbecco's phosphate-buffered saline, pH about 7.4, containing about 1–25 mg/mL human serum albumin. (2) 0.9% saline (0.9% (w/v) NaCl), and (3) 5% (w/v) dextrose For clinical ex vivo use to remove tumor cells or lymphoid cells from bone marrow prior to autologous transplantation in cancer treatment or in treatment of autoimmune disease or to remove B cells and other lymphoid cells from autologous bone marrow prior to transplant in order to treat autoimmune diseases such as systemic lupus, rheumatoid arthritis and multiple sclerosis, various treatment plans can be followed. For example, bone marrow is harvested from the patient or other individual and then incubated in medium containing serum to which is added a cell-binding agent-blocked cytotoxic lectin conjugate, in a concentration range of about 10 μM to 1 pM, for about 30 minutes to about 48 hours at about 37° C. The exact conditions of concentration and time of incubation (=dose) are determined readily by the skilled artisan. This treatment may also be done in the presence of enhancer compounds, such as monensin or nigericin. Typical concentrations for these compounds are in the μmolar range. After incubation, the bone marrow cells are washed with medium containing serum and returned to the patient by i.v, infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

Also in a preferred embodiment, the present invention provides an in vitro method of purifying cell populations contaminated with B cells or pre-B cells that express the CD19 antigen. The method comprises culturing the cell populations in the presence of anti-CD19-blocked lectin immunoconjugate and then removing dead B cells or pre-B cells.

The conditions of non-clinical in vitro use are well known to and/or are determined readily by the skilled artisan. (See, for example. Uckun et al., *J. Exp. Med.*, 163, 347–368 (1986); Uckun et al., *J. Imm.*, 134, 3504–3515 (1985) and Ramakrishnan et al., *J. Imm.* 135, 3616–3622 (1985)).

According to another preferred embodiment, the present invention provides a medicament for treatment of medical conditions adversely associated with cells that express the CD33 antigen, wherein the medicament comprises:

(A) a pharmaceutically effective amount of an anti-CD33-blocked lectin immunoconjugate: and (B) a pharmaceutically acceptable carrier, diluent or excipient.

The method for treatment of medical conditions adversely associated with cells that express CD33 antigen according to the present invention comprises in vivo or ex vivo treatment of a subject in need of such treatment with a pharmaceutically effective amount of anti-CD33-blocked lectin immunoconjugate.

Since the CD33 antigen is known to be expressed on some normal myeloid progenitor cells in addition to leukemic cells, it has been important to determine if the antigen is expressed on human pluripotent stem cells. Unfortunately, no direct assay is available for the human pluripotent stem cell. However, it has been shown that the CD33 antigen is not expressed on the cells required for establishment of hematopoiesis in a long term Dexter culture (Greenberger et al, in "Transfusion Medicine" pp. 159-85 (1986)). This type of assay identifies the earliest hematopoietic progenitor cell which can be grown in tissue culture.

Importantly, the antibody has been used along with complement to purge AML cells from human bone marrow in the setting of autologous transplantation for AML. Eight such patients have received anti-My9 and complement-treated autologus bone marrow to rescue hematopoiesis after treatment with total-body irradiation and high-dose chemotherapy. All eight patients have engrafted successfully. These data suggest that the My9 antigen is not expressed on the human pluripotent hematopoietic progenitor cell. Thus the depletion of these cells using an anti-My9-based immunotoxin would be followed by successful reconstitution of all hematopoietic cells from endogenous pluripotent stem cells.

Because of the tissue distribution of the My9 antigen, the anti-My9-blocked lectin immunoconjugate is effective against the following diseases, acute myelocytic (myeloblastic) leukemia (AML) and chronic myelocytic leukemia (CML) in blast crisis. AML may also be called ANLL (acute non-lymphocytic leukemia) and may be subclassified further (see Champlin and Gale. *Blood* 69, 1551-1562 (1987)).

The anti-CD33-blocked lectin immunoconjugate can be used in vivo by intravenous infusion or ex vivo for purging of My9-positive cells from bone marrow.

Other clinical applications of the medicament and method of treating medical conditions adversely associated with cells that express the CD33 antigen can be determined readily by the skilled artisan by assaying for the presence of the CD33 antigen in tissue specimens using methods known in the art or by assaying for production of unwanted antibodies, also using methods known in the art. These clinical conditions can be identified by the presence of CD33-positive cells by the techniques described above for assaying for the presence of CD19-positive cells.

For clinical in vivo treatment, the anti-CD33-blocked lectin immunoconjugates are supplied as solutions that are tested for sterility and for endotoxin levels.

The immunoconjugate is administered as an infusion of one hour to continuous infusion, which is maintained until the MTD is achieved. This can be different in each individual patient and can be monitered by end-organ toxicity as discussed for administering the anti-CD19-blocked lectin immunoconjugate.

Specific examples of suitable protocols and doses for in vivo administration of the anti-CD33-blocked lectin immunoconjugate are the same as those described for in vivo administration of the anti-CD19-blocked lectin immunoconjugate.

Specific clinical protocols with regard to route of administration, carriers, diluents, excipients, dosages, time, etc., can be determined by the skilled artisan.

Examples of suitable carriers, diluents and/or excipients include those mentioned for in vivo administration of the anti-CD19-blocked lectin immunoconjugate.

For clinical ex vivo use to purge My9-positive cells from bone marrow, the method of Ritz (*Clin. Haemat.* 12, 813-832 (1983)) can be used, except that the antibody complement treatment would be replaced by an anti-My9-blocked ricin treatment (e.g. $10^{-9}$M for 1-24 hours).

Also in a preferred embodiment, the present invention provides an in vitro method of purifying cell populations contaminated with cells that express the CD33 antigen. The method comprises culturing the cell populations in the presence of anti-CD33-blocked lectin immunoconjugate and then removing dead cells.

The conditions of non-clinical in vitro use are well known to and/or readily determined by the skilled artisan as described for the in vitro method using anti-CD19-blocked lectin immunoconjugates.

According to a further preferred embodiment, the present invention provides a medicament for treatment of medical conditions adversely associated with cells that express the CD56 antigen, wherein the medicament comprises, (A) a pharmaceutically effective amount of an anti-CD56-blocked lectin immunoconjugate; and (B) a pharmaceutically acceptable carrier, diluent or excipient.

The method for treatment of medical conditions adversely associated with cells that express CD56 antigen according to the present invention comprises in vivo or ex vivo treatment of a subject in need of such treatment with a pharmaceutically effective amount of anti-CD56-blocked lectin immunoconjugate.

The anti-CD56-blocked lectin immunoconjugate is effective against neuroendocrine-type tumors. Neuroendocrine-type tumors include small cell lung cancer (SCLC), pituitary adenomas, medullary thyroid carcinoma, carcinoids, islet cell tumors, neuroblastomas and pheochromocytomas.

The current treatment for SCLC primarily involves intensive combination chemotherapy and radiotherapy. Jackson and Case, *Sem. Onc.* 13, 63-74 (1986) and Postmus et al, in "High Dose Chemotherapy for Small Cell Lung Cancer: Basic and Clinical Aspects" (Hansen, ed.) (1986). While over 75% of patients will demonstrate an objective tumor response to therapy, the median survival of all patients from the onset of therapy is only 11 months. Limiting factors in the use of conventional chemotherapy for treatment is the degree of non-specific toxicity and the development of drug-resistant tumor cells. Treatment of SCLC patients with anti-N901-blocked ricin should be more effective because of its specificity, i.e. killing cells only to which it is targeted, and much higher cytotoxicity i.e, it is capable of killing large numbers of target cells at very low concentrations.

The anti-CD56-blocked lectin immunoconjugate can be used intravenous infusion or ex vivo for killing CD56-positive cells from bone marrow as described for the anti-CD19-blocked lectin and anti-CD33-blocked lectin immunoconjugates.

Other clinical applications of the medicament and method of treating medical conditions adversely associated with cells that express the CD56 antigen can be determined readily by the skilled artisan by assaying for the presence of the CD56 antigen in tissue specimens by methods known in the art or by assaying for production of unwanted antibodies, also by methods known in the art. These clinical conditions can be identified by the presence of CD56-positive cells by the techniques described above for assaying for the presence of CD19-positive cells.

Specific clinical protocols for in vivo and ex vivo use with regard to route of administration, carriers, diluents, excipients, dosages, times, etc., can be determined by the skilled artisan.

In general, the same protocols, doses, carriers, etc., for administration described above for the anti-CD-19- blocked lectin immunoconjugate and the anti-CD33-blocked lectin immunoconjugate are equally applicable to the anti-CD56-blocked lectin immunoconjugate.

Also in a preferred embodiment, the present invention provides an in vitro method of purifying cell populations contaminated with cells that express the CD56 antigen. The method comprises culturing the cell populations in the presence of anti-CD56-blocked lectin immunoconjugate and then removing dead cells.

The conditions of non-clinical in vitro use are well known to and/or readily determined by the skilled artisan as described for the in vitro method using anti-CD19-blocked lectin immunoconjugates.

EXAMPLES

The invention will now be described by reference to specific examples which are not intended to be limiting.

Unless otherwise specified, all percents, ratios, etc. are by weight.

EXAMPLE 1

Figure 2:
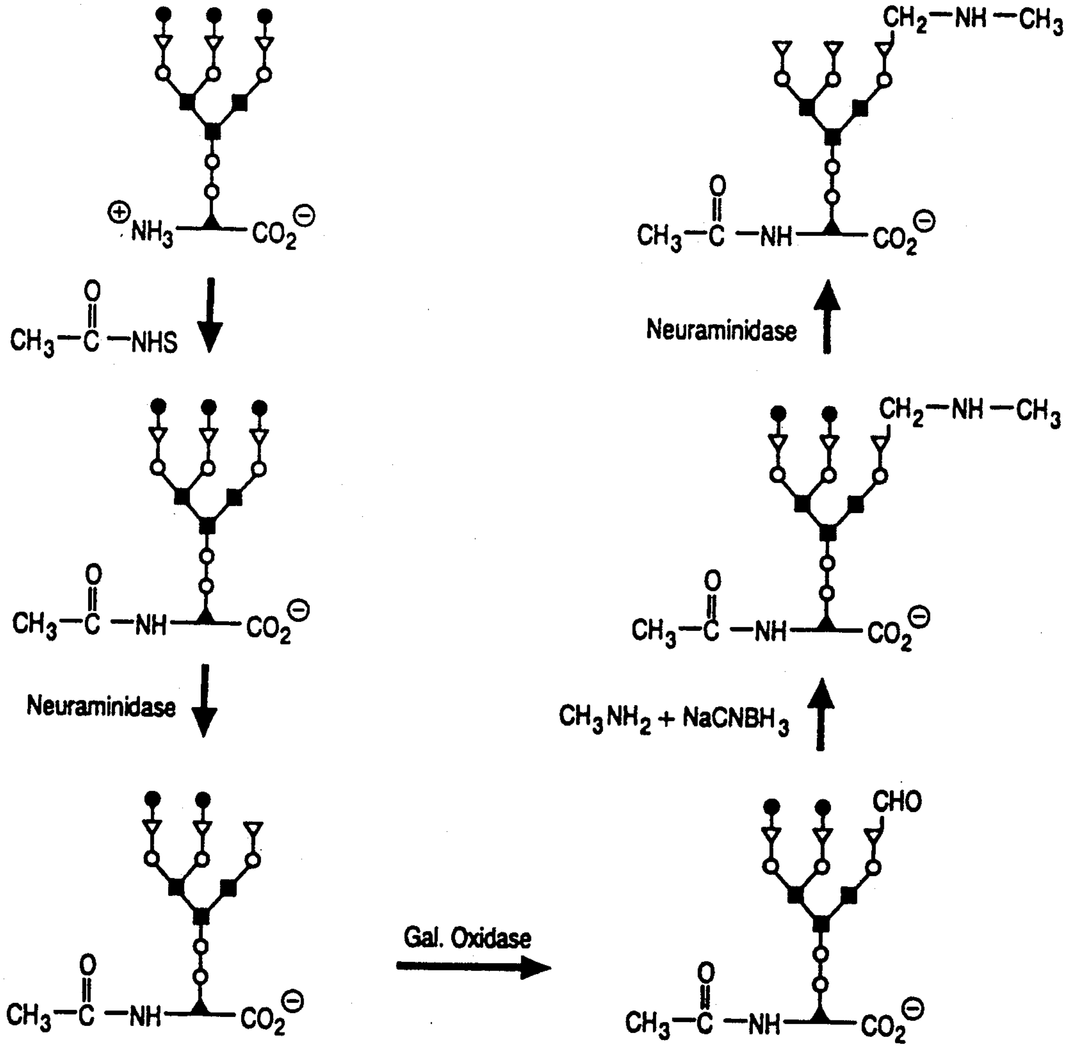
FIG. 2 illustrates the scheme for the synthesis of affinity ligand A described in Example 1.

Preparation of Activated Affinity Ligand A (See FIG. 2)

Preparation of Glycopeptides From Fetuin

N-glycosidically-linked glycopeptides were purified from fetuin as described by Baenziger et al., *J. Biol. Chem.* 254, 789–795 (1979). Fetuin (5 g; from Sigma Chemical Co., St. Louis, Mo.) was dissolved in 100 mL of 100 mM Tris-HCl buffer, pH 7.9, containing $CaCl_2$ (2 mM). Pronase (50 mg from Sigma) and one drop of toluene were added to the solution and digestion was carried out at 37° C. for 24 hours, after which the mixture was lyophilized. The dried digest was redissolved in 20 mLs of distilled water and a small amount of precipitate was removed by centrifugation. The supernatant was applied to a column (2.6 cm×95 cm) of BioGel P-6 equilibrated in $NH_4HCO_3$ (5 g/L) for gel filtration. Fractions that contained N-linked glycopeptide were located by determination of hexose using the phenol-$H_2SO_4$ assay described by Ashwell, *Meth. Enz.* 8, 85–95 (1966). These fractions were combined and pronase (15 mg) and 1 drop of toluene were added to the solution, which was then incubated at 37° C. for 24 hours. This solution was then lyophilized and the dried solid was redissolved in distilled water (7 mL). Small particles were removed by filtration through glass wool and the solution was then submitted to gel filtration on a column (2.6 cm×95 cm) of BioGel P-6 as described above. Fractions containing N-linked glycopeptide were combined and lyophilized. The dry solid was redissolved in 50 mM HEPES buffer, pH 6, (7 mL), 5 Units of carboxypeptidase Y and 5 Units of leucine aminopeptidase (both from Boehringer Mannheim Biochemicals. Indianapolis, Ind.) were added and the solution was incubated at 37° C. for 48 hours, according to the procedure of Lee et al., *J. Biol. Chem.* 258, 199–202 (1983). The glycopeptide fraction was again purified by gel filtration on a column (2.6 cm×95 cm) of BioGel P-6 which was equilibrated in 100 mM pyridine-acetate buffer, pH 5, preferably pH 5.4. The purified glycopeptide fraction was characterized by quantitative assays for hexose as described by Ashwell et al. (cited above) using lactose as a standard, for sialic acid using the method of Warren, *J. Biol. Chem.* 234, 1971–1975 (1959) nd for primary amino groups using the method of Habeeb, *Anal. Biochem.* 14, 328–336 (1966). The molar ratio of the hexose, sialic acid and amino groups was about 6:3:1, respectively, as described previously by Baenziger et al. (cited above).

Finally, the glycopeptide preparation was further purified by ion-exchange chromatography on a column of DEAE-cellulose (Whatman DE-52, about 200 mL bed volume) equilibrated in 2 mM pyridine-acetate buffer, pH 5, preferably pH 5.4. The glycopeptide fraction was diluted 50-fold with water and applied to the column. The column was then washed with the 2 mM pyridine-acetate buffer (about 2 column volumes) and later developed using a buffer with a gradient of molarity increasing from 2 mM to 500 mM (2×1000 mL). The glycopeptides eluted as two major peaks, fraction I (FI) and fraction II (FII), and two minor peaks, fraction O (FO) and fraction III (FIII). FI, FII, and FIII correspond to the glycopeptide fractions reported by Baenziger et al. (cited above), and a small fraction that eluted from the column before FI was designated by the present inventors as FO. The peaks were pooled separately, dried by rotary evaporation and finally lyophilized from water. All the glycopeptide fractions were similar in composition, as described by Baenziger et al. (cited above), and any one of them can be used in the preparation of activated affinity ligands (A, B or C). or In the following description in this Example and Examples 2, 3 and 4, the term glycopeptide will be used for each and any of the glycopeptide fractions from fetuin. The yield in all four fractions was 524 mg of glycopeptide (about 176 μmol) from 5 g of fetuin.

FIG. 1(A) is a representation of the structure of glycopeptides that contain N-glycosidically-linked branched oligosaccharides from fetuin as proposed by Baenziger et al., *J. Biol. Chem.* 254, 789–795 (1979).

FIG. 1(B) is a representation of the structure of glycopeptides containing the N-glycosidically-linked branched oligosaccharides from fetuin as proposed by Nilsson et al., *J. Biol. Chem.* 254, 4545–4553 (1979). which differs from the structure represented in FIG. 1(A) at one branch point. The structure represented in FIG. 1(B) has been confirmed by more recent analyses done by Takasaki et al., *Biochem.* 25, 5709–5715 (1986) and Townsend et al., *Biochem.* 25, 5716–5725 (1986) as being the predominant form of N-linked oligosaccharide in fetuin. The N-linked glycopeptides made from fetuin are the starting compounds for the reactions leading to the production of the affinity ligands A, B and C in this Example and Examples 2, 3 and 4.

Synthesis of Affinity Ligand A from Glycopeptide Derived From Fetuin

The steps in the synthesis of affinity ligand A are illustrated in FIG. 2 and described in detail below.

Acetylation of the α-Amino Group of the Glycopeptide

Glycopeptide (19 mM) in water was mixed with an equal volume of aqueous $NaHCO_3$ (1M). Then a 20-fold molar excess of N-succinimidylacetate which was freshly dissolved in dry dioxane was added as six equal portions contained 20% dioxane. After the final incubation. acetic acid was added (1M final concentration) and the solution was dried by rotary evaporation. The dry material was dissolved in 50 mM pyridine-acetate buffer, pH 5 and the N-acetylglycopeptide was purified by gel filtration on a column of BioGel P-6 (Fine) equilibrated with the same buffer. The glycopeptide fractions, located by hexose assay (Ashwell, cited above), were pooled and pyridine-acetate removed by repeated drying from water by rotary evaporation and, finally, lyophilization. The N-acetylglycopeptide product was dissolved in water and quantitative assays for hexose, sialic acid, and primary amino groups were performed as described above. The level of amino groups was very low, 0.05 amino groups/mole. A second cycle of treatment with N-succinimidylacetate reduced the level of amino groups to zero (detection limit 0.002 amino groups/mole).

This acylation step can also be performed such that the methyl group is replaced with another group that is inert to any subsequent reactions performed on the ligand or with the ligand present, such as a hydrogen atom (for example by using N-succinimidylformate), an alkyl group having 2 or more carbon atoms (for example by using N-succinimidylpropionate) but preferably not more than 6 carbon atoms, or an aryl group (for example by using N-succinimidylbenzoate).

Partial Removal of Sialic Acid From N-Acetylglycopeptide by Enzymic Hydrolysis With Neuraminidase One-tenth volume of 0.5M sodium acetate, pH 5, containing NaCl (1.5M) and $CaCl_2$ (0.1M) was added to a solution of the N-acetylglycopeptide (20 mM). The pH was adjusted to 5 by the addition of NaOH or Tris base. Then neuraminidase. E.C.3.2.1.18, from *Clostridium perfringens* or from *Vibrio cholerae* (both purchased from Sigma Chemical Co.) was added to the solution (0.2 Units of enzyme per mL of incubation: 1 Unit defined as the amount needed to liberate 1.0 μmole of sialic acid per minute at pH 5 and 37° C. using sialyllactose as a substrate) and the solution was then incubated at 37° C. for 1.5 hours. The release of sialic acid was monitored by the assay method of Warren, supra. About 30–35% of the total sialic acid is released from the glycopeptide by enzymic hydrolysis under these conditions. The partially desialated N-acetylglycopeptide was purified from the reaction mixture by gel filtration over a column of BioGel P-6 (Fine) equilibrated with 100 mM sodium phosphate buffer, pH 7. The fractions containing glycopeptide were located by the hexose assay, pooled, and quantitative assays for hexose and sialic acid were performed. The molar ratio of sialic acid:hexose was about 1:3, compared with 1:2 for the non-hydrolysed N-acetylglycopeptide, corresponding to the release of about 1 sialic acid per mole of glycopeptide which will result in about 1 terminal galactose moiety per mole of glycopeptide.

Oxidation of Partially Desialated N-Acetylglycopeptide Using Galactose Oxidase The glycopeptide (2.5 mM) in 100 mM sodium phosphate buffer, pH 7, after treatment with neuraminidase, was placed in a glass vial which had been pretreated overnight with pH 7 buffer containing 1 mg/mL BSA. Horse radish peroxidase. E.C.1.11.1.7 (10 μg/mL), and catalase. E.C.1.11.1.6 (1 μg/mL), were added to the solution. Then, for each μmole of glycopeptide, 0.5–1.0 Units of galactose oxidase. E.C. 1.1.3.9 (from *Dactylium dendroides*, purchased from Sigma Chemical Co., as were the horse radish peroxidase and catalase), were added to the mixture which was then incubated at 30° C. for 16–30 hours. One Unit of enzymic activity is as defined by Sigma ($A_{425nm}$ of 1.0 per minute at pH 6 at 25° C. in a peroxidase and O-tolidine system). The activity of the galactose oxidase was checked before use by using a similar assay described by Amaral et al., *Meth. Enz.* 9, 87–92 (1966) that used O-dianisidine in place of O-tolidine which gives value for activity that are close to those of Sigma, or by using the assay described by Tressel and Kosman. *Anal. Biochem.* 105, 150–153 (1980) using 3-methoxybenzyl alcohol as a substrate. The oxidation of terminal galactose residues to give an aldehyde function on carbon-6 of the sugar was followed by measuring the appearance of reducing groups using the arsenomolybdate assay described by Somogyi, *J. Biol. Chem.* 195, 19–23 (1952). When the oxidation was complete, the aldehyde function was used in a reductive amination reaction as described below, without purifying the oxidized, partially desialated N-acetylglycopeptide from the reaction mixture. Reductive oxidation of any of the three D-galactose residues is permissible.

Reductive Amination of Oxidized, Partially Desialated N-acetylglycopeptide

Methylamine-HCl from a stock solution of 6.7M methylamine-HCl, pH 7, was added to a final concentration of 0.5M to the galactose oxidase reaction mixture which was described above. The solution was incubated at 30° C. for 4 hours, and then $NaCNBH_3$ was added to a final concentration of 3 mg/mL (50 mM) and the solution was then incubated for one hour at room temperature. The $NaCNBH_3$ had been purified by the method of Borch et al., J. Am. Chem. Soc. 93, 2987–2904 (1971), to ensure that it was free of $NaBH_4$, and was stored in a sealed bottle over Drierite. Three further additions were made at hourly intervals. After the final addition of $NaCNBH_3$ the solution was incubated for 16 hours at room temperature. The reaction mixture was then dried by rotary evaporation and the residue was dissolved in a minimal volume of water. The glycopeptide was purified by gel filtration on a column of BioGel P-6 (Fine) equilibrated in 20 mM pyridine-acetate buffer, pH 5. The fractions containing glycopeptide were pooled and the buffer was removed by three cycles of rotary evaporation from water and finally by lyophilization. Aldehyde groups were now undetectable in the glycopeptide (Somogyi assay, see above), the 6-deoxy-6-oxo-D-galactose residue being converted to N-methyl-6-amino-6-deoxy-D-galactose (MADG) by reductive amination.

The partially desialated N-acetylglycopeptide containing the galactosamine MADG was fractionated by ion-exchange chromatography by passing the solution over a column of DEAE-cellulose (Whatman DE-52) equilibrated in 2 mM pyridine-acetate buffer, pH 5, which was run as described above in the purification of glycopeptides from fetuin. The amount of hexose and sialic acid in each fraction was quantified as described above. In this way, modified glycopeptide that contained 1 or 2 sialic acid residues per mole of glycopeptide could be separated from fractions having no sialic acid (complete hydrolysis by neuraminidase) or fractions having about 3 sialic acid residues per mole of glycopeptide (no hydrolysis by neuraminidase). The latter two fractions were not used further, since one (having no sialic acid) would likely not contain any non-modified galactose (sialic acid protects galactose from oxidation by galactose oxidase), important for binding to ricin and other cytotoxic lectins, while the other fraction (having 3 sialic acids per mole) would likely not contain any MADG, important for the activation step. The desired fractions were pooled and solvent removed by rotary evaporation and then lyophilization as described above.

The extent of incorporation of methylamine by a reductive amination reaction with the oxidized galactose of the partially desialated N-acetylglycopeptide could be measured by performing a parallel reaction on a sample of the glycopeptide with [$^{14}$C] methylamine (7.6 $\mu$Ci/mmole) as described in detail in Example 4.

The reductive amination step can also be performed such that the methyl group is replaced with a hydrogen atom (e.g. by using benzylamine and a catalytic hydrogenation as described by Lee et al., *Biochem.* 25, 6835–6841 (1986) or by using ammonium ions for the reductive amination reaction as described by Hara et al., *Anal. Biochem.* 97 166–172 (1979)), an alkyl group of two or more carbon atoms (e.g. by using ethylamine), preferably not more than 5 carbon atoms, or an aryl group (e.g. by using aniline).

Complete Removal of Sialic Acid From the Partially Desialated N-Acetylglyopeptide-containing Galactosamine (MADG) by Enzymic Hydrolysis With Neuraminidase The complete hydrolysis of the glycosidic bonds between sialic acid and galactose (see FIG. 1) was performed as for the partial enzymic hydrolysis by neuraminidase described above, except that the molar ratio of enzyme to substrate was 10-fold greater, and the incubation was continued for 24–48 hours at 37° C. until all of the sialic acid was liberated as determined by the assay of Warren (cited above). Occasionally, a second addition of enzyme was found to be necessary after 24 hours, with incubation continued for another 24 hours. Finally, the product of this enzymic hydrolysis, asialo-N-acetylglycopeptide containing MADG, which is the affinity ligand A, was purified by gel filtration over a column of BioGel P-6 (Fine) equilibrated in 100 mM pyridine-acetate buffer, pH 5. The fractions containing the affinity ligand A were pooled and solvent removed as described above by rotary evaporation and lyophilization to yield a white powder, affinity ligand A.

Activation of Affinity Ligand A With Cyanuric Chloride

The affinity ligand A (0.6 $\mu$mol) was dissolved in 100 mM sodium phosphate buffer, pH 7, (0.45 mL). Dioxane (0.215 mL) was added to the solution and then a 1.2-fold molar excess of cyanuric chloride (12.4 $\mu$L of a 10 mg/mL solution freshly prepared in dry dioxane) was added with continuous vortex-mixing at room temperature. The solution had a final dioxane:water ratio of 1:3 by volume. The solution was vortex-mixed for exactly one minute, and then concentrated HCl (5 $\mu$L) was added with continuous mixing in order to lower the pH to near 3 which stops further reaction. The activated affinity ligand A was separated from the reagents by gel filtration on a column of BioGel P-6 (Fine) equilibrated with 50 mM sodium phosphate buffer, pH 3. The fractions containing the ligand were located by hexose assay, and then pooled and the concentration of ligand determined by quantitative hexose assay using lactose as a standard. The solution of ligand was kept at 0° C. for immediate use in preparation of a blocked cytotoxic lectin.

The level of activation of the affinity ligand with cyanuric chloride could be determined by reaction of a sample of the activated ligand with a 4000-fold molar excess of $^{14}$C-methylamine (Amersham) diluted to 50 $\mu$Ci/mmole with non-radioactive methylamine. Incubation was at pH 8 for 70–100 hours at 25° C. The ligand was then purified by gel filtration over a column of BioGel P-6 (Fine) equilibrated in 0.1M acetic acid. 7 mM pyridine, pH 3.5, and the extent of reaction of the $^{14}$C-methylamine with the activated affinity ligand was determined by measuring the radioactivity incorporated into the ligand fraction by scintillation counting. Non-activated ligand was used as a control.

Affinity ligand A was also activated with 2,4-dichloro-6-methoxytriazine using the same conditions as described above for using cyanuric chloride.

EXAMPLE 2

Figure 3:
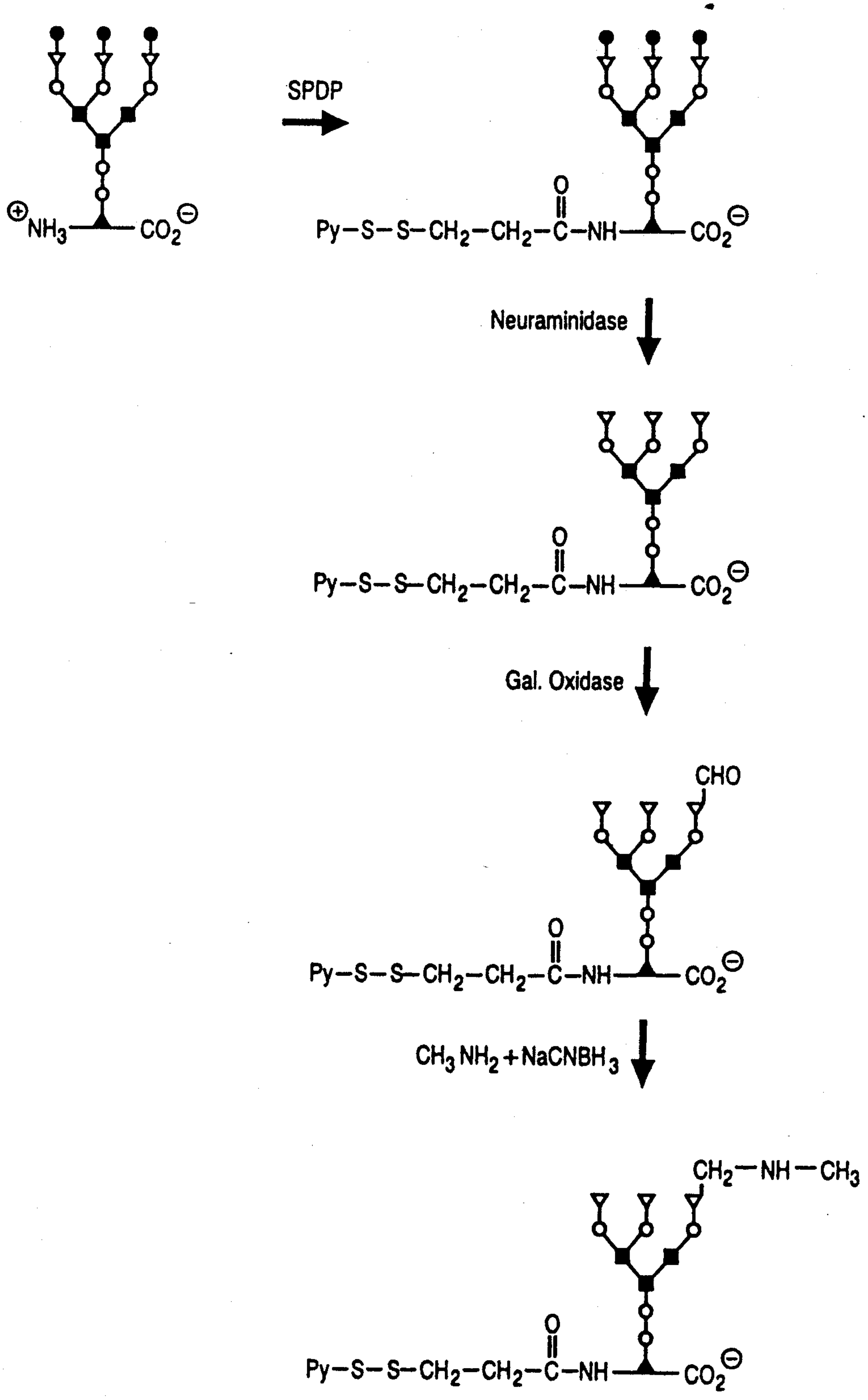
FIG. 3 illustrates the scheme for the synthesis of affinity ligand B described in Example 2.

Preparation of Activated Affinity Ligand B (See FIG. 3)

Preparation of Glycopeptides From Fetuin

Glycopeptides used in this example were prepared and purified as described in Example 1.

Synthesis of Affinity Ligand B From Glycopeptide Derived From Fetuin

The steps in the synthesis of affinity ligand B are illustrated in FIG. 3.

Reaction of the $\alpha$-amino Group of the Glycopeptide With N-succinimidyl-3-(2-pyridyldithio)propionate (SPDP)

Glycopeptide (57 $\mu$mol) was first dissolved in water (3 mL), then was mixed with 1.5 mL of $NaHCO_3$ (1M) and finally with a 5-fold molar excess of SPDP dissolved in 0.75 mL of dry dioxane. The solution was stirred for 30 min, at 30° C., and then 4 more additions of SPDP, each of 57 $\mu$mol dissolved in 0.6 mL of dry dioxane, were made at 30 minute intervals, maintaining incubation at 30° C. After the final incubation, acetic acid (5% by volume, final concentration) was added to the mixture which was then dried by rotary evaporation. The residue was suspended in 1 mL of 50 mM pyridine-acetate pH 5. An oil was extracted with ethyl acetate (about 2 mL) and the cloudy aqueous solution was dried again. The residue was dissolved in 4 mL of 50 mM pyridine-acetate buffer, pH 5 and passed over a column of BioGel P-6 (Fine) equilibrated with the same buffer. Fractions containing 3-(2-pyridyldithio)propionylglycopeptide were combined and recovered by rotary evaporation and lyophilization as above. The glycopeptide was quantified by the hexose assay (Ashwell, cited above) and pyridyldisulfide groups were measured by the method of Carlsson et al., *Biochem. J.* 173, 723–737 (1978).

This step of linking to the ligand a moiety capable of linking the ligand to a cell-binding agent can be conducted by replacing the pyridyl with another aryl group. For example, to incorporate another aryl group. N-succinimidyl-3-(phenyldithio)propionate can be used and to incorporate an alkyl group, N-succinimidyl-3-(methyldithio)propionate can be used. However, a pyridyl group is preferred. Also the carbon chain can have one or more carbon atoms, preferably one to five carbon atoms (e.g. by using N-succinimidyl-4-(2-pyridyldithio)butyrate or N-succinimidyl-5-(2-pyridyldithio)valerate).

Complete Removal of Sialic Acid From 3-(2pyridyldithio)propionalglycopeptide by Enzymic Hydrolysis With Neuraminidase This enzyme reaction was performed as described in the preparation of affinity ligand A in Example 1.

Partial Oxidation of 3-(2-pyridyldithio)propionylasialoglycopeptide

The modified glycopeptide (3 mM) was dissolved in 100 mM sodium phosphate buffer, pH 6.8, and was treated with galactose oxidase using the conditions described above in Example 1. The extent of oxidation of the terminal galactose, resulting in aldehyde functions on carbon-6 of the sugar, was followed by measuring the appearance of reducing groups using the arsenomolybdate assay described by Somogyi (cited above in Example 1). The enzymic oxidation was only allowed to proceed until about 1.0–1.5 aldehyde groups were introduced per mole of modified glycopeptide. It is important that the glycopeptide ligand still contained at least one non-modified galactose which is necessary for the specific binding of the ligand to ricin and other cytotoxic lectins. When the desired extent of oxidation by galactose oxidase was achieved, the reaction mixture was dried by rotary evaporation and the modified glycopeptide purified by gel filtration on a column of Bio-Gel P-6 (Fine) in 50 mM pyridine-acetate buffer, pH 5. Alternatively, the oxidized ligand can be used directly in the reaction with methylamine described below, without further purification.

Reductive Amination of the Partially Oxidized 3-(2-pyridyldithio)propionylasialoglycopeptide Methylamine-HCl from a stock solution of 6.7M methylamine-HCl, pH 7, was added to a final concentration of 0.5M to the partially oxidized, modified glycopeptide derivative in the galactose oxidase reaction mixture described above (3 mM ligand), as soon as the extent of oxidation was sufficient. The pH was adjusted to 6.2 and the solution incubated at 30° C. for 4 hours. The solution was then treated with purified $NaCNBH_3$ as described in Example 1.

Quantitative assays for hexose and pyridyldisulfide showed that $NaCNBH_3$ under these conditions did not reduce the disulfide bond of the pyridyldisulfide group.

Assay of aldehyde groups, now undetectable, indicated that the oxidized galactose moiety had been converted to MADG.

The modified glycopeptide was purified from the reaction mixture by gel filtration by passing the solution through a column of BioGel P-6 (Fine) equilibrated with 100 mM pyridine-acetate buffer, pH 5. The fractions that were found to contain the 3-(2-pyridyldithio)-propionylasialoglycopeptide with MADG. which is the affinity ligand B, were pooled.

The solvent was removed by rotary evaporation, the affinity ligand B was dissolved in a minimal volume of water and lyophilized.

This reductive amination step can also be performed such that the methyl group is replaced by a hydrogen atom, by an alkyl group of two or more carbon atoms but preferably not more than 5 carbon atoms, or by an aryl group as described in Example 1.

Activation of Affinity Ligand B With Cyanuric Chloride

The affinity ligand B was activated by reaction with cyanuric chloride and purified from the reaction mixture as described above for affinity ligand A in Example 1.

EXAMPLE 3

Figure 4:
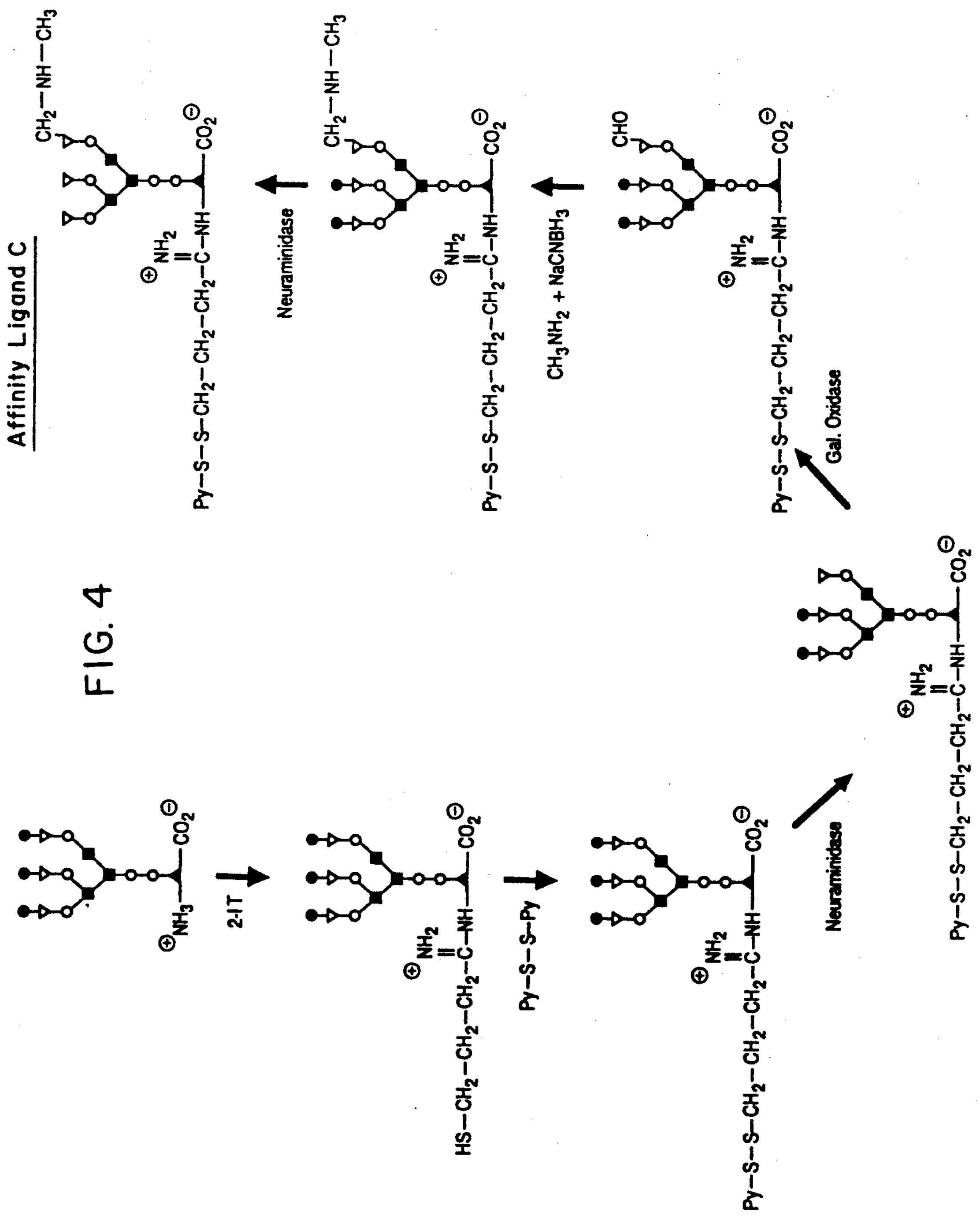
FIG. 4 illustrates the scheme for the synthesis of affinity ligand C described in Example 3.

Preparation of Activated Affinity Ligand C (See FIG. 4)

Preparation of N-glycosidically-linked Glycopeptides From Fetuin

Glycopeptides were purified as in Example 1.

Synthesis of Affinity Ligand C From Glycopeptide Derived From Fetuin

The steps in the synthesis of affinity ligand C are illustrated in FIG. 4.

Reaction of the α-amino Group of the Glycopeptide With 2-iminothiolane

Glycopeptide (55 μmol) was dissolved in 1.0 mL of 0.2M sodium borate buffer, pH 10, with EDTA (5.4 mM). and the pH readjusted to 10 with NaOH. 2-iminothiolane (0.5 mL of a freshly prepared 1.0M solution dissolved in a 1:1 (v/v) mixture of 0.2M sodium borate, pH 10 and 2.0M NaOH) was added and the solution incubated at 25° C. for 3 hours. The pH was then adjusted to 8 with HCl. Solid dithioerythritol was added to a final concentration of 0.5M and the mixture was incubated for 1 hour at 37° C.

The glycopeptide, now modified to contain a free sulfhydryl group, was then purified by gel filtration on a column, of BioGel P-6 (Fine) equilibrated in 100 mM pyridine-acetate buffer, pH 5, containing 5 mM EDTA. Fractions containing the glycopeptide were located using the hexose assay (see Example 1) and pooled for quantitative assays of hexose and sulfhydryl groups.

Hexose and sulfhydyl groups were assayed by the method of Ellman. *Arch. Biochem. Biophys.* 82, 70–77 (1959). As expected, one sulfhydryl group was introduced per mole of glycopeptide under these conditions. The modified glycopeptide was used immediately in a reaction with 2,2'-dithiodipyridine (see below).

This step can be conducted such that the carbon chain has one or more carbon atoms and preferably with 2–6 carbon atoms. Thus the reaction can be conducted using methyl-3-mercaptopropionimidate or methyl-5-mercaptovalerimidate).

Reaction of the Sulfhydryl-containing Glycopeptide With 2,2'-dithiodipyridine

The sulfhydryl-containing glycopeptide from the above reaction (40 μmol in 18 mL pyridine-acetate buffer, pH 5) was diluted to 1 mM glycopeptide with 100 mM pyridine-acetate buffer, pH 5, containing EDTA (1 mM). Additional acetic acid was added to increase acetic acid concentration by 200 mM. 2,2'-dithiopyridine was added to 200 mM final concentration from a 1.0M solution in dry dioxane. The reaction was mixed by rotation for 15 hours. A white precipitate formed and was removed by decanting the solution into a flask for rotary evaporation of the solvent. The modified glycopeptide was then extracted from the dried solid using 4–5 mL of 100 mM pyridine-acetate buffer, pH 5. containing EDTA (1 mM), and then purified by gel filtration through a column of BioGel P-6 (Fine) in 100 mM pyridine-acetate buffer, pH 5. Some preparations were purified further by ion-exchange chromatography on a column of DEAE-cellulose equilibrated in 2 mM pyridine-acetaete buffer, pH 5, using the same procedure as described in Example 1 for the purification of glycopeptides from fetuin. In either case, the modified glycopeptide containing a pyridyldisulfide group was then recovered from the solvent by rotary evaporation. pyridine-acetate removed by four cycles of addition of water followed by rotary evaporation to dryness and finally the modified glycopeptide was lyophilized from water. Sulfhydryl groups were quantitatively converted to pyridyldisulfide groups by this reaction, as measured by the method of Carlsson (cited in Example 2).

This step can also be conducted such that the pyridyl group is replaced with another aryl group (for example, by using diphenyldisulfide) or an alkyl group (for example, by using 2-(2'-pyridyldithio)ethanol, diethyldisulfide, 2-ethyldithio-5-nitrobenzoic acid, etc.).

Partial Removal of Sialic Acid From Modified Glycopeptide by Enzymic Hydrolysis With Neuraminidase The glycopeptide that had been modified with 2-iminothiolane and 2,2'-dithiodipyridine was treated with neuraminidase as described for partial removal of sialic acid in Example 1. Once about 33% of the sialic acid was liberated from the glycopeptide, the enzymic hydrolysis was stopped by get filltration on BioGel P-6 (Fine) equilibrated in 100 mM pyridine-acetate buffer. pH 5. The peak of glycopeptide was then diluted to 2 mM pyridine-acetate buffer, pH 5 (0.1 μmol glycopeptide/mL. final concentration) prior to ion-exchange chromatography over a column containing DEAE-cellulose (20 mL column for 209 μmol glycopeptide) equilibrated in the same buffer. The column was developed with a gradient (2–500 mM) of pyridine-acetate buffer, pH 5. Fractions containing glycopeptide were located using the hexose assay (assay method, cited above), and peaks were then assayed quantitatively for hexose and sialic acid (assay methods, cited in Example 1).

The fraction with a sialic acid: hexose molar ratio of 1:3, suggesting that this fraction contained 2 sialic acid residues per mole of glycopeptide, was obtained in about 50% yield (10.2 μmol from 22 μmol starting material). The solvent was removed from this fraction by rotary evaporation and lyophilization as described above, to prepare the compound for treatment with galactose oxidase as described below.

Another fraction with a lower sialic acid:hexose molar ratio (1:6) was also obtained (about 7 μmol from 22 μmol starting material) and this fraction may also be used to form an activated affinity ligand that can also be used successfully to bloc ricin. This fraction is treated identically to the fraction having a sialic acid:hexose molar ratio of 1:3, in the remaining steps described below in the synthesis of affinity ligand C.

Oxidation of Partially Desialated, Pyridyldithioglycopeptide Using Galactose Oxidase The glycopeptide was oxidized with galactose oxidase as described in the oxidation step for the preparation of affinity ligand A in Example 1. It was then used in the reductive amination reaction without further purification.

Reductive Amination of Oxidized, Partially Desialated Pyridyldithioglycopeptide The oxidized glycopeptide was treated with methylamine and $NaCNBH_3$ as described in the reductive amination step for the preparation of affinity ligand A in Example 1. The pyridyldithioglycopeptide containing MADG that is partially desialated was then purified by gel filtration on a column of BioGel P-6 (Fine) equilibrated in 50 mM pyridine-acetate buffer, pH 5. The glycopeptide was recovered by rotary evaporation and then lyophilization as described above.

This reductive amination step can also be performed such that the methyl group is replaced with a hydrogen atom, an alkyl group of two or more carbon atoms, preferably not more than 5 carbon atoms, or an aryl group as described in Example 1.

Complete Removal of Sialic Acid by Enzymic hydrolysis With Neuraminidase of the Partially Desialated Pyridyldithioglycopeptide Containing Galactosamine (MADG)

This was done with neuraminidase as described in the corresponding step in the preparation of affinity ligand A (Example 1).

The modified asialoglycopeptide, which is the affinity ligand C, was finally purified by gel filtration through a column of BooGel P-6 (Fine) equilibrated in 100 mM pyridine-acetate buffer, pH 5. The fractions containing the affinity ligand C were combined and solvent removed by rotary evaporation. After three cycles of addition of water followed by rotary evaporation, the affinity ligand C was lyophilized from water to yield a dry white powder.

Activation of Affinity Ligand C With Cyanuric Chloride

Affinity ligand C was activated by reaction with cyanuric chloride and then purified from the reaction mixture as described above for the affinity ligand A in Example 1.

EXAMPLE 4

Figure 5:
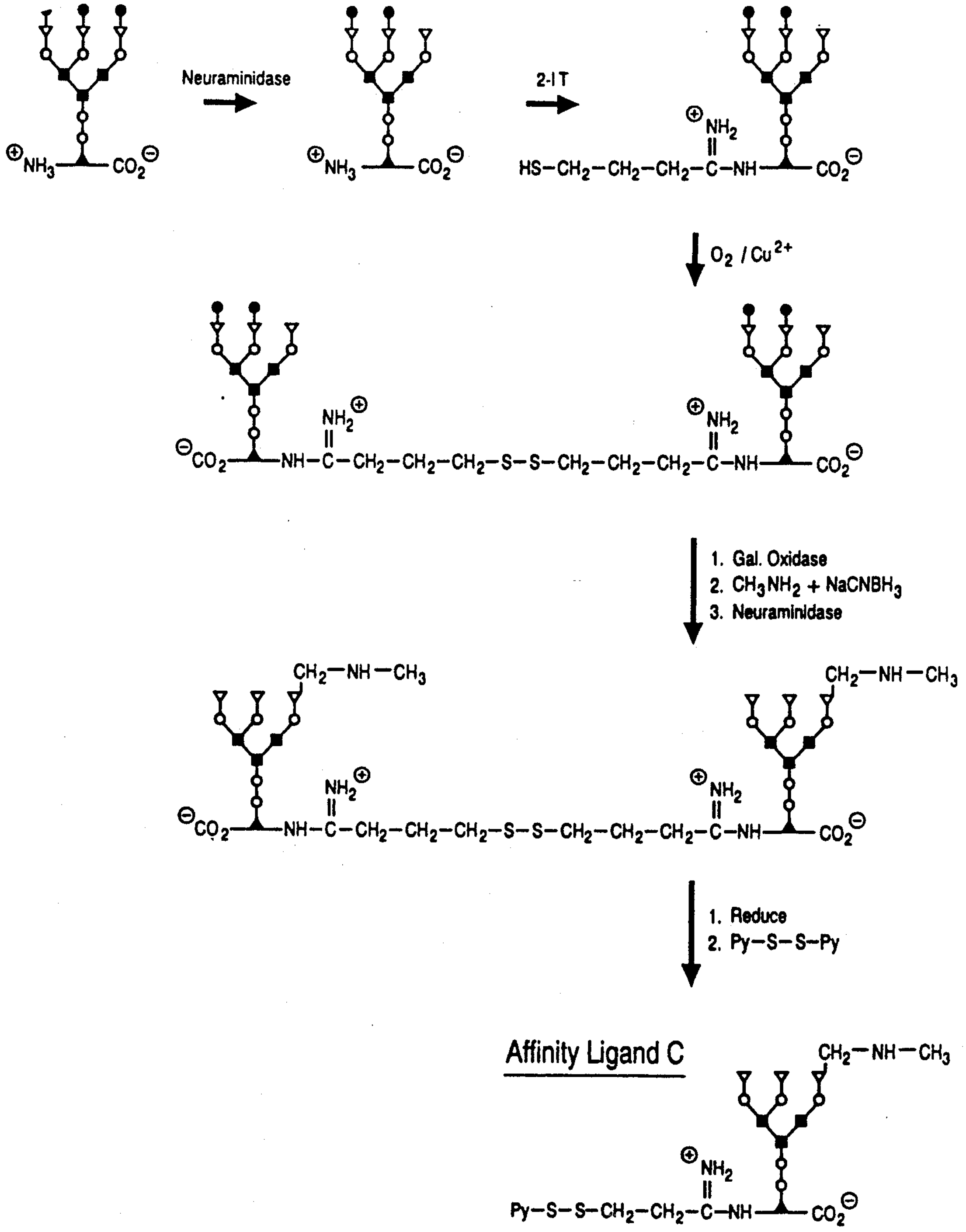
FIG. 5 illustrates an alternative scheme for the synthesis of affinity ligand C described in Example 4.

Alternative Scheme of Reactions for Preparation of Activated Affinity Ligand C (See FIG. 5)

Preparation of N-glycosidically-linked Glycopeptides From Fetuin

N-glycosidically-linked glycopeptides were prepared as described in Example 1.

Synthesis of Affinity Ligand C from Glycopeptide Derived From Fetuin

The steps in the synthesis of affinity ligand C from glycopeptide that is derived from fetuin are illustrated in FIG. 5.

Partial Removal of Sialic Acid From the Glycopeptide by Enzymic Hydrolysis With Neuraminidase This enzyme reaction was performed as described for the partial removal of sialic acid in the preparation of affinity ligand A in Example 1.

The partially desialated glycopeptide was fractionated by ion-exchange chromatography on a column (30 mL) of DEAE-cellulose equilibrated with 2 mM pyridine-acetate buffer, at pH 5, preferably at pH 5.4. The column was washed with 90 mL of buffer and then developed with a gradient (2–500 mM) of pyridine-acetate buffer at pH 5, preferably at pH 5.4 (2×200 mL). Peaks of glycopeptide were located using the hexose assay, and then analyzed quantitatively for hexose and sialic acid. Three separate fractions were pooled. One fraction containing fully sialated glycopeptide (no sialic acid residues removed) was recovered for reuse as starting material. The major fraction (about 50% yield) containing glycopeptide with one sialic acid residue removed by neuraminidase-catalysed hydrolysis and, therefore, eluted earlier in the gradient than non-hydrolysed glycopeptide, was used to prepare affinity ligand C. A third fraction containing glycopeptide with two sialic acid residues removed and, therefore, eluted earlier in the gradient than the above described two fractions, was also used to prepare by an identical procedure a less preferred affinity ligand analogous to C, but containing one non-modified galactose residue and two residues of N-methyl-6-amino-6-deoxy-D-galactose.

The fractions of glycopeptide were dried by rotary evaporation, pyridine-acetate removed by three cycles of adding water followed by rotary evaporation to dryness, and then finally the glycopeptides were lyophilized from water.

Reaction of the α-amino Group of the Partially Desialated Glycopeptide with 2-iminothiolane and Disulfide Dimerization This step was conducted in one of two ways.

In the preferred procedure, the partially desialated glycopeptide was dissolved in 0.2M triethanolamine-HCl buffer, pH 8, containing EDTA (20 mM) to give a glycopeptide concentration of 40 mM. The pH of the solution was readjusted to 8. 2-iminothiolane-HCl (dry solid) was added to give a final concentration of 0.4M, and the pH was readjusted to 8 using NaOH. The mixture was stirred for 48 hours, filtered to remove a small amount of precipitate, and then submitted to gel filtration through a column of Sephadex G-25 (Fine) equilibrated with 0.1M pyridine-acetate pH 5.4 in order to separate the glycopeptide from excess reagent.

The fractions containing glycopeptide were dried by rotary evaporation and then the glycopeptide was put through a second cycle of 2-iminothiolane treatment and Sephadex G-25 purification. The 2-iminothiolane-modified glycopeptide fractions were combined, dried by rotary evaporation, and then redissolved in 0.5M triethanolamine-HCl buffer, pH 8, containing EDTA (50 mM) at a glycopeptide concentration of 40 mM. The pH was adjusted to 8 with NaOH and solid dithiothreitol was added to give a 1.0M final concentration. The solution was incubated at 37° C. for 16 hours, and then applied to a column of Sephadex G-25 (Fine) equilibrated in 0.1M pyridine-acetate, pH 5.4, containing EDTA (20 mM), to, separate reduced modified glycopeptide from excess dithiothreitol. This modification procedure results in between 0.7 and 1.0 sulfhydryl groups per glycopeptide as measured by the method of Ellman, *Arch. Biochem. Biophys.*, 82, 70–77 (1959).

The reduced, modified glycopeptide was dried by rotary evaporation, was dissolved in 0.5M triethanolamine-HCl buffer, pH 8, and was submitted to gel filtration over a column of Sephadex G-25 (Fine) in 0.1M $NaHCO_3$ in order to remove EDTA. The fractions containing glycopeptide were combined, and then the sulfhydryl groups were oxidized by adding $CuSO_4$ (to 40 μM) and O-phenanthroline (to 200 μM) from a stock mixture of 1 mM $CuSO_4$ containing 5 mM O-phenanthroline. The solution was aerated until the concentration of free sulfhydryl groups was zero (24–72 hours). The solution was then dried by rotary evaporation, dissolved in a minimal volume of water and subjected to filtration over a column of Sephadex G-50 (Fine) in 0.1M sodium phosphate buffer, pH 7.

Glycopeptide peaks were located by the hexose assay and the fractions containing disulfide-linked dimeric glycopeptide were combined for the next step in the synthesis of affinity ligand C.

In an alternative, less preferred procedure, the partially desialated glycopeptide was modified with 2-iminothiolane as described for modification of the glycopeptide in Example 3.

The sulfhydryl groups so introduced into the glycopeptide were protected for the subsequent chemical and enzymic steps by oxidizing the sulfhydryl-containing glycopeptide to form disulfide-linked dimers of the glycopeptide. Oxidation was effected by addition to a final concentration of 10 μM $CuSO_4$ and 50 μM O-phenanthroline from a stock mixture of 1 mM $CuSO_4$ containing 5 mM O-phenanthroline. The solution was then mixed by rotation until the concentration of free sulfhydryl groups was zero (24 hours). The solution was then dried by rotary evaporation. The solid residue was dissolved in a minimal volume of water and was subjected to gel filtration on a column of BioGel 30 (Fine) equilibrated in 100 mM sodium phosphate buffer, pH 7. Glycopeptide peaks were located by the hexose assay.

If the reaction with 2-iminothiolane had not gone to completion, a peak having the same elution volume as that of unmodified monomeric glycopeptide was observed. This fraction could be recovered and recycled through the reaction sequence using the 2-iminothiolane.

Those fractions containing disulfide-linked dimeric glycopeptide were combined for the next step (step below) in the synthesis of affinity ligand C.

Oxidation of Partially Desialated Disulfide-linked Dimeric Glycopeptide Using Galactose Oxidase The dimeric glycopeptide was oxidized with galactose oxidase as described in the oxidation step for the preparation of affinity ligand A in Example 1. When the oxidation was complete, the oxidized dimeric glycopeptide was purified by gel filtration through a column of Sephadex G-50 (Fine) equilibrated with 0.1M pyridine-acetate buffer, pH 5.4. The fractions containing glycopeptide were combined and the solvent was removed by rotary evaporation followed by three cycles of rotary evaporation from water and then lyophilization. The resulting glycopeptide was used directly in a reductive amination reaction as described below.

Less preferably, the oxidized dimeric glycopeptide was used directly in a reductive amination reaction as described below.

Reductive Amination of Oxidized, Partially Desialated Disulfide-linked Dimeric Glycopeptide This step was conducted in one of two ways.

In the preferred procedure, the oxidized glycopeptide was treated with methylamine and $NaCNBH_3$ at pH 6.5. Glycopeptide was dissolved in water (to 100 mM final concentration) and the pH was adjusted to 6.5 with NaOH. Aqueous methylamine (40% w/w) was chilled in ice and was slowly titrated to pH 6.5 with acetic acid. The final solution volume was adjusted to 6.0M (±0.5) in methylamine. Methylamine-acetate was then added to the aqueous solution of glycopeptide (4 mL of 6M methylamine-acetate added for 100 μmol of glycopeptide in 1 mL of water). Immediately, solid recrystallized $NaCNBH_3$ was added to the reaction mixture (0.33 mmol added per 100 μmol of glycopeptide in 5 mL total volume). The $NaCNBH_3$ was recrystallized as described in Example 1. The solution was incubated for 90 min, at 40° C. after which a further equal amount of $NaCNBH_3$ was added and the incubation at 40° C. continued for a further 90 min. The glycopeptide was then purified from excess reagent by gel filtration on a column of Sephadex G-25 (Fine) equilibrated in 0.1M pyridine-acetate buffer, pH 5.4. The fractions with the glycopeptide, which now contained the MADG moiety, were located by the hexose assay and pooled. The solvent was removed by rotary evaporation and then three cycles of addition of water followed by rotary evaporation were performed, followed by lyophilization from water.

In an alternative, less preferred procedure, the oxidized glycopeptide was treated with methylamine and $NaCNBH_3$ as described in the reductive amination step for the preparation of affinity ligand A in Example 1. The reaction was stopped by gel filtration through a column (80 mL) of BioGel P-6 equilibrated in 100 mM acetic acid containing 7 mM pyridine. The fractions with the glycopeptide now containing MADG, were located by hexose assay, combined, and the solvent removed by rotary evaporation, three cycles of rotary evaporation from water followed by lyophilization from water.

The incorporation of methylamine into the glycopeptide by reductive amination following either procedure can be monitored in small-scale reactions using [$^{14}$C]methylamine (Amersham). Specific radioactivity was diluted to 7.6 μCi/mmol for these experiments, which used 0.1–0.2 μmol of glycopeptide (amount known accurately). After incubation with methylamine and $NaCNB_3$, the glycopeptide was subjected to gel filtration through a small column of BioGel P-6 (Fine) (38 cm×1 cm) equilibrated with 100 mM acetic acid containing 7 mM pyridine. Then 1 mL fractions were collected and the radioactivity was measured in 0.5 mL samples by scintillation counting. From the total radioactivity that eluted from the column with an elution volume corresponding to the glycopeptide, the amount of methylamine incorporation into the glycopeptide was determined. The incorporation of methylamine was stoichiometric with the level of aldehyde groups that were consumed in the reductive amination reaction. Controls where the glycopeptide lacked any oxidized galactose showed virtually no incorporation of label. The radioactive methylamine incorporated into the glycopeptide was stable to incubation with 5.0M methylamine-acetate, pH 6.5 (5000-fold molar excess) at 25° C. for 60 days.

Complete Removal of Sialic Acid From Partially Desialated Disulfide-linked Dimeric Glycopeptide Containing Galactosamine (MADG)

This was done with neuraminidase as described in the corresponding step in the preparation of affinity ligand A (Example 1). Once enzymic hydrolysis was complete, as determined by the assay for free sialic acid (see Example 1), the glycopeptide was used in the next reaction step without any further purification.

Reduction of Disulfide-linked Dimeric Glycopeptide Containing MADG, and Reaction of the Thiol Group So Generated With 2,2'-dithiodipyridine This step was conducted in one of two ways.

In the preferred procedure, glycopeptide dimer (20 mM) was adjusted to pH 8 by the addition of triethanolamine base, and EDTA was added to 10 mM final concentration. Solid dithiothreitol was added to 0.4M final concentration and the solution was incubated for 16 hours at 37° C.. The reduced glycopeptide was purified by gel filtration through a column of BioGel P-6 (Fine) equilibrated in 5 mM sodium acetate buffer, pH 4.5, containing NaCl (50 mM) and EDTA (5 mM). The fractions containing glycopeptide were pooled and assayed for hexose and sulfhydryl groups to ensure that the reduction was complete (about 1.0 sulfhydryl group per mole of glycopeptide).

The reduced sulfhydryl-containing glycopeptide was then reacted with 2,2'-dithiodipyridine. The glycopeptide pool in pH 4.5 buffer was placed in a dropping funnel and allowed to run into a rapidly stirring solution of 95% v/v ethanol containing 48 mM triethanolamine-HCl buffer, pH 8 and 60 mM 2,2'-dithiodipyridine. One volume of glycopeptide (5 mM in glycopeptide) was run into 4 volumes of the above ethanolic solution of 2,2'-dithiopyridine. The operation was performed under an atmosphere of nitrogen. The reaction was stirred at ambient temperature for 30 min., and then glacial acetic acid was added to 1% (v/v) final concentration. The solution was concentrated by rotary evaporation and the precipitated material was removed by filtration. The affinity ligand C was purified from the clear liquid by gel filtration through a column of BioGel P-30 (Fine) equilibrated in 0.05M pyridine-acetate buffer, pH 5.4. The fractions containing glycopeptide were located by the hexose assay while thiopyridyl groups incorporated into the glycopeptide were measured by the method of Carlsson et al. (cited above in Example 2). The glycopeptide was recovered by rotary evaporation and lyophilization from water (described above in Examples 1, 2 and 3) to yield affinity ligand C.

In an alternative, less preferred procedure, glycopeptide dimer (2.5 mM) was adjusted to pH 8 by the addition of triethanolamine base, and EDTA was added to 5 mM final concentration. Solid dithioerythritol was added to 0.1M final concentration and the solution incubated for 2 hours at 37° C.. The reduced glycopeptide was purified by gel filtration through a column of BioGel P-6 (Fine) that was equilibrated with 100 mM pyridine-acetate buffer at pH 5, containing EDTA (5 mM). The fractions containing glycopeptide were pooled and assayed for hexose and sulfhydryl groups to ensure the reduction was complete (1 sulfhydryl group per mole of glycopeptide).

The reduced sulfhydryl-containing glycopeptide was reacted with 2,2'-dithiodipyridine and purified from the reaction mixture as described in Example 3. The glycopeptide was assayed using the hexose assay and thiopyridyl groups were measured by the method of Carlsson et al. (cited above). The glycopeptide was recovered by rotary evaporation and lyophilization from water in the usual way (described above in Examples 1, 2 and 3) to yield affinity ligand C.

Activation of Affinity Ligand C With Cyanuric Chloride

This step was conducted in one of two ways.

In the preferred procedure, affinity ligand C was activated by reaction with cyanuric chloride. Affinity ligand C was dissolved in 1.0M triethanolamine-HCl buffer, pH 8, to give a 5 mM solution. Four volumes of 0.1M 2,2'-dithiodipyridine in absolute ethanol were added and the solution was stirred at ambient temperature. Cyanuric chloride (1M in dry dioxane) was added to a 50-fold molar excess over affinity ligand C, the mixture stirred rapidly for 1 minute and acetic acid was added to 20% (v/v) final concentration. The activated ligand C was then purified by gel filtration on a column of BioGel P-6 (Medium) equilibrated in 20 mM sodium phosphate-HCl buffer, pH 3. The activated ligand was identified by the hexose assay and the fractions pooled for the subsequent reaction with ricin.

In an alternative, less preferred procedure, affinity ligand C was activated by reaction with cyanuric chloride and then purified from the reaction mixture as described above for the affinity ligand A in Example 1.

Affinity ligand was also activated with 2,4-dichloro-6-methoxytriazine using the same conditions described for either procedure.

EXAMPLE 5

Figure 6:
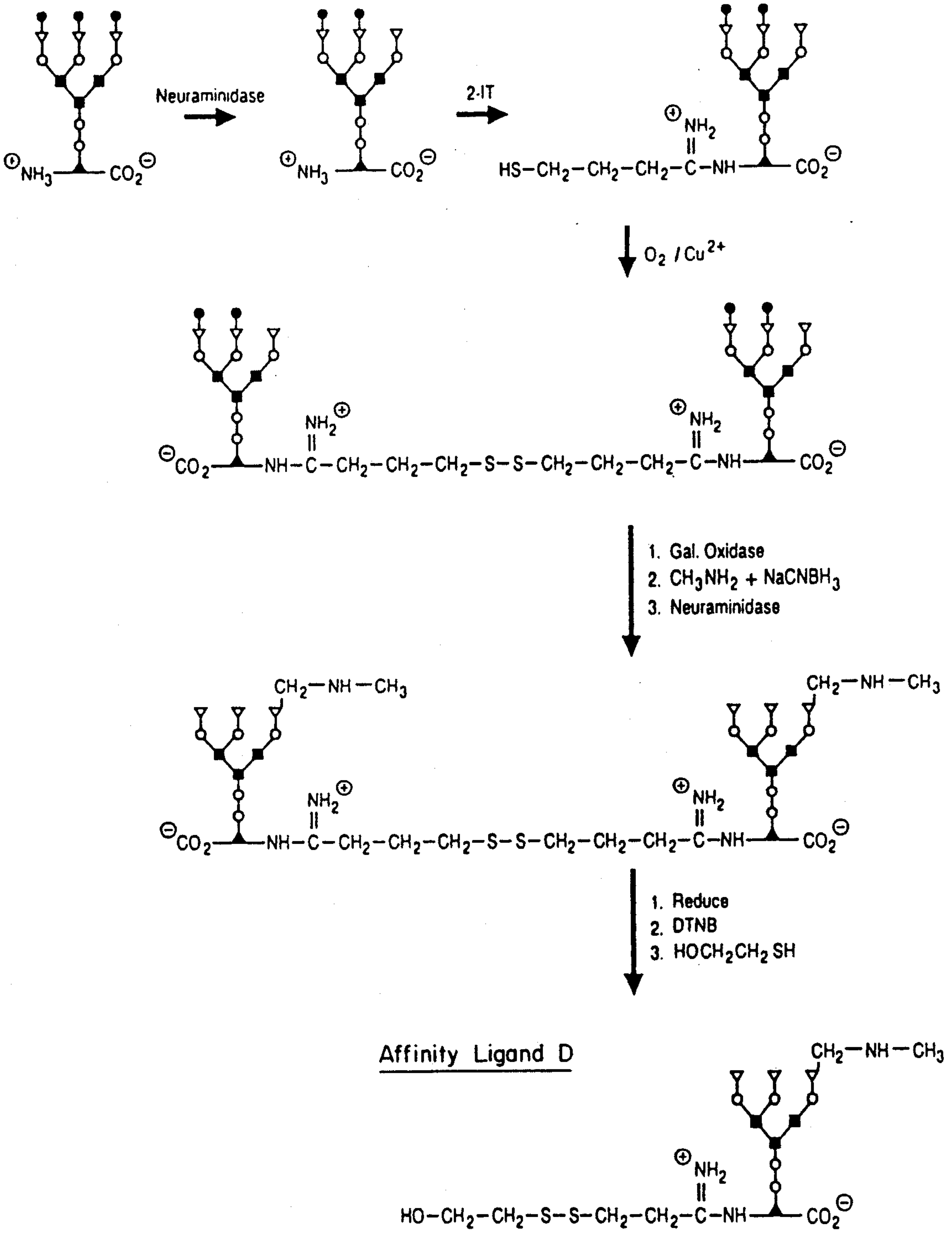
FIG. 6 illustrates the scheme for the synthesis of affinity ligand D described in Example 5.

Preparation of Affinity Ligand D (See FIG. 6)

Preparation of N-glycosidically-linked Glycopeptide From Fetuin

Glycopeptides were purified as in Example 1.

Synthesis of Affinity Ligand D From Glycoceptide Derived From Fetuin

The steps in this synthesis of affinity ligand D are illustrated in FIG. 6.

Partial Removal of Sialic Acid From the Glycopeptide By Enzymic Hydrolysis With Neuraminidase This step was performed as described for the partial removal of sialic acid in the preparation of affinity ligand C in Example 4.

Reaction of the α-amino Group of the Partially Desialated Glycopeptide With 2-iminothiolane and Disulfide Dimerization This step was performed as described for the chemical modification of the α-amino group of the partially desialated glycopeptide in the preparation of affinity ligand C in Example 4.

Oxidation of Partially Desialated Disulfide-linked Dimeric Glycopeptide Using Galactose Oxidase This step was performed as described in the preparation of affinity ligand C in Example 4.

Reductive Amination of Oxidized, Partially Desialated Disulfide-linked Dimeric Glycopeptide This step was performed as described in the preparation of affinity ligand C in Example 4.

Complete Removal of Sialic Acid From Partially Desialated Disulfide-linked , Dimeric Glycoceptide Containing Galactosamine (MADG)

This step was performed as described in the preparation of affinity ligand A in Example 1.

Reduction of Disulfide-linked Dimeric Glycopeptide Containing MADG and Reaction of the Thiol Group So Generated with 5,5'-dithiobis(2-nitrobenzoic Acid)

Glycopeptide dimer (20 mM) was adjusted to pH 8 by the addition of triethanolamine base, and EDTA was added to 20 mM final concentration. Solid dithiothreitol was added to 0.4M final concentration and the solution incubated for 16 hours at 37° C. The reduced glycopeptide was purified by gel filtration through a column of Sephadex G-50 (Fine) equilibrated in 5 mM sodium acetate buffer, pH 4.7, containing NaCl (50 mM) and EDTA (5 mM). The fractions containing glycopeptide were pooled and assayed for hexose and sulfhydryl groups to ensure that the reduction was complete (about 1.0 sulfhydryl group per mole of glycopeptide).

The reduced sulfhydryl-containing glycopeptide was then reacted with 5,5'-dithiobis(2-nitrobenzoic acid). The glycopeptide pool (3 mM in glycopeptide) in pH 4.7 sodium acetate buffer (above paragraph) was placed in a dropping funnel, and allowed to drip into seven volumes of a rapidly stirring buffer of 10 mM triethanolamine-HCl, pH 7.8, containing 5,5'-dithiobis(2-nitrobenzoic acid) (40 mM) and EDTA (0.5 mM) at ambient temperature under an atmosphere of argon. The solution was stirred for 70 min and then acetic acid (1.14% v/v) was added and the solution chilled to 0° C. The pH was then titrated down to 2 using 1M HCl, during which a pale yellow precipitate formed. The precipitate was removed by filtration and washed with water.

The supernatant fraction and washings were concentrated by rotary evaporation and applied to a column of Sephadex G-25 (Fine) equilibrated in 0.1M pyridine-acetate, pH 5.4, in order to purify the glycopeptide from excess reagents. The glycopeptide was assayed using the hexose assay while 5-thio-2-nitrobenzoate groups incorporated into the glycopeptide were measured by the method of Ellman (cited above in Example 3). The glycopeptide was recovered by rotary evaporation and lyophilization from water in the usual way (described in Examples 1, 2, and 3).

Exchange of the Mercaptonitrobenzoate Group With Mercaptoethanol to Yield Affinity Ligand D The mercaptonitrobenzoate-derivative of the affinity ligand was dissolved in 0.25M triethanolamine-HCl buffer, pH 7.4, containing NaCl (0.25M) and EDTA (5 mM), to give a solution with a final concentration of 13 mM glycopeptide ligand. 2-mercaptoethanol was added to give 1.1 equivalents relative to glycopeptide ligand. After 30 minutes at ambient temperature, the reaction mixture was applied to a column of Sephadex G-50 (Fine) equilibrated in 0.1M pyridine-acetate pH 5.4, in order to purify affinity ligand D from excess reagents and the thionitrobenzoate ion. The glycopeptide was identified in the fractions by the hexose assay and recovered by pooling fractions, rotary evaporation and lyophilization from water, to yield affinity ligand D.

The disulfide exchange reaction is also carried out with the activating group on the 2-mercaptoethanol. In this case the reduced glycopeptide ligand is mixed with a slight molar excess of activated 2-mercaptoethanol and purified in the usual way. Examples of activated mercaptoethanols include 2-(2'-pyridyldithio)ethanol and 5-hydroxyethyldithio-2-nitrobenzoic acid.

Alternative Variation for the Preparation of Affinity Ligand D Derived From Fetuin Partial removal of sialic acid from glycopeptide by enzymic hydrolysis with neuraminidase was performed as described for the partial removal of sialic acid in the preparation of affinity ligand C in Example 4. Reaction of the α-amino Group of the Partially Desialated Glycopeptide With 2-iminothiolane, Reduction With Borohydride and Derivatization of Free Sulfhydryl Groups With 2-(2'-pyridyldithio)ethanol.

Partially desialated glycopeptide (85 μmol) was dissolved in 0.2M triethanolamine-HCl buffer, pH 8, (0.85 mL), containing EDTA (20 mM). Then solid 2-iminothiolane-HCl (0.85 mmol) was added. The mixture was stirred until all the 2-iminothiolane-HCl had dissolved and the pH was adjusted to 8 by addition of NaOH (from a 10.0M solution). The solution was stirred at ambient temperature for 24 hours. The solution was diluted to a final volumne of 5 mL with deionized water and solid $NaBH_4$ (6.55 mmoles) was added. The solution was then stirred at ambient temperature overnight. Glacial acetic acid was added slowly to the stirring solution until the pH was 5 (requires about 0.44 mL of acetic acid). The reaction mixture was then mixed with a solution (33 mL) of 2-(2'-pyridyldithio)ethanol (35 mM) in 5mM sodium acetate buffer, pH 4.7, containing NaCl (50 mM) and EDTA (1 mM). The solution was stirred at ambient temperature for 5 hours, a time period sufficient to assure completion of the reaction of free sulfhydryl groups with 2-(2'-pyridyldithio)ethanol. The mixture was then deionized by the addition of 40 g of mixed bed ion exchange resin (AG 501-X8, 20-50, mesh, Bio-Rad. Richmond, Calif.) and mixed at ambient temperature for 10 minutes. The resin was removed by filtration with the filtrate set aside and saved. The resin was washed with deionized water and the wash was combined with the filtrate. The resulting solution (245 mL) was applied to a column (70 mL) of DEAE-cellulose (DE-52; acetate form, equilibrated in water). The column was washed with 2 column volumes of water and the glycopeptide was eluted with 0.5M sodium acetate, pH 4.5 (yield, 61.5 μmoles). The pooled fractions were deionized by adding 1.2 g of the same mixed-bed ion-exchange resin (AG 501-X8) per mL of solution, mixing for 10 minutes at ambient temperature and then filtering to remove the resin from the filtrate. The resin was washed with deionized water, the wash was combined with the filtrate and the glycopeptide solution was dried by rotary evaporation.

The dry ligand is dissolved in 0.1M sodium phosphate buffer, pH 7. The ligand is oxidized with galactose oxidase, reduced and aminated with methylamine and $NaCNBH_3$ and sialic acids are removed with neuraminidase as described above in the first variation in the preparation of affinity ligand D. These steps yield affinity ligand D.

Activation of Affinity Ligand D With Cyanuric Chloride

All steps were conducted at ambient temperature. The affinity ligand D was dissolved in water (one volume) to give a 10 mM solution. Three volumes of 0.5M triethanolamine-HCl buffer, pH 8, containing 0.5M β-methylgalactoside were added to the solution. Dioxane was dried by passing through a column of alumina and 8 volumes of the dry dioxane were added to the ligand solution. The mixture was stirred rapidly at ambient temperature and 0.5 volumes of 1M cyanuric chloride (freshly prepared in dry dioxane) was added. After stirring for one minute, 1 volume of glacial acetic acid was added to the mixture. Dioxane was removed by rotary evaporation and the solution was filtered through glass wool to remove a slight precipitate. The activated affinity ligand D was then purified from excess reagents by gel filtration through a column of Sephadex G-25 (Fine) equilibrated in 20 mM $NaH_2PO_4$-HCl buffer, pH 3. Fractions containing ligand were pooled for use in blocking ricin (or abrin).

The affinity ligand D is also activated by 2,4-dichloro-6-methoxytriazine using the same conditions except that the incubation time is extended from 1 minute to 15 minutes.

EXAMPLE 6

Figure 7:
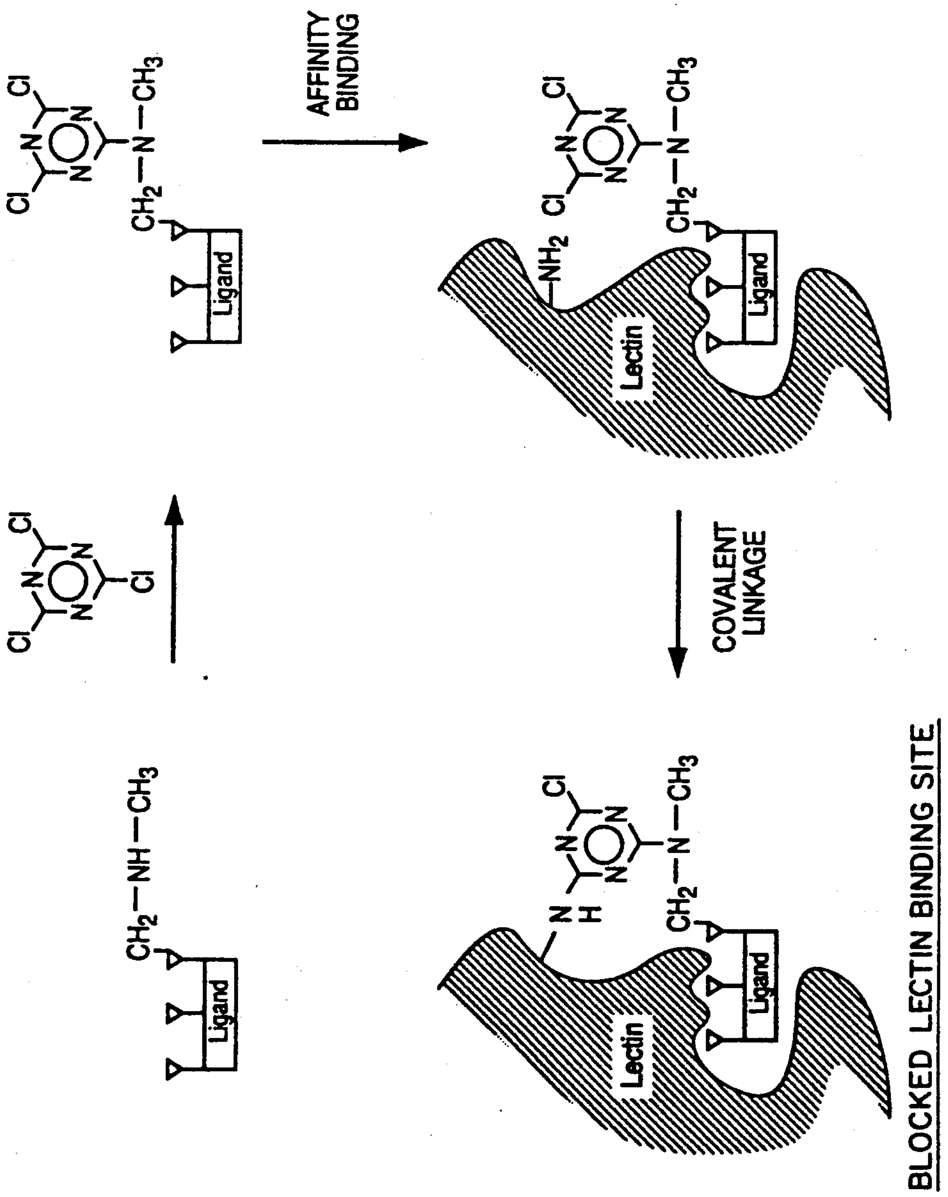
FIG. 7 illustrates the activation of affinity ligands A, B, C and D and the reaction of the activated ligand with an oligosaccharide-binding site of a lectin.

Preparation and Purification of Blocked Ricin (See FIG. 7)

Reaction of Ricin With the Activated Affinity Ligands A, B, C or D

Ricin (2 mg/mL, Sigma) in 10 mM potassium phosphate buffer, pH 7, containing NaCl (145 mM) was mixed, at 25° C. with a volume of the activated affinity ligand dissolved in 20 mM sodium phosphate-HCl buffer or, less preferably in 50 mM potassium phosphate buffer, pH 3. In different experiments, the molar ratio of ricin, ligand ranged from 1:1 to 1:20. The pH of the solution (ricin concentration of 0.4-1.0 mg/mL in different experiments) was then adjusted to pH 8 by addition of 1.0M triethanolamine base while stirring the solution continuously. The reaction was allowed to proceed at 25° C. for about 16-24 hours, preferably for 16-160 hours. The reaction was terminated by adding one-tenth volume of 1.0M ethanolamine-HCl, pH 8, and continuing the incubation for a further 20 hours.

The reaction of ricin with affinity ligands activated by 2,4-dichloro-6-methoxytriazine was performed under similar conditions except that the pH was increased to 8.6 and the incubation time at 25° C. was increased to 2-4 days, preferably from 2-10 days.

Purification of Blocked Ricin

The reaction mixture containing blocked ricin, unreacted affinity ligand and unreacted ricin was dialyzed exhaustively against phosphate-buffered saline (10 mM potassium phosphate, pH 6.8, containing 145 mM NaCl). Alternatively, the reaction mixture was applied to a column of BioGel P-60 (Fine) equilibrated in 0.1M sodium acetate buffer, pH 4, containing lactose (0.1M) and EDTA (1 mM). The protein peak (ricin) was collected and dialyzed exhaustively against phosphate-buffered saline to remove lactose. Most of the non-blocked ricin was then removed from the preparation by passing the dialyzed protein through a column of immobilized lactose (polyacrylamide beads containing lactose; Pierce Chem. Co.) that was equilibrated in phosphate-buffered saline, pH 6.8. A column volume of 1 mL per 1 mg of ricin was used. Acid-treated cross-linked Sepharose 6B (Pharmacia. Uppsala, Sweden), prepared as described by Ersson et al., *Biochim. Biophys. Acta* 310, 446-452 (1973), may be substituted for immobilized lactose. Blocked ricin was collected in the eluate while loading the column and then washing with 1.5 column volumes of phosphate-buffered saline. The preparation of blocked ricin was then concentrated to 2-5 mg/mL and applied to a column of immobilized asialofetuin at 25° C. The asialofetuin (enzymically prepared by Sigma) was immobilized by reaction of the glycoprotein with carbonyldiimidazole-activated TSK beads (Reacti-Gel HW-65F, from Pierce Chemical Co.) according to the method of Bethell et al., *J. Biol. Chem.* 254, 2572-2574 (1979). The resulting asialofetuin-TSK beads could bind about 2-3 mg of ricin per mL of gel. Other supports can be used to covalently link asialofetuin, including agarose, (e.g., carbonyl diimidazole-activated agarose from Pierce Chemical Co., or AffiGel 10 or 15 from Bio-Rad). The volume of the column was 1 mL per 1 mL of blocked ricin solution. The blocked ricin was collected in the eluate while loading the column and then washing with 1.5 column volumes of phosphate-buffered saline. The ricin which did not bind was considered blocked because it had been shown that ricin binds as tightly to asialofetuin as to cell surfaces (Sandvig et al., *Eur. J. Biochem.* 88, 307-313 (1978)).

Purification of Blocked Ricin By Use of an Anti-ricin Affinity Column to Remove Traces of Ricin Anti-ricin Monoclonal Antibody The P2G8 hybridoma secretes a murine $IgG_1$ which recognizes both ricin A-chain and native (unmodified) ricin. This hybridoma is available from the Dana-Farber Cancer Institute, Boston, Mass. It was derived using the standard techniques for the derivation of hybridomas secreting murine antibodies, Köhler et al., *Eur. J. Imm. 6, 511-519 (*1976) and Goding, *J. Imm. Meth.* 39, 285-308 (1980). In brief, a BALB/c mouse, which had been immunized subcutaneously three times with 10 μg of purified A-chain (obtained from Worthington, Freehold. N.J.) emulsified in complete Freund's adjuvant, was used as a source of splenocytes. These splenocytes were fused with the non-secreting, HGPRT-negative BALB/c myeloma, NS-1 (ATCC TIB 18) in the presence of polyethylene glycol using the standard techniques (Kohler et al, and Goding, cited above). Hybridomas were selected in the presence of medium containing hypoxanthine, thymidine and aminopterin as described by Goding (cited above). When clones of cells were visible (about 7-14 days postfusion), the supernatants of wells containing clones were screened for production of murine antibody which reacted with ricin A-chain in a solid-phase radioimmunoassay which was performed using standard procedures (Hunter in "Handbook of Experimental Immunology" (Weir, ed.) Vol. 3, Chap. 14 (1978)). Approximately 30 such hybridomas were obtained, of which about 20 also reacted with whole ricin. No hybridoma antibody bound bovine serum albumin or gelonin. P2G8 was selected for further study because of its high production of antibody. It was grown in pristane-primed BALB/c mice and the $IgG_1$ antibody was purified from the resulting ascites fluid of these mice by the same procedure as described for purification of anti-B4 (also an $IgG_1$) in Example 11 below.

Preparation of Anti-ricin Antibody-TSK Gel

P2G8 antibody (22 mg) in 7 mL of PBS (phosphate-buffered saline, pH 7.2, was mixed with 2 mL (packed bead volume) of 1,1'-carbonyldiimidazole-activated Fractogel TSK HW-65 F (from Pierce Chemical Company, "Reacti-Gel HW-65 F"). Solid $K_2CO_3$ and NaCl was added to give a final concentration of 1M $K_2CO_3$ and 0.5M NaCl. The suspension was mixed by gentle rotation for 24 hours at 25° C. Ethanolamine was then added to give a 0.1M final concentration and rotation continued for a further 24 hours at 25° C. The beads were then spun down and the supernatant removed. The beads were washed extensively with PBS to remove non-covalently bound antibody. Most of the antibody (97%) wa linked to the beads. Experiments with radiolabelled ricin showed that a P2G8-affinity column containing the P2G8-TSK beads could bind about 0.5 mg ricin/mL gel. The ricin could be eluted from the gel with 0.1M acetic acid, pH 3, containing 0.15M NaCl. The P2G8-affinity column did not bind ricin in the presence of 0.2M lactose, and did not bind blocked ricin. Thus, the immobilized antibody will only bind ricin in the absence of sugar ligand and can be used to remove traces of native ricin from preparations of blocked ricin.

Purification of Blocked Ricin Using P2G8-TSK Affinity Chromatography

Blocked ricin (2 mg) in 7 mL of PBS, pH 6.8 was passed through a column (1.5 mL bed volume) of P2G8-TSK beads at a flow rate of 2.5 mL/h at 4° C. The blocked ricin eluted from the column without being retained. The column could be reused after washing it with 0.1M acetic acid, pH 3containing NaCl (0.15M) and lactose (0.1M) before reequilibration in PBS, pH 6.8.

Purification of Blocked Ricin by Ion-exchange Chromatography

Blocked ricin can be purified from non-blocked ricin by ion-exchange chromatography using classical techniques for purifying proteins by ion-exchange chromatography that are well-known in the art (see, for example, Scopes, "Protein Purification, Principles and Practice" Springer-Verlag, N.Y. (1982)).

Determination of the Number of Affinity Ligands Covalently Bound to the Blocked Ricin In order to measure quantitatively the number of covalently bound ligands required to react with ricin to achieve blocked ricin, the reaction between ricin and the activated affinity ligand was carried out using radioactively labelled ligand. Radiolabelled ligand was readily synthesized by alkylating the sulfhydryl group introduced at the α-amino group of the glycopeptide.

Preparation of Radiolabelled Affinity Ligand

Affinity ligand B, C or D (2.5 μmoles) in 0.2M triethanolamine-HCl buffer, pH 8 (2 mL) was degassed and equilibrated in an atmosphere of nitrogen. Freshly prepared dithioerythritol (5 μmoles in 50 μL water) was added and the solution was stirred for 60 min, at 25° C. under nitrogen. Then 15 μmoles of iodo(1-$^{14}$C)acetamide (15 μCi from Amersham) diluted to 1 μCi/μmol with non-radioactive iodoacetamide before use) was added to the solution in 0.75 mL of water, and the solution was stirred for 15 hours at 25° C. under nitrogen in the dark. One drop of 2-mercaptoethanol was added to quench the reaction and then the solution was applied to a column (80 mL) of BioGel P-6 (Fine) equilibrated in 100 mM pyridine-acetate buffer, pH 5, for purification of the radiolabelled glycopeptide by gel filtration. Fractions containing glycopeptide were combined and solvent removed by rotary evaporation and lyophilization. The radiolabelled ligand was dissolved in 0.5 mL water and portions taken for measurement of radioactivity by scintillation counting and for measurement of ligand concentration by assay for hexose. The specific activity was 2220 cpm/nmol.

Reaction of Ricin With Radiolabelled Ligand

The radiolabelled ligand was activated with cyanuric chloride using the same conditions as described for affinity ligand A in Example 1. The activated radiolabelled ligand was reacted with ricin at a ligand, ricin ratio of 4:1 using the same conditions as described above in this Example 6. The blocked ricin was purified by the same procedure as described above in this section.

The radioactivity found in the preparation of blocked ricin that was made in this way corresponded to about 2 moles of ligand incorporated per mole of ricin. Some of the ricin was retained by the column of immobilized asialofetuin and could be eluted by including lactose (50 mM) in the elution buffer. This material was found to have only about 1 mole of radiolabelled ligand incorporated per mole of ricin. Toxicity tests (see Example 30) showed the material to be very cytotoxic, with a toxicity that was only 10-fold less than that of non-blocked ricin. The evidence indicates that ricin has two binding sites for the affinity glycopeptide ligand, and that both sites must be blocked in order to prevent ricin from binding to cell surfaces (and to immobilized asialofetuin). If ricin retains the ability to bind to cells, then these cells will be killed by low concentrations of ricin.

EXAMPLE 7

Preparation and Purification of Blocked Abrin

Reaction of Abrin With Activated Affinity Ligand C

Abrin (Sigma Chemical) was dialysed into 50 mM triethanolamine-HCl buffer, pH 8. Affinity ligand C. activated as described in Example 4, in 50 mM of sodium phosphate-HCl buffer, pH 3, was added to the abrin solution (3.25 mg/mL) in a 4-fold molar excess. The pH of the solution was adjusted to pH 8 by the addition of 1.0M triethanolamine base while stirring the solution continuously. The reaction was allowed to proceed for 24 hours at 25° C. and then one-tenth volume of 1.0M ethanolamine-HCl, pH 8, was added and incubation at 25° C. continued for a further 24 hours.

2.4-dichloro-6-methoxytriazine is used to activate the affinity ligand C in place of cyanuric chloride as described in Example 4, in which case the pH of the abrin-ligand mixture is increased to 8.6, and the incubation time is extended to 2–4 days.

Purification of Blocked Abrin

Blocked abrin was purified from unreacted abrin and excess affinity ligand by using the same procedure as described in Example 6 for ricin.

Abrin was also blocked using a radiolabelled affinity ligand in analogous experiments to those described for ricin in Example 6. As for ricin, these experiments showed that abrin required two affinity ligands to be covalently bound to the protein in order to block binding of abrin to immobilize asialofetuin.

EXAMPLE 8

Conjugation of Antibody J5 (Anti-Calla) to Blocked Ricin (Blocked With Affinity Ligand A)

Monoclonal Antibody J5

J5 is a murine $IgG_{2a}$ antibody that is specific for the Common Acute Lymphoblastic Leukemia Antigen (CALLA) and is described by Ritz et al., *Nature* 283, 583–585 (1980). The antibody was produced by growing hybridoma cells as ascites tumors in BALB/c mice. The mAb was purified by affinity chromatography using protein A-Sepharose CL-4B and by cation-exchange chromatography with carboxymethylcellulose according to the procedure described in Goldmacher et al., *J. Imm.* 136, 320–325 (1986). The antibody is commercially available from Coulter Immunology, Hialeah. Fla.

Modification of J5 With 2-iminothiolane

J5 antibody (2 mg/mL) in 60 mM triethanolamine-HCl buffer, pH 8, containing potassium phosphate (5 mM). NaCl (100 mM) and EDTA (1 mM) was degassed and then treated with 2-iminothiolane (0.25 mM) for 90 minutes at 0° C. under an atmosphere of nitrogen. The stock solutions of 2-iminothiolane (hydrochloride salt obtained from Pierce Chemical Co.) were prepared as described previously by Lambert et al., *Biochem.* 17, 5406–5416 (1978). The reaction was terminated and the excess reagent removed by filtration at 4° C. through a column of Sephadex G-25 (Fine) equilibrated with 5 mM bis/tris-acetate buffer, pH 5.8, containing NaCl (50 mM) and EDTA mM). Sulfhydryl groups introduced into the antibody in this way were quantified spectrophotometrically by the method of Ellman, *Arch Biochem. Biophys.* 82, 70–77 (1959). This procedure results in about 1.3 sulfhydryl groups per molecule of antibody.

Modification of Blocked Ricin (Blocked Using Affinity Ligand A)

Blocked ricin (0.26 mg/mL) in 45 mM sodium phosphate buffer, pH 7, containing NaCl (100 mM) and EDTA (0.5 mM) was warmed to 30° C. Then, 1 mg of SMCC, from Pierce Chemical Co., was added per mL of blocked ricin solution, from a stock solution in dry dioxane (70 mg/mL). The SMCC was added in 4 equal portions (0.25 mg per mL of blocked ricin solution) with a 10 minute incubation at 30° C. after each addition. After the final addition, the protein solution was incubated for 30 minutes at 30° C. and then the modified blocked ricin was purified by gel filtration through a column of BioGel P-6 (Fine) equilibrated in 40 mM sodium phosphate buffer, pH 7. Maleimido groups introduced into blocked ricin were quantified by the method described by Lambert et al., *J. Biol. Chem.* 260, 12035–12041 (1985). About 1.0 group per molecule of blocked ricin was introduced by this procedure.

Conjunction of Modified J5 With Modified Blocked Ricin

Modified J5 (3.3 mg in 13 mL of pH 5.8 buffer as described above) was mixed at 4° C. with modified blocked ricin (0.73 mg in 7.2 mL of pH 7 buffer as described above). The pH of the mixture was raised to pH 7 by adding 0.13 mL of 0.5M triethanolamine base. The mixture was incubated for an additional 2 hours at 4° C. Then 2-mercaptoethanol (10 $\mu$M) was added to block any unreacted maleimido groups, and after 15 minutes at 25° C., iodoacetamide (2 mM) was added to block any unreacted sulfhydryl groups by incubation for 60 minutes at 25° C.

Purification of J5-blocked Ricin Conjugate

The above conjugation reaction mixture was applied to a column (1 mL) of concanavalin A-Sepharose (Sigma Chemical Co.) at a flow rate of 2 mL/h at 25° C. The column was then washed with 20 mL of 10 mM potassium phosphate buffer, pH 7.2, containing NaCl (145 mM) (PBS). Antibody J5 does not bind to concanavalin A and is removed by washing. Blocked ricin and the J5-blocked ricin conjugate were eluted from the column with PBS containing N-methyl mannoside (1.0M) at a flow rate of 1 mL/h at 25° C.

This mixture was applied to a column (1 mL) of protein A-Sepharose CL-4B equilibrated in PBS containing α-methyl mannoside (1.0M) at 4° C. The column was washed with the same buffer (5 mL) and then with PBS (15 mL) which removes all non-conjugated blocked ricin that does not bind to protein A. The J5-blocked ricin conjugate was eluted from the column with 0.1M acetic acid containing NaCl (0.15M). The protein was neutralized immediately with one-tenth volume of $NaHCO_3$ (1.0M) and was dialyzed into PBS. The conjugate (yield of 28% with respect to blocked ricin) was frozen in liquid nitrogen in small aliquots (200 μL), and stored at −70° C.

EXAMPLE 9

Conjugation of J5 to Blocked Ricin (Blocked With Affinity Ligand C) Using a Disulfide Linker Monoclonal Antibody J5 mAb J5 was purified as described in Example 8.

Modification of J5

J5 was modified with 2-iminothiolane as in Example 8, to introduce about 1.5 sulfhydryl groups per molecule of antibody.

Conjugation of Modified J5 with Blocked Ricin, Blocked Using Affinity Ligand C

Modified J5 containing free sulfhydryl groups (5 mg) in 8 mL of 5 mM bis/tris-acetate buffer, pH 5.8, containing NaCl (50 mM) and EDTA (1 mM) was mixed at 4° C. with blocked ricin (1 mg in 1.3 mL of PBS) that had been blocked using activated affinity ligand C. This affinity ligand contained a pyridyldisulfide group that was still present in the blocked ricin. This group reacts with the sulfhydryl groups that were introduced into antibody J5 by modification with 2-iminothiolane, resulting in the linkage of J5 and blocked ricin by a bond cleavable by reduction. The pH of the reaction mixture was adjusted to 7 by adding 0.08 mL of 0.5M triethanolamine-HCl buffer, pH 8, and then incubated for 48 hours at 4° C. Finally, iodoacetamide (5 mM) was added to block any remaining sulfhydryl groups.

Purification of J5-blocked Ricin (Disulfide-linked) Conjugate

The non-conjugated blocked ricin was removed from the reaction mixture by gel filtration through a column of BioGel A-1.5m as described in Example 15, except the buffer used consisted of 10 mM HEPES, pH 7.5, containing NaCl (0.5M), lactose (10 mM) and $NaN_3$ (0.05% w/v).

The non-conjugated antibody was removed from the J5-blocked ricin conjugate by using a column of immobilized concanavalin A as described in Example 8. The purified conjugate was finally dialyzed against PBS. The conjugate was placed in 200 μL aliquots which were frozen in liquid nitrogen and stored at −70° C.

EXAMPLE 10

Conjugation of Antibody J5 to Blocked Abrin (Blocked With Reduced and Alkylated Affinity Ligand C)

Monoclonal Antibody J5

Monoclonal antibody J5 was purified as described in Example 8.

Modification of J5 With SMCC

J5 antibody was modified with SMCC as described for modifying anti-B4 in Example 15, except that the antibody concentration was 2.2 mg/mL and the SMCC concentration was 135 μM. About 1.5 maleimido groups were introduced per molecule of monoclonal antibody J5 in this set of experiments.

Modification of Blocked Abrin

When there is no reactive group on the blocked abrin, as when affinity ligand A is used to block the binding sites of the lectin portion of abrin, or, as in this Example, when affinity ligand C is first reduced and the resulting sulfhydryl group is alkylated by reaction with iodoacetamide prior to its use in preparing blocked abrin, the blocked abrin must be modified with a cross-linking reagent in order to provide a reactive group for conjugation with antibody.

Blocked abrin (0.4 mg/mL) in 50 mM triethanolamine-HCl buffer, pH 8, containing EDTA (0.5 mM) was mixed with 2-iminothiolane (2.5 mM) and incubated for 90 minutes at 0° C. under an atmosphere of nitrogen. Stock solutions of 2-iminothiolane were prepared as referenced in Example 8. The reaction was terminated by removing excess reagent by gel filtration over a column of BioGel P-6 (Fine) equilibrated with 50 mM potassium phosphate buffer, pH 7, containing EDTA (1 mM). These conditions resulted in the incorporation of about 1.0 sulfhydryl group per molecule of blocked abrin, as determined by the method of Ellman (cited above. Example 8).

Conjugation of Maleimido-modified J5 With Sulfhydryl-modified Blocked Abrin

Modified J5 (4.5 mg) in 3.5 mL of 0.05M potassium phosphate buffer, pH 7, containing EDTA (1 mM) was mixed at 4° C. with modified blocked abrin (1 mg) in 4.8 mL of the pH 7 buffer. The mixture was incubated for 24 hours and then iodacetamide (2 mM) was added to block any remaining sulfhydryl groups in an overnight incubation at 4° C.

Purification of J5-blocked Abrin Conjugate

The conjugate was concentrated by dialysis against polyethylene glycol. Following dialysis, the solution was submitted to gel filtration through a column of BioGel A-1.5m and then was subjected to an affinity purification over a column of immobilized concanavalin A. as described for the anti-B4-blocked ricin conjugate in Example 15.

The purified conjugate, which was obtained in about 20% yield relative to the amount of blocked abrin, was finally dialyzed against PBS. The conjugate was placed into small aliquots (200 μL) and then quickly frozen in liquid nitrogen. The samples of antibody-lectin conjugate were stored at −70° C.

EXAMPLE 11

Purification of Antibody Anti-B4

Monoclonal antibody anti-B4 is commercially available from Coulter Immunology. Hialeah, Fla. All succeeding steps of this example were carried out at 4° C. Ascites fluid, drawn from BALB/c mice carrying the hybridoma cells, was fractioned with $(NH_4)_2SO_4$. The protein that precipitated in the fraction from 0–50% saturation was dissolved in PBS with stirring and then dialysed into 0.1M Tris-HCl buffer, pH 8.9, containing NaCl (3.0M).

The resulting solution was applied to a column of protein A-Sepharose CL-4B equilibrated in the pH 8.9 buffer described above. The column was washed with this buffer until the protein concentration in the eluate was close to zero. Then the monoclonal antibody was eluted from the column with a buffer consisting of 0.05M $K_2HPO_4$ that was adjusted to pH 6 with acetic acid and which contained NaCl (100 mM).

If the antibody was to be used in a conjugation reaction where the resulting conjugate was to be purified by affinity chromatography using a column of immobilized concanavalin A (for example see Example 12), the antibody preparation was then adjusted to pH 7 by titration with $Na_2HPO_4$ and passed over the immobilized lectin (for example, concanavalin A-agarose from Sigma Chemical Co.) that was equilibrated in 0.13M sodium phosphate buffer, pH 7, containing NaCl (0.15M). Before use, columns of concanavalin A-agarose were washed as described by Lambert et al, in "Immunotoxins" (Frankel, ed.) pp. 323-348. Kluwer Acad. Publ., Boston (1988).

The fraction of antibody that was not retained by the column was then dialyzed into 50 mM sodium acetate buffer, pH 5. Following dialysis the solution was then applied to a column of S-Sepharose (fast flow; Pharmacia) that was equilibrated in the same buffer. The antibody was eluted using a NaCl buffer at pH 5 (0-0.5M).

The antibody so purified was judged pure by sodium dodecyl sulfate-polyacrylamide gel electrophoresis (SDS-PAGE) and by isoelectrofocusing, techniques that are described in Goldmacher et al., *J. Imm.* 136, 320-325 (1986).

The concanavalin A-column purification step is omitted if concanavalin A-affinity chromatography is not to be used in conjugate purification (Example 21, for example).

EXAMPLE 12

Conjugation of Anti-B4 to Blocked Ricin (Blocked With Affinity Ligand A)

Modification of Anti-B4 With 2-iminothiolane

Antibody B4 (2 mg/mL) in 60 mM triethanolamine-HCl buffer, pH 8, containing potassium phosphate (6 mM), NaCl (90 mM) and EDTA (1 mM) was degassed and then treated with 2-iminothiolane (3.0 mM) for 30 minutes at 0° C. under an atmosphere of nitrogen. Stock solutions of 2-iminothiolane (hydrochloride salt obtained from Pierce Chemical Co.) were prepared as described previously by Lambert et al., *Biochem.* 17, 5406-5416 (1978). The reaction is terminated and the excess reagent removed by gel filtration at 4° C. through a column of Sephadex G-25 (Superfine) equilibrated with 5 mM bis/tris-acetate buffer, pH 5.8, containing NaCl (50 mM) and EDTA (1 mM). Sulfhydryl groups introduced into the antibody in this way were quantified spectrophotometrically by the method of Ellman. *Arch Biochem. Biophys.* 82, 70-77 (1959) this procedure resulted in about 1.8 sulfhydryl .groups per molecule of antibody.

Modification of Blocked Ricin (Blocked Using Affinity Ligand A)

Blocked ricin (0.26 mg/mL) in 45 mM sodium phosphate buffer, pH 7, containing NaCl (100 mM) and EDTA (0.5 mM) was warmed to 30° C. Then. 1 mg of SMCC, from Pierce Chemical Co., was added per mL of blocked ricin solution, from a stock solution in dry dioxane (70 mg/mL). The SMCC was added in 4 equal portions (0.25 mg per mL of blocked ricin solution) with a 10 minute incubation at 30° C. after each addition. After the final addition, the protein solution was incubated for 30 minutes at 30° C. and then the modified blocked ricin was purified by gel filtration through a column of BioGel P-6 (Fine) equilibrated in 40 mM sodium phosphate buffer, pH 7. Maleimido groups introduced into blocked ricin were quantified by the method described by Lambert et al., *J. Biol. Chem.* 260, 12035-12041 (1985); about 1.0 group per molecule of blocked ricin was introduced by this procedure.

Conjugation of Modified Anti-B4 With Modified Blocked Ricin

Modified anti-B4 (3.3 mg in 13 mL of pH 5.8 buffer as described above) is mixed at 4° C. with modified blocked ricin (0.73 mg in 7.2 mL of pH 7 buffer as described above). The pH of the mixture is raised to 7 by the addition of 0.13 mL of 0.5M triethanolamine base. The mixture is incubated at 4° C. for 2 hours. Then to block any unreacted maleimido groups, 2-mercaptoethanol (10 μM) is added and after 15 minutes at 25° C. iodoacetamide (2 mM) is added to block any unreacted sulfhydryl groups by incubation for 60 minutes at 25° C.

Purification of Anti-B4-blocked Ricin Conjugate

The above conjugation reaction mixture is applied to a column (1 mL) of concanavalin A-Sepharose (Sigma Chemical Co.) at a flow rate of 2 mL/h at 25° C. The column is then washed with 20 mL of 10 mM potassium phosphate buffer, pH 7.2, containing NaCl (145 mM) (PBS). Antibody anti-B4 does not bind to concanavalin A and is removed by washing. Blocked ricin and the anti-B4 blocked ricin conjugate are eluted from the column using a buffer of PBS containing methyl α-D-mannopyranoside (1.0M) at a flow rate of 1 mL/h at 25° C.

The mixture of conjugate and blocked ricin is then dialyzed into 0.1M Tris-HCl buffer, pH 8.9, containing NaCl (3.0M). After equilibration, the protein-containing solution is applied to a column containing protein A-Sepharose CL-4B equilibrated in the high-salt pH 8.9 buffer at 4° C. (1 mL column for this quantity of conjugate). The column is then washed with 5-10 column volumes of high-salt pH 8.9 buffer which removes all the non-conjugated blocked ricin that does not bind to protein A.

The conjugate is then eluted from the column with 50 mM $K_2HPO_4$ adjusted to pH 6 with acetic acid. The conjugate is then dialyzed into PBS. Finally, the conjugate is frozen in liquid nitrogen in small aliquots (200 μL), and is stored at −70° C.

EXAMPLE 13

Figure 8:
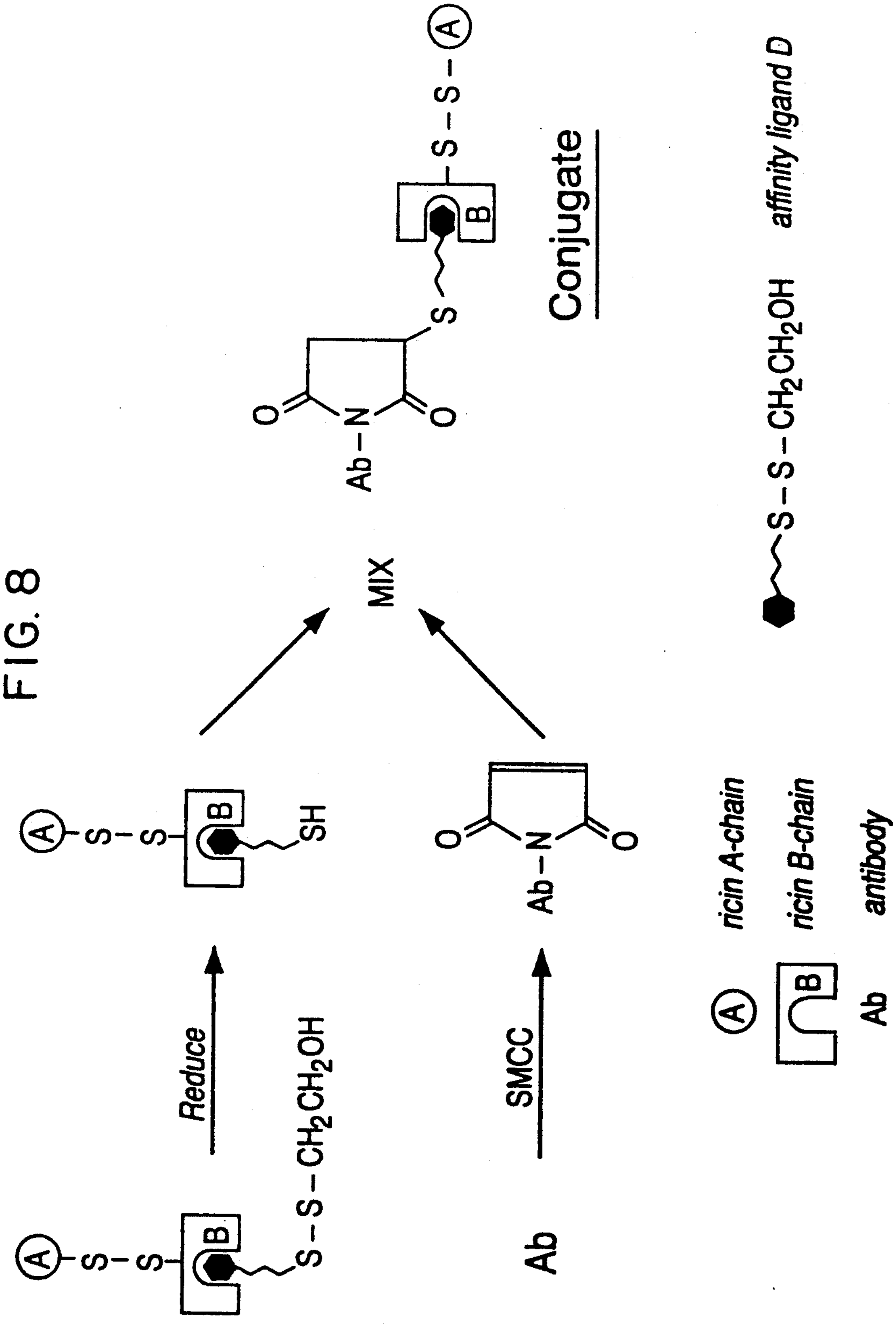
FIG. 8 illustrates an example of the preparation of a conjugate between an antibody and blocked ricin (blocked with affinity ligand D).

Conjugation of Anti-B4 With Blocked Ricin (Blocked Using Affinity Ligand D) (See FIG. 8)

Modification of Anti-B4 With SMCC

Anti-B4 (7.18 mg/mL) in 50 mM sodium phosphate buffer pH 7, containing NaCl (50 mM) and EDTA (1 mM) was mixed with SMCC (0.112 mM) added from a 20 mM stock solution in dry dioxane. The solution was then incubated at 30° C. for 30 minutes. The excess reagent was removed by filtration over a column of Sephadex G-25 that was equilibrated with 50 mM sodium phosphate, pH 7, containing NaCl (50 mM). About 0.5 maleimido groups per molecule of antibody were introduced under these experimental conditions, as determined using ($^{14}$C)-cysteine as described by Lambert et al., *J. Biol. Chem.* 260, 12035-12041 (1985).

Reduction of Blocked Ricin

Blocked ricin (1.0 mg/mL), blocked using affinity ligand D, was incubated at 0° C. in PBS adjusted to pH 6.8, containing EDTA (1 mM) and dithiothreitol (4.0 mM) for 20 hours. This concentration of reducing agent is sufficient to reduce the pyridyldisulfide bond in the ligand, but is insufficient to cause any reduction of the disulfide bond between the A-chain and the B-chain of ricin. Excess reducing agent was removed from the blocked ricin by gel filtration through a column of Sephadex G-25 (Superfine) equilibrated with 5 mM sodium acetate buffer, pH 4.7, containing NaCl (50 mM) and EDTA (0, mM). The blocked ricin contained about 1.3 sulfhydryl groups per blocked ricin, as assayed by the method of Ellman (cited above).

Conjugation of Modified Anti-B4 With Reduced Blocked Ricin

The solutions of the anti-B4 containing maleimido groups (4.2 mg/mL in the pH 7 buffer described above) and blocked ricin (0.6 mg/mL in the pH 4.7 buffer described above) were degassed and then mixed, and the mixture was placed under an atmosphere of nitrogen at 4° C. and incubated for 1 hour. The antibody to blocked ricin ratio in the reaction mixture was 7:1 (w/w). Iodoacetamide (2 mM) was then added to react with any remaining sulfhydryl groups in a 1 hour incubation at 4° C.

Purification of the Anti-B4-blocked Ricin Conjugate

The conjugation reaction mixture was made 0.2 mM in $CaCl_2$ and 0.2 mM in $MgCl_2$ and then passed over a column of immobilized concanavalin A similar to that described in Example 11 on preparation of antibody. The column (1 mL of packed gel per 2 mg of blocked ricin in the conjugation reaction) was equilibrated in PBS at 4° C., and loaded at 2 column volumes per hour. The column was then washed with 10–20 column volumes of PBS. The conjugate was eluted with PBS buffer containing 0.2M methyl α-D-mannopyranoside. The pool containing conjugate was diluted 10-fold with 0.1M sodium acetate buffer, pH 5, and then applied to a column of S-Sepharose (about 1 mL of gel for 10 mg of protein) equilibrated in 0.1M sodium acetate buffer, pH 5 at 4° C. (the concanavalin A-column elution pool may be concentrated before dilution with acetate buffer in order to make the sample load volume smaller for the ion-exchange column). The column was washed with 1–2 column volumes of pH 5 buffer and the conjugate was eluted with a gradient of NaCl (0–300 mM over 8 column volumes) in the pH 5 acetate buffer. Fractions containing conjugate were identified by SDS-PAGE (5–10% gradient gels using methods described by Lambert et al., *J. Biol. Chem.*, 260, 12035-12041 (1985)), pooled, concentrated, and applied to a column of Sephacryl S-300 for final purification and buffer exchange by gel filtration. The S-300 was equilibrated in PBS made with water-for-injection.

The purified conjugate was formulated by diluting to 0.1 mg/mL with PBS made with water-for-injection, and adding human serum albumin to a final concentration of 1.0 mg/mL. The formulated solution was filter-sterilized through 0.2 μm membranes and stored at 4° C.

Alternative Method of Purifying the Anti-B4-blocked Ricin Conjugate

The conjugation reaction mixture is diluted with 9 volumes of 50 mM sodium acetate buffer pH 5, and then applied to a column (1 mL of gel per 5 mg of protein) of S-Sepharose that is equilibrated in 50 mM sodium acetate buffer, pH 5. The column is washed with 2 column volumes of the pH 5 buffer and then the conjugate is eluted with a gradient of sodium chloride (0–300 mM over 8 column volumes) in the 50 mM sodium acetate buffer, pH 5. Fractions containing conjugate are identified by SDS-PAGE (5–10% w/v gradient gels as described by Lambert et al., *J. Biol. Chem.* 260, 12035-12041 (1985)). The fractions containing conjugate, that also contain non-conjugated antibody which is only partially resolved from the conjugate by this chromatography, are pooled and the pH is adjusted to 7 by the addition of dibasic sodium phosphate (from a 0.2M stock solution). The solution containing the conjugate is applied to a column (1 mL of gel for 10 mg of protein) of immobilized anti-blocked ricin antibody.

Hybridoma #bR12-2 secretes a murine $IgG_1$ which recognizes blocked ricin. This hybridoma is available from ImmunoGen Inc. It was derived using the standard techniques for the derivation of hybridomas secreting murine antibodies (Kohler et al. and Goding, cited above). A brief description of the methods is in Example 6. Ascites fluid from this hybridoma was generated by injecting hybridoma cells into pristane-primed BALB/c mice, and the $IgG_1$ monoclonal antibody was purified from the resulting ascites fluid by the same procedure as described for the purification of anti-B4 (also an $IgG_1$) in Example 11. An affinity column containing immobilized anti-blocked ricin antibody was made by covalently linking the antibody to AffiPrep 10 activated support matrix from Bio-Rad according to the manufacturer's instructions. The anti-blocked ricin immunoaffinity column was then blocked before use by incubating the column with a solution containing 10 mg/mL human serum albumin for 24 h at 4° C. The column is washed with phosphate-buffered saline before loading the solution of conjugate. After the conjugate solution is loaded onto the column, the column is washed with phosphate-buffered saline until no protein elutes from the column. The conjugate is then eluted with 0.1M glycine-HCl buffer. pH 2.7, collecting fractions into tubes containing 1M $K_2HPO_4$ (0.2× fraction volume).

In the final step of purification, the conjugate is submitted to gel filtration through a column of Sephacryl S-300 equilibrated in phosphate-buffered saline. Sterile water-for-injection was used to prepare the solutions used in all the columns described in this procedure. The purified conjugate is formulated by diluting to 0.1 mg/mL with phosphate-buffered saline (made using water-for-injection). and adding human serum albumin carrier protein to a final concentration of 1.0 mg/mL. The formulated solution of conjugate is filter-sterilized by passing through a 0.2 micron membrane filter, and it is stored at 4° e.g,

EXAMPLE 14

Conjugation of Anti-B4 to Blocked Ricin (Blocked With Affinity Ligand C) Using A Disulfide Linker

Modification of Anti-B4

Anti-B4 is modified with 2-iminothiolane as described in Example 12, to introduce about 1.8 sulfhydryl groups per molecule of antibody.

Conjugation of Modified Anti-B4 With Blocked Ricin, Blocked Using Affinity Ligand C Modified anti-B4 containing free sulfhydryl groups (5 mg) in 8 mL of 5 mM bis/tris-acetate buffer, pH 5.8, containing NaCl (50 mM) and EDTA (1 mM) is mixed at 4° C. with blocked ricin (1 mg) in 1.3 mL of PBS that has been blocked using activated affinity ligand C. This affinity ligand contains a pyridyldisulfide group that is still present in the blocked ricin. This group reacts with the sulfhydryl groups introduced into anti-B4 by modification with 2-iminothiolane, resulting in the linkage of anti-B4 and blocked ricin by a bond cleavable by reduction. The pH of the reaction mixture is adjusted to 7 by adding 0.08 mL of 0.5M triethanolamine-HCl buffer, pH 8 , and then incubated for 48 hours at 4° C. Iodoacetamide (5 mM) is added to block any remaining sulfhydryl groups.

Purification of Anti-B4-blocked Ricin (Disulfide-linked) Conjugate

The non-conjugated blocked ricin is removed from the reaction mixture by using gel filtration through a column of BioGel A-1.5m equilibrated in 10 mM Hepes buffer, pH 7.5, containing NaCl (0.5M), lactose (10 mM) and $NaN_3$ (0.05% w/v).

The non-conjugated antibody is removed from the anti-B4-blocked ricin conjugate by using a column of immobilized concanavalin A as described in Example 12. The purified conjugate is finally dialyzed against PBS. The conjugate is stored in 200 μL aliquots which are frozen in liquid nitrogen for storage at −70° C.

EXAMPLE 15

Figure 9:
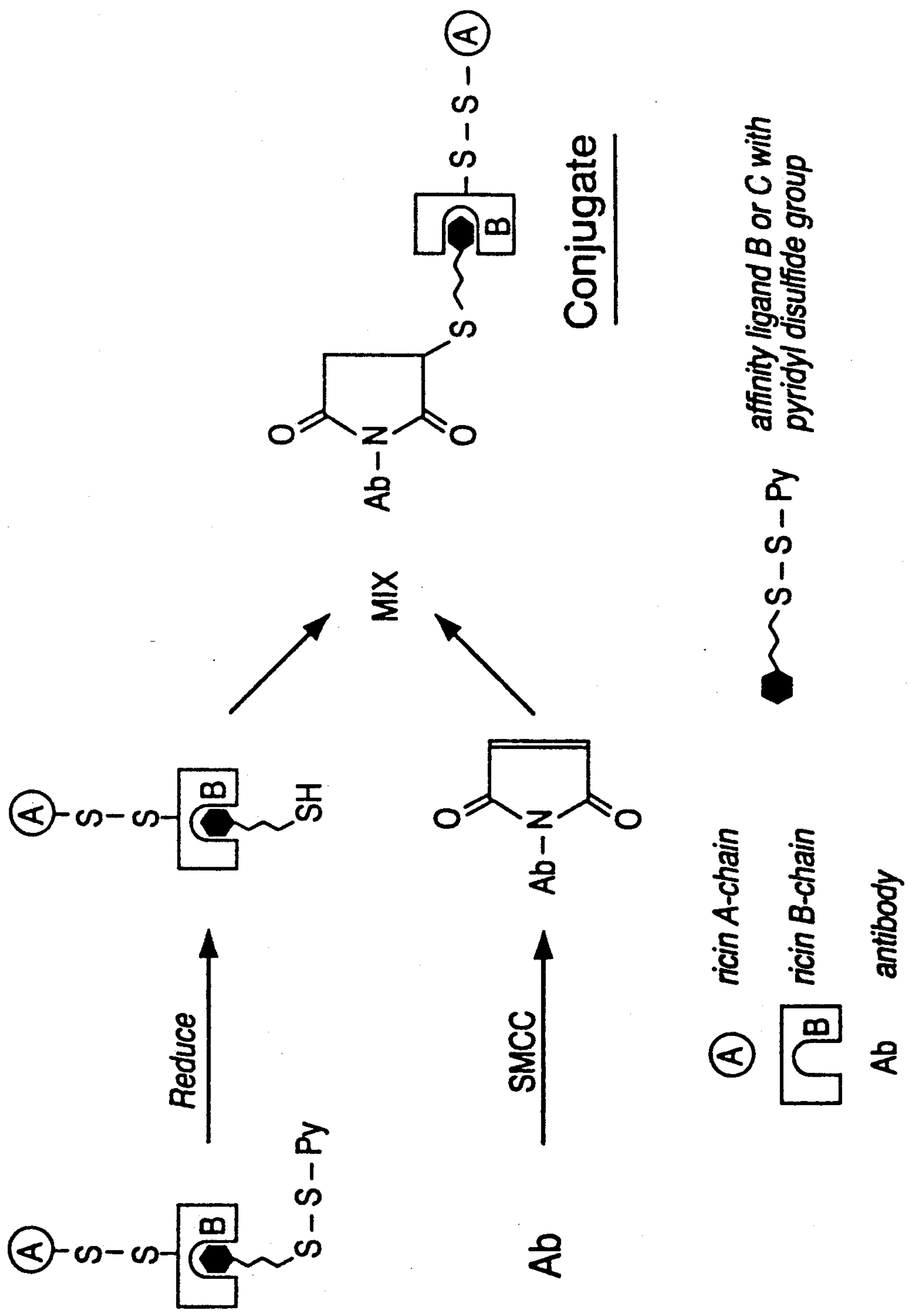
FIG. 9 illustrates an example of the preparation of a conjugate between an antibody and blocked ricin (blocked with affinity ligand B or C).

Alternative Method for Conjugation of Anti-B4 to Blocked Ricin (Blocked With Affinity Ligand C) (See FIG. 9)

Modification of Anti-B4 With SMCC

Anti-B4 (0.8 mg/mL) in 0.1M sodium phosphate buffer, pH 7, containing EDTA (1 mM) was mixed with SMCC (0.084 mM) added from a 10 mM stock solution in dry dioxane, and then incubated at 30° C. for 30 minutes. The excess reagent was removed by overnight dialysis against 0.1M sodium phosphate, pH 7, containing EDTA (1 mM). About 1-2 maleimido groups per molecule of antibody were introduced under these experimental conditions, as determined using ($^{14}$C)-cysteine as described by Lambert et al., *J. Biol. Chem.* 260, 12035-12041 (1985).

Reduction of Blocked Ricin (Blocked Using Affinity Ligand C

Blocked ricin (0.78 mg/mL), blocked using affinity ligand C which contains a pyridyldisulfide group, was incubated at 0° C. in PBS adjusted to pH 6.8, containing EDTA (1 mM) and dithioerythritol (0.5 mM) for 16 hours. This concentration of reducing agent is sufficient to reduce the pyridyldisulfide group, but is insufficient to cause any reduction of the disulfide bond between the A-chain and the B-chain of ricin. Excess reducing agent was removed from the blocked ricin by gel filtration on a column of Sephadex G-25 (Superfine) equilibrated with 5 mM bis/tris-acetate buffer, pH 5.8, containing NaCl (50 mM) and EDTA (1 mM). The pyridyldisulfide group of the affinity ligand C was quantitatively reduced to a free sulfhydryl group by this procedure.

Conjugation of Modified Anti-B4 With Reduced Blocked Ricin

The solutions of anti-B4 (6.7 mg in 8.6 mL of the pH 7 buffer described above) and blocked ricin (1 mg in 2.2 mL of the pH 5.8 buffer described above) were degassed and mixed. The solution was placed under an atmosphere of nitrogen at 4° C. and incubated for 18 hours. Then 2-mercaptoethanol (24 μM) was added to react with any remaining maleimido groups on the antibody, and after 45 minutes at 0° C., iodoacetamide (5 mM) was added to react with any remaining sulfhydryl groups in a 1 hour incubation at 4° C.

Purification of the Anti-B-4-blocked Ricin Conjugate

The above conjugation reaction mixture was placed in a dialysis bag ($M_r$ cut off, 3500), and concentrated to 2 mL by placing the sealed bag onto a bed of polyethylene glycol. The mixture was dialyzed for one hour against PBS containing lactose (10 mM) and then was subjected to gel filtration on a column of BioGel A-1.5m (95 cm×1.6 cm) equilibrated with 10 mM Hepes buffer. pH 7.5, containing NaCl (3.0M), lactose (10 mM) and $NaN_3$ (0.05% w/v), at a flow rate of 3 mL/h. Fractions were analyzed by SDS-PAGE (5-10% acrylamide gradient gels using methods described by Lambert et al., *J. Biol. Chem.* 260, 12035-12041 (1985)), and those containing the antibody-blocked ricin conjugate were combined.

The conjugate pool still contained some non-conjugated antibody, although it was free of non-conjugated blocked ricin. The mixture was applied to a column (0.5 mL) of concanavalin A, which binds the blocked ricin component of the conjugate. Non-conjugated antibody was removed by washing the column with buffer, and the purified conjugate was then eluted using the same conditions as described in Example 8. The purified anti-B4-blocked ricin was dialyzed into PBS, and then frozen in liquid nitrogen in small aliquots (200 μL) for storage at −70° C.

EXAMPLE 16

Conjugation of Anti-B4 to Blocked Abrin (Blocked With Reduced and Alkylated Affinity Ligand C

Modification of Anti-B4 With SMCC

Anti-B4 antibody was modified with SMCC as described for anti-B4 in Example 13.

Modification of Blocked Abrin

When there is no reactive group on the blocked abrin, as when affinity ligand A is used to block the binding sites of the lectin portion of abrin, or, as in this section, when affinity ligand C is first reduced and the resulting sulfhydryl group is alkylated by reaction with iodoacetamide prior to its use in preparing blocked abrin, the blocked abrin must be modified with a cross-linking reagent in order to provide a reactive group for conjugation with antibody.

Blocked abrin (0.4 mg/mL) in a buffer of 50 mM triethanolamine-HCl, pH 8.0, containing EDTA (0.5 mM) was mixed with 2-iminothiolane (2.5 mM) and incubated for 90 minutes at 0° C. under an atmosphere of nitrogen. Stock solutions of 2-iminothiolane were prepared as referenced in Example 12. The reaction was terminated by removing excess reagent by gel filtration through a column of BioGel P-6 (Fine) equilibrated with 50 mM potassium phosphate buffer, pH 7, containing EDTA (1 mM). These conditions resulted in the incorporation of about 1.0 sulfhydryl group per molecule of blocked abrin, as determined by the method of Ellman (cited above, Example 12).

Conjugation of Maleimido-modified Anti-B4 With Sulfhydryl-modified Blocked Abrin Modified anti-B4 (4.5 mg) in 3.5 mL of 0.05M sodium phosphate buffer, pH 7, containing NaCl (50 mM) and EDTA (1 mM) is mixed at 4° C. with modified blocked abrin (1 mg) in 4.8 mL of the pH 7 buffer. The mixture is incubated for 24 hours and then iodoacetamide (2 mM) is added to block any remaining sulfhydryl groups in an overnight incubation at 4° C.

Purification of Anti-B4-blocked Abrin Conjugate

The conjugate is purified by concentrating the reaction mixture using dialysis against polyethylene glycol, for gel filtration through BioGel A-1.5m, followed by an affinity purification using a column of immobilized concanavalin A, as described for the anti-B4-blocked ricin conjugate in Example 14. The purified conjugate is finally dialyzed against PBS. The conjugate is placed into small aliquots (200 μL) and is stored at −70° C. (samples frozen in liquid nitrogen).

EXAMPLE 17

Conjugation of an Anti-B4 to Blocked Abrin (Blocked With Affinity Ligand C)

Modification of Anti-B4 With SMCC

Monoclonal antibody anti-B4 was modified with SMCC (Pierce Chem. Co.) in a fashion similar to that described in Example 13.

Reduction of the Pyridyldisulfide Group of Blocked Abrin That Had Been Blocked With Affinity Ligand C Blocked abrin (0.86 mg/mL) in PBS containing EDTA (1 mM) was incubated with dithioerythritol (0.5 mM) for 2 hours at 0° C. These conditions result in the reduction of the pyridyldisulfide group, but do not cleave the disulfide bond between the A-chain and B-chain of abrin. The excess reducing agent is removed by gel filtration through a column of Sephadex G-25 (Superfine) equilibrated in 5 mM bis/tris-acetate buffer, pH 5.8, containing NaCl (50 mM) and EDTA (1 mM).

Conjugation of Modified Anti-B4 With Reduced Blocked Abrin

The maleimido-modified anti-B4 (8.9 mg) in 13 mL of 50 mM sodium phosphate buffer, pH 7, containing NaCl (50 mM) and EDTA (1 mM) is mixed with reduced blocked abrin (1 mg) in 2.4 mL of 5 mM bis/tris-acetate buffer. pH 5.8, containing NaCl (50 mM) and EDTA (1 mM), and then 20 μL of 0.5M triethanolamine-HCl buffer, pH 8, is added to raise the pH to 7. The conjugation reaction mixture is incubated at 4° C. for 18 hours.

2-mercaptoethanol (50 μM) is then added to the mixture to block any remaining maleimido groups, and after 15 minutes at 25° C., iodoacetamide (5 mM) is added to block any remaining sulfhydryl groups in a 3 hour incubation at 25° C.

Purification of the Anti-B4-blocked Abrin Conjugate

The anti-B4-blocked abrin conjugate is purified by the same procedure described in Example 16. After the affinity step on a column of immobilized concanavalin A. the purified conjugate is finally dialyzed against PBS and stored frozen in small aliquots (200 μL) at −70° C. after freezing the aliquots in liquid nitrogen.

EXAMPLE 18

Conjugation of Anti-My9 to Blocked Abrin (Blocked With Affinity Ligand C)

Monoclonal Antibody Anti-My9

Anti-My9 is a murine $IgG_{2b}$ described by Griffin et al., *Leuk. Res.* 8, 521-534 (1984). The anti-My9 antibody was purified by the same procedure used for antibodies anti-$T11_{1B}$ and anti-$T11_{1C}$ described in Letvin et al., *Blood* 66, 961-966 (1985). The anti-My9 antibody is commercially available from Coulter Immunology.

Modification of Anti-My9 With SMCC

Anti-My9 (1.9 mg/mL0 in 0.1M potassium phosphate buffer, pH 7, containing NaCl (145 mM) and EDTA (1 mM) was mixed with SMCC (60 μM) added from a stock solution (5 mM) in dry dioxane. The reaction solution was incubated at 30° C. for 45 minutes, and then excess reagent was removed by gel filtration at 4° C, through a column of Sephadex G-25 (Superfine) equilibrated in 0.1M potassium phosphate, pH 7, containing EDTA (1 mM). About 1.0 maleimido group per molecule of antibody was incorporated by this procedure, measured as described in Lambert et al., *J. Biol. Chem.* 260, 12035-12041 (1985).

Reduction of the Pyridyldisulfide Group of Blocked Abrin That Had Been Blocked With Affinity Ligand C Blocked abrin (0.86 mg/mL) in PBS containing EDTA (1 mM) was incubated with dithioerythritol (0.5 mM) for 2 hours at 0° C. These conditions result in the reduction of the pyridyldisulfide group, but do not cleave the disulfide bond between the A-chain and B-chain of abrin. The excess reducing agent is removed by gel filtration through a column of Sephadex G-25 (Superfine) equilibrated in 5 mM bis/tris-acetate buffer, pH 5.8. containing NaCl (50 mM) and EDTA (1 mM).

Conjugation of Modified Anti-My9 With Reduced Blocked Abrin

The maleimido-modified anti-My9 (8.9 mg) in 13 mL of 0.1M potassium phosphate buffer, pH 7, containing EDTA (1 mM) was mixed with reduced blocked abrin (1 mg) in 2.4 mL of 5 mM bis/tris-acetate buffer, pH 5.8, containing NaCl (50 mM) and EDTA (1 mM), and then 20 μL of 0.5M triethanolamine-HCl buffer, pH 8. was added to raise the pH to 7. The mixture was incubated at 4° C. for 18 hours. Then 2-mercaptoethanol (50 μM) wa added to the mixture to block any remaining maleimido groups, and after 15 minutes at 25° C., iodoacetamide (5 mM) was added to block any remaining sulfhydryl groups in a 3 hour incubation at 25° C.

Purification of the Anti-My9-Blocked Abrin Conjugate

The anti-My9-blocked abrin conjugate was purified by the same procedure described in Example 10, except that the buffer used for gel filtration on the column of BioGel A-1.5m was 10 mM HEPES buffer, pH 7.5, containing NaCl (0.5M) and $NaN_3$ (0.01% w/v).

After the affinity step on a column of immobilized concanavalin A, the purified conjugate (in about 14% yield with respect to blocked abrin) was finally dialyzed against PBS and stored frozen in small aliquots (200 μL) at −70° C. after freezing the aliquots in liquid nitrogen.

EXAMPLE 19

Conjugation of Anti-N901 to Blocked Ricin That Had Been Blocked With Affinity Ligand C

Monoclonal Antibody Anti-N901

Anti-N901 is a murine IgG1 first described by Griffin et al., *J. Imm.* 130 2947-2951 (1983). It was purified by the same procedure described for purifying anti-B4 in Example 11. The monoclonal anti-N901 antibody is commercially available from Coulter Immunology. Hialeah. Fla.

Conjugation of anti-N901 to Blocked Ricin That Had Been Blocked With Affinity Ligand C The modification of the antibody, preparation of the blocked ricin, the conditions for conjugation of the antibody and lectin and the purification of the resulting conjugate were performed using the same methods described in Example 15 for making the anti-B4 antibody-blocked lectin conjugate.

EXAMPLE 20

Conjugation of J5 to Blocked Ricin (Blocked With Affinity Ligand C) and Purification Using An Anti-Ricin Column

Monoclonal Antibody J5

Monoclonal antibody J5 was purified as described in Example 8.

Modification of J5 With SMCC

J5 (1 mg/mL) in 0.1M sodium phosphate buffer, pH 7, containing EDTA (1 mM) was incubated for 30 minutes at 30° C. with SMCC (28 μM). The modified J5 was separated from excess reagent by gel filtration through Sephadex G-25 (Superfine). About 0.7 maleimido groups were introduced under these conditions, as measured according to the method described in Lambert et al., *J. Biol. Chem.* 260, 12035-12041 (1985).

Reduction of Blocked Ricin That Had Been Blocked With Affinity Ligand C

Blocked ricin (1 mg) was reduced as described in Example 15.

Conjugation of Maleimido-J5 With Reduced Blocked Ricin

This reaction was carried out by the same procedure as described for anti-B4-blocked ricin described in Example 15.

Purification of J5-blocked Ricin Conjugate

Non-conjugated antibody was removed from the reaction mixture by immunoaffinity chromatography using a column of immobilized rabbit anti-ricin immunoglobulin. An anti-ricin column was made by linking affinity-purified heteroclonal rabbit anti-ricin (rabbit IgG from Sigma Chemical Co., purified by binding to a column of immobilized ricin (Sigma) and eluting a fraction of the IgG with 0.1M acetic acid, pH 3, containing 0.15M NaCl) to AffiGel 10 beads (N-hydroxysuccinimide ester-containing agarose. Bio-Rad) according to the manufacturer's instructions. The antibody-blocked ricin conjugate and blocked ricin were retained on the anti-ricin immunoaffinity column, and, after washing the column with PBS to remove non-conjugated antibody, were eluted quantitatively using a buffer of 0.1M acetic acid, pH 3, containing NaCl (0.15M).

The non-conjugated blocked ricin was removed from the J5-blocked ricin conjugate by gel filtration of the mixture through a column of BioGel A-1.5m equilibrated in 10 mM HEPES buffer, pH 7.5, containing NaCl (3M). lactose (I0 mM) and $NaN_3$ (0.05% w/v). Finally, the purified conjugate was dialized against PBS, and small aliquots (200 μL) frozen in liquid nitrogen for storage at −70° C. The yield was 21% with respect to blocked ricin.

EXAMPLE 21

Conjugation of Anti-B4 to Blocked Ricin (Blocked With Affinity Ligand C) and Purification Using An Anti-Ricin Column

Modification of Anti-B4 With SMCC

Anti-B4 was modified with SMCC as described in Example 13.

Reduction of Blocked Ricin That Had Been Blocked With Affinity Ligand C

Blocked ricin (1 mg) was reduced as described in Example 17 for blocked abrin that had been blocked with affinity ligand C.

Conjugation of Maleimido-Anti-B4 With Reduced Blocked Ricin

This reaction is carried out by the same procedure as described for anti-B4-blocked abrin conjugation described in Example 16.

Purification of Anti-B4-blocked Ricin Conjugate

Non-conjugated antibody is removed from the reaction mixture by immunoaffinity chromatography using a column of immobilized rabbit anti-ricin immunoglobulin. An anti-ricin column is made by linking affinity-purified heteroclonal rabbit anti-ricin (rabbit IgG purchased from Sigma Chemical Co., that was purified by binding to a column of immobilized ricin, also from Sigma, and eluting a fraction of the bound IgG using a buffer 0.1M acetic acid, pH 3, containing 0.15M NaCl) to AffiGel 10 beads (N-hydroxysuccinimide ester-containing agarose. Bio-Rad) according to the manufacturer s instructions. The antibody-blocked ricin conjugate and blocked ricin are retained on the anti-ricin immunoaffinity column, and, after washing the column with PBS to remove non-conjugated antibody, are eluted quantitatively using a buffer of 0.1M acetic acid, pH 3, containing NaCl (0.15M).

The non-conjugated blocked ricin is removed from the anti-B4-blocked ricin conjugate by gel filtration of the mixture through a column containing BioGel A-1.5m equilibrated in 10 mM HEPES buffer, pH 7.5, containing NaCl (3M), lactose (10 mM) and $NaN_3$ (0.05% w/v). Finally, the purified conjugate is dialyzed against PBS. and small aliquots (200 μL) frozen in liquid nitrogen for storage at −70° C.

EXAMPLE 22

Conjugation of the Lymphokine, Interleukin-2 (IL-2), to Blocked Ricin (Blocked With Affinity Ligand A)

IL-2

Purified recombinant forms of the lymphokine. interleukin-2 (IL-2), are commercially available from Bio-Gen Inc., Cambridge. Mass.; Amgen Biologicals, Thousand Oaks, Calif. and Boehringer Mannheim, West Germany.

Modification of Recombinant IL-2 (rIL-2)

rIL-2 (0.5 mg/mL) prepared in 16 mM triethanolamine-HCl buffer, pH 8. was treated with SPDP (64 μM), added from a freshly prepared stock solution of SPDP (10 mM) in ethanol. The reaction mixture was incubated at 30° C. for 15 minutes. Then the modified rIL-2 was separated from excess reagent by gel filtration at 4° C. by passing the solution through a column of Sephadex G-25 (Superfine) equilibrated with 10 mM triethanolamine-HCl buffer, pH 8.

About 0.8 pyridyl disulfide groups per molecule were incorporated into the rIL-2 using these conditions.

Pyridyldisulfide groups can be reduced in order to yield rIL-2 containing an introduced free sulfhydryl group, rIL-2 (0.1–0.5 mg/mL) was prepared in 10 mM triethanolamine-HCl buffer, pH 8. The solution was made 0.2 mM in dithioerythritol and was then incubated for 60 minutes at 0° C. under an atmosphere of nitrogen. The modified interleukin was then separated from sulfhydryl compounds of low molecular weight by gel filtration at 4° C. by passage of the solution through Sephadex G-25 (Superfine) that was equilibrated in 10 mM triethanolamine-HCl buffer, pH 8, containing EDTA (1 mM).

Sulfhydryl groups were quantified by the method described in Ellman (*Arch. Biochem. Biophys.*, 82, 70–77 (1959)). Pyridyldisulfide groups are converted quantitatively into sulfhydryl groups by this procedure.

Modification of Blocked Ricin (Blocked Using Affinity Ligand A)

Blocked ricin can be modified with SMCC as described in Example 8.

Conjugation of Modified rIL-2 With Modified, Blocked Ricin, and Purification of rIL-2-blocked Ricin Modified rIL-2 (0.5 mg) containing sulfhydryl groups is mixed at 4° C. with modified, blocked ricin (2 mg) 1 containing maleimido groups (5–10 mL). The pH of the solution is adjusted to 7 by titration with dilute acetic acid. After two hours at 4° C., mercaptoethanol (10 μM) is added to block any unreacted maleimido groups, and after 15 minutes at 25° C., iodoacetamide (2 mM) is added to block any unreacted sulfhydryl groups during incubation for a further 60 minutes at 25° C.

The solution containing rIL-2-blocked ricin is acidified by adding 10 μL of glacial acetic acid per mL. and then the conjugate is purified by gel filtration through a column (95 cm×1.5 cm) of Sephadex G-100 (Superfine) equilibrated with 20 mM sodium acetate buffer, pH 3.3, containing NaCl (30 mM). The column is run at 1–5 mL/hr, collecting 2 mL fractions. The fractions containing the desired conjugate are located by analyzing the fractions by SDS-PAGE (10% acrylamide) using methods described by Lambert et al., *J. Biol. Chem.*, 260, 12035–12041 (1985).

Fractions containing rIL-2-blocked ricin are pooled. sterilized by filtration (0.22 μm Millex GV filters. Millipore Corp. Bedford. MA) and stored frozen in small aliquots (200 μL) at −70° C.

EXAMPLE 23

Conjugation of Transferrin to Blocked Ricin (Blocked With Affinity Ligand C)

Transferrin

Targeting toxins to cells by directing toxins to the transferrin receptor on the surface of cells has potential clinical use in the treatment of cancer (Scott et al., *J. Natl. Canc. Inst.* 79, 1163–1172). Conjugates of toxins with transferrin can be used for this purpose. Purified human transferrin is available from Sigma Chemical Co. The apotransferrin was saturated with $Fe^{3+}$ using the $FeCl_3$-nitrilotriacetate procedure described by Ciechanover et al., *J. Biol. Chem.*, 258, 9681–9689 (1983) and by Aisen et al., *Biochem.*, 12, 3679–3685 (1973). Spectrophotometric analysis confirmed that the two iron-binding sites of transferring were saturated with $Fe^{3+}$.

Modification of Transferrin With SMCC

Transferrin (2 mg/mL) in 100 mM sodium phosphate buffer, pH 7, containing 1 mM $NaHCO_3$. was treated with SMCC (0.28 mM) for 30 minutes at 30° C. The SMCC was added from a freshly prepared stock solution (10 mM) in dry dioxane. The excess reagent was then removed by dialysis against the pH 7 buffer. About 1.0 maleimido group per molecule was introduced into the transferrin using these conditions, as determined by the method of Lambert et al., *J. Biol. Chem.* 260, 12035–12041 (1985).

Conjugation of Modified Transferrin With Blocked Ricin (Blocked Using Affinity Ligand C)

The reduction of the blocked ricin and the conjugation reaction between the reduced blocked ricin and transferrin used the same conditions as described in Example 15 for linking anti-B4 to blocked ricin.

Purification of Transferrin-blocked Ricin

The purification of the conjugate is achieved by gel filtration on a column (95 cm×1.6 cm) containing Bio-Gel A-1.5m in 10 mM HEPES buffer, pH 7.5, containing $NaHCO_3$ (1 mM). The flow rate was 3 mL/hr. Fractions are analyzed by SDS-PAGE (8% acrylamide) using methods described by Lambert et al., *J. Biol. Chem.* 260, 12035–12041 (1985).

No further purification of the conjugate is necessary since separation of transferrin-blocked ricin from transferrin and blocked ricin can be achieved in this single step. The purified conjugates are dialyzed into PBS containing $NaHCO_3$ (0.1 mM) and then frozen in liquid nitrogen in small aliquots (200 μL) for storage at −70° C.

EXAMPLE 24

Conjugation of Anti-T4 Monoclonal Antibody to Ricin (Blocked With Affinity Ligand C Monoclonal Anti-T4

Anti-T4 is a murine $IgG_{2a}$ antibody specific for the T4 molecule found on the surface of resting human "helper" T-cells. The antibody has been described by Meuer et al., *Proc. Natl. Acad. Sci.* (USA), 79, 4395–4399 (1982).

T4 is the surface antigen recognized by the HIV responsible for the disease AIDS. Anti-T4 is commercially available from Coulter Immunology. Hialeah FL. The antibody is purified by the procedures described for J5 referred to in Example 8.

Modification of Anti-T4 With SMCC, Reduction of Blocked Ricin (Blocked Using Affinity Ligand C) and Conjugation of the Anti-T4 With the Blocked Ricin These steps were carried out as described for the preparation of the J5-blocked ricin conjugate described in Example 20.

Purification of Anti-T4-Blocked Ricin Conjugate

This is accomplished by the same procedure as for purification of J5-blocked ricin (Example 20), except that the order of the steps was reversed. Non-conjugated blocked ricin is first removed from the mixture by gel filtration through a column of BioGel A-1.5m, and then in a second step, non-conjugated antibody is separated from anti-T4-blocked ricin conjugate by immunoaffinity chromatography. For buffer conditions and other details, see Example 20.

EXAMPLE 25

Conjugation of Anti-T11 Monoclonal Antibody to Blocked Ricin (Blocked With Affinity Ligand C)

Monoclonal Anti-T11

Several different monoclonal anti-T11 antibodies have been described, for example see Meuer et al., *Cell*, 36, 897–906. One of these, anti-$T11_{1A}$, is an $IgG_1$ monoclonal antibody. That monoclonal can be purified according to the procedure described by Letvin et al., *J. Clin. Invest.*, 78, 666–673. The antibody is commercially available from Coulter Immunology.

Modifiation of Anti-T11 With SMCC, Reduction of blocked Ricin (Blocked Using Affinity Ligand C) and Conjugation of the Anti-T11 With the Blocked Ricin The steps for modifying anti-T11 antibodies were carried out as described in Example 15 for preparing anti-B4-blocked ricin.

Purification of Anti-T11 -Blocked Ricin Conjugate

Purification is accomplished by the procedure described in Example 24 for anti-T4-blocked ricin.

EXAMPLE 26

Figure 10:
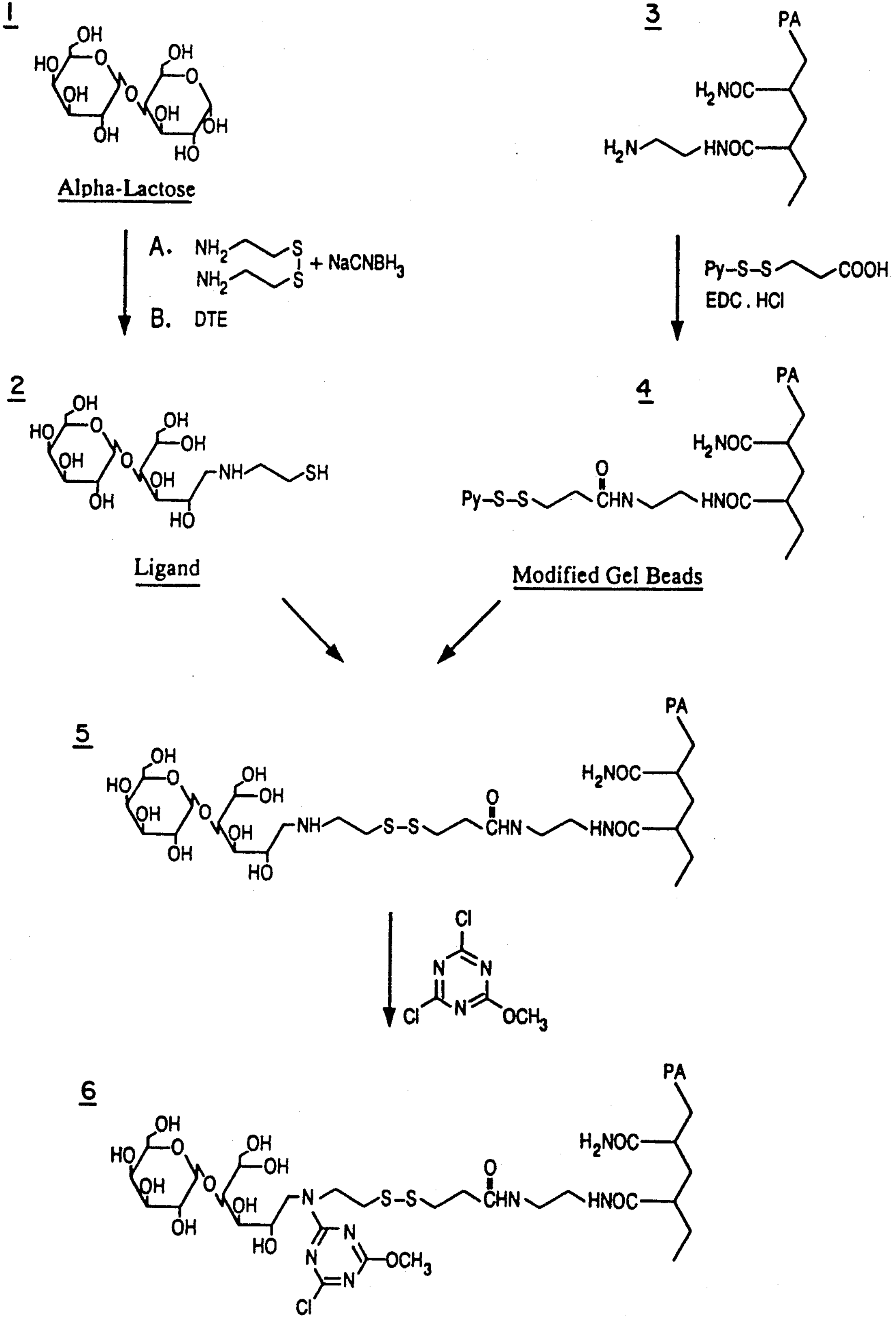
FIG. 10 is a schematic representation of the reactions leading to the production of the activated affinity support of Example 26.

Preparation of Monoclonal Antibody-Blocked Ricin Conjugate Employing First Affinity Support The reaction scheme for making the affinity support of this Example is depicted in FIG. 10.

Preparation of Solid Support

Aminoethylpolyacrylamide P-150 (Bio-Rad) in the form of solid beads was treated to cap any residual carboxyl groups by reaction with a water-soluble carbodiimide in aqueous ammonium chloride as described by Inman, *Meth. Enz.* 34, 30–58 (1974). The beads were then functionalized with pyridyldithio groups which provide a point of attachment for the ligand via a disulfide linkage as shown by the reaction summary depicted at the upper right of FIG. 10. To a suspension of the carboxy-capped aminoethylpolyacrylamide (30 mL of packed beads) and 10 mL of 0.1M sodium chloride was added 0.1 g (5 mmol) of 2-pyridyldithiopropionic acid in 10 mL of dimethylformamide and 1 mL of water. Diluted hydrochloric acid was added to adjust the pH to 4.7. This was mixed with 5 mL of water containing 1.15 grams of 1-ethyl-3-(3-dimethylaminopropyl)carbodiimide hydrochloride (EDC/HCl). The solution was 6 mmol in EDC. After agitation for 7 hours at room temperature, a further 0.766 gram (4 mmol) of the carbodiimide was added and the pH of the mixture was readjusted with hydrochloric acid to 4.7. After shaking for 4 days at room temperature, the suspension was drained and the modified gel beads 4 were washed extensively with 0.2M sodium chloride. To ensure removal of all of the excess 2-pyridyldithiopropionic acid, the suspension was acidified with 0.1M hydrochloric acid. This was followed by an extraction with 5 mL of ethyl acetate. The beads 4 were washed with 100 mM sodium phosphate buffer at pH 7. Washing was continued until a portion of the wash solution, when treated with an excess of dithioerythritol, revealed a very low concentration of 2-pyridinethione by exhibiting an absorbance of less than 0.1 a.u, at 343 nm.

The surface concentration of dithiopyridyl groups on the column of modified beads was determined by reacting a sample of the beads with an excess of dithioerythritol (DTE) in a solution of 100. mM sodium bicarbonate at room temperature for 30 minutes. The beads were washed repeatedly with a solution of 0.2M sodium chloride and the amount of 2-pyridinethione in the washings, as measured by absorbance at 343 nm, (Stuchbury et al., *Biochem. J.*, 151, 417–432 (1975)) corresponded to a concentration of 38 μmoles/mL of packed beads.

In order to cap any excess amino groups present on the 2-pyridyldithio-containing polymer beads 4, the beads (27 mL) were suspended in 50 mL of 100 mM sodium bicarbonate to which was added 4.8 g (5.2 mmol) methylchloroformate at room temperature. After 5 minutes, excess chloroformate was extracted with 20 mL ethyl acetate. The modified gel beads were washed with 100 mM sodium phosphate buffer at pH 7.

Preparation of N-(2′-mercaotoethyl)lactamine

N-(2′-mercaptoethyl)lactamine was prepared as depicted at the upper left of FIG. 10. A 13.5 mmolar solution of α-lactose monohydrate 1 was prepared (9.72 g in 36 mL of water). To the solution was added 3.68 g (13.5 mmole) of cystamine diacetic acid salt together with a solution of 1.70 g (27.0 mmole) sodium cyanoborohydride in 72 mL methanol. After adjusting the pH of the mixture to 6.2 with acetic acid, the solution was stirred at room temperature for 36 hours, at which time the methanol was removed by evaporation, the pH of the residual aqueous solution was adjusted to 5 with acetic acid, and the solution was applied to a 360 mL column of carboxymethylcellulose equilibrated in 2 mM pyridinium acetate buffer at pH 5. After washing the column with 2 volumes of the equilibrating buffer, the bound material was eluted with 0.1M aqueous ammonia solution. The solutions containing eluted material were evaporated to dryness. The solid was redissolved thoroughly in 200 mL of water to which was added 2.0 g (13.5 mmol) of DTE at room temperature. After standing for one hour, the resulting solution containing a mixture of N-(2′-mercaptoethyl)lactamine 2 and cystamine was applied to a 370 mL column of carboxymethylcellulose in 10 mM triethylammonium bicarbonate buffer at pH 7 containing 1 mM DTE. The column was washed with 500 mL of the same buffer and then developed with a linear gradient (1 L plus 1 L) of a solution of a 10–100 mM triethylammonium bicarbonate at pH 7 containing 1 mM DTE. Repeated evaporation from water and lyophilization produced 3.85 g of N-(2 -mercaptoethyl)lactamine ligand 2 as a white powder (35% of the theoretical amount).

Immediately before use the ligand 2 prepared and purified as described above was treated to reduce any dimers formed between two molecules of lactamine, by dissolving 1.5 g (3.7 mmol) of the ligand in 10 mL of water at pH 8, adding 154 mg (1 mmol) of DTE and allowing to stand at room temperature for one hour. The pH was then lowered to 5.2 with acetic acid, the solution was applied to a 100 mL column of carboxymethylcellulose in 2 mM pyridinium acetate buffer, pH 5.2. The column was washed with 200 mL of the same buffer to remove all of the DTE. The pure N-(2'-mercaptoethyl)lactamine 2 was eluted in the free thiol form with 0.1M hydrochloric acid. Upon assay with Ellman s reagent, the solution was found to contain 3.2 mmol of sulfhydryl compound (85% of the theoretical amount).

Preparation of Affinity Support

The ligand 2 was covalently linked to the solid support 4 previously prepared by adding 50 mL (3.2 mmol) of the lactamine solution 2 at pH 5 to 27 mL of the solid support at room temperature, resulting in a suspension at pH 6.5 which was shaken for 15 hours at room temperature, then washed repeatedly with 0.2M sodium chloride solution with successive centrifugation and decantation steps until the washings showed that substantially all of the 2-pyridinethione by-product had been removed, as indicated by measurements of the absorbance at 343 nm. The resulting beads, in the form of an affinity support 5 containing the ligand covalently linked to the polymeric beads had a surface lactose concentration of 38 mM.

In order to link ricin covalently to the affinity support 5, the latter was activated with the bifunctional cross-linking agent 2.4-dichloro-6-methoxytriazine by adding to a suspension containing 10 mL of the affinity support in 10 mL of a solution of 100 mM sodium bicarbonate, a solution containing 360 mg (2 mmol) of the triazine reagent in 10 mL dioxane. After vortexing the suspension for 1 minute, the excess triazine was extracted with 4 mL of diethyl ether: the activated affinity support probe beads 6 were then equilibrated with 100 mM sodium phosphate buffer at pH 7 and packed into a column.

Preparation of Lectin Affinity Support Complex

Ricin was applied to the activated support 6 in the form of 2.5 mL of a solution containing 2.1 mg/mL of ricin in 0.01M sodium phosphate buffer, pH 7, containing 0.15M NaCl. In order to form a covalent linkage between the ricin and the second functional chlorine group of the triazine cross-linking agent, the column was then washed with three column volumes of 50 mM triethanolamine-HCl buffer at pH 8.6. After standing for 24 hours at room temperature at pH 8.6, the column was washed with 3 volumes of 0.5M galactose solution at pH 7, in order to remove any ricin that had not formed a covalently linked ricin-ligand complex, i.e., blocked ricin.

Severing of Blocked Ricin From Solid Support

The blocked ricin prepared as described above was severed from the solid support by cleavage of the disulfide group between the ligand and the polymer. This disulfide group was cleaved or severed more readily by reduction with 10 mM DTE at pH 7 than is the disulfide group joining the A-chain and B-chain of the ricin itself. Although a variety of concentrations of DTE at pH values of from 7 to 8 were investigated, optimal results, with minimal cleavage of the ricin chains were obtained at a concentration of 10 mM DTE at pH 7 at room temperature for 45 minutes, producing a yield of 36% of the theoretical yield. The free complex thus obtained did not bind to asialofetuin, demonstrating that the binding sites of the ricin were blocked.

The ricin-ligand complex prepared as described above was purified on a column of concanavalin A-Sepharose in 100 mM sodium phosphate buffer, pH 6. The complex binds to concanavalin A via the carbohydrate chains of the ricin component, and can thus be freed of contaminants, in particular low molecular weight sulfhydryl compounds that would interfere with the conjugation reaction. The ricin-ligand complex was eluted from the lectin column with 100 mM sodium phosphate buffer, pH 6, with 1M methyl α-D-mannopyranoside, resulting in 12 mL of a solution in which there was 150–200 μg of ricin-ligand complex. With a specimen of the product, it was shown that the A-chain inhibited protein synthesis in reticulocyte lysates to the same extent as the A-chain derived from native ricin. The material passed through a column of immobilized asialofetuin, which has an association constant for ricin of about 0.1 μM. offering some confirmation that the ricin binding site was likely to be blocked.

Covalent Linking of Monoclonal Antibody to Blocked Ricin

In order to provide the ricin-ligand complex with the desired specificity towards selected cells, it was linked to anti-CALLA antibody J5. It can also be linked to anti-B4, anti-My9 or anti-N901.

For the purpose of conjugation to J5, J5 was purified and then modified with SMCC as described by Lambert et al., *J. Biol. Chem.*, 260, 12035–12041 (1985).

For the purpose of conjugation to anti-B4, the antibody is purified as described in Example 11 and then modified with SMCC as described in Example 13.

For the purpose of conjugation to anti-My9, the antibody is purified by the same procedure used for antibodies anti-$T11_{1B}$ and anti-T11 1C described in Letvin et al., *Blood* 66, 961–966 (1985) and then modified with SMCC as described in Example 18.

For the purpose of conjugation to anti-N901, the antibody was purified by the same procedure described for anti-B4 in Example 11 and then modified with SMCC as described in Example 13.

The solution of blocked ricin as described above was then mixed with the purified and modified J5 antibody in buffer at pH 7 and allowed to stand one hour at 4° C. Purified and modified anti-B4, anti-My9 or anti-N901 can also be used. After one hour, it was shown by SDS-PAGE that the reaction mixture contained a covalently linked conjugate between the monoclonal antibody and the blocked ricin, as well as excess monoclonal antibody and some unreacted blocked ricin. The reaction mixture was then affinity purified using protein A-Sepharose, in 100 mM sodium phosphate buffer, pH 7, which removed unreacted blocked ricin. More preferably, the reaction mixture is affinity purified using protein A-Sepharose, in 100 mM Tris-HCl buffer, pH 8.9 containing NaCl (3.0M) to remove unreacted blocked ricin. This step also removes the methyl α-D-mannopyranoside introduced earlier, thereby allowing the use of a column of concanavalin A-Sepharose as a further purification step. The material eluted from the protein A-Sepharose column, preferably at pH 6, which comprised conjugate and excess monoclonal antibody, was then applied to a column of concanavalin A-Sepharose, where, as previously, the conjugate was bound through the carbohydrate chains of the blocked ricin. Excess monoclonal antibody was then removed by extensive washing, and the bound conjugate was eluted with 1M methyl α-D-mannopyranoside in 100 mM sodium phosphate buffer, pH 7.

Both the blocked ricin, and the blocked ricin linked to the monoclonal antibody J5. were tested for cytotoxicity using Namalwa cells, a Burkitt's lymphoma line that expresses, on the average, 60,000 CALLA per cell, and more than 600.000 binding sites for ricin. The blocked ricin was found to be about 10 times less toxic than native ricin. This reduction in non-specific toxicity was concluded to be due to the blocking of the binding sites on the B-chain, as it was shown that the A-chain, when liberated from the blocked ricin, was fully active (vide supra).

When the blocked ricin was linked to J5, its toxicity increased three-fold for target cells expressing CALLA, and its toxicity decreased five-fold for non-target cells that do not express CALLA. Most significantly, the toxicity of the conjugate was reduced three-fold by addition of a saturating amount of J5. showing clearly that the antibody confers some specificity on the modified toxin.

EXAMPLE 27

Figure 11:
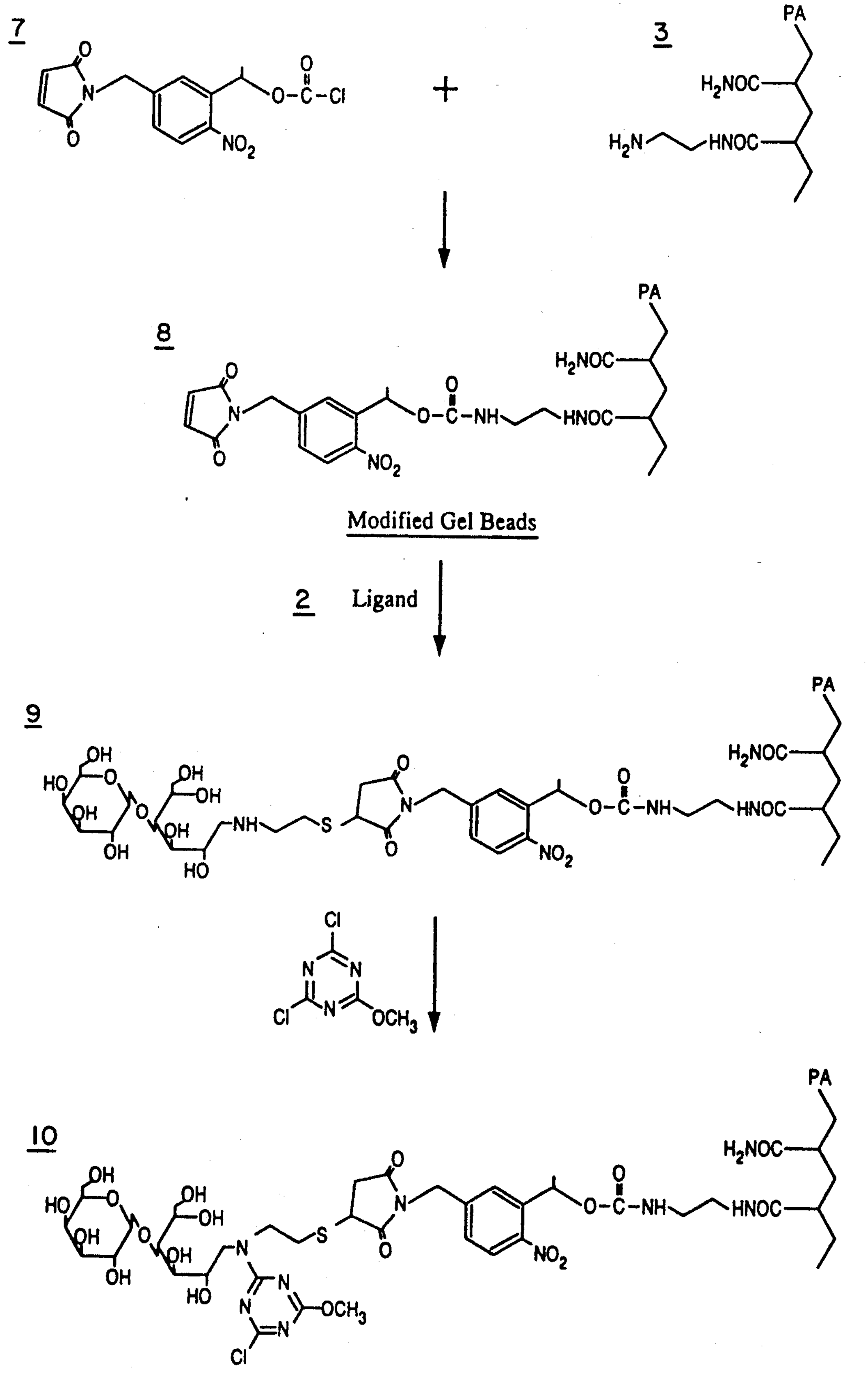
FIG. 11 is a schematic representation of the reactions leading to the production of the activated affinity support of Example 27.

Preparation of Monoclonal Antibody-Blocked Ricin Conjugate Employing Second Affinity Support The reaction scheme for making the affinity support of this Example is depicted in FIG. 11.

Preparation of the Solid Support

Carboxy-capped aminoethylpolyacrylamide P-150 3 was prepared as described in Example 26 (26 mL of packed beads) in 0.1M sodium bicarbonate (13 mL). To the suspension was added 1-(5-maleimidomethyl-2nitrophenyl)ethylchloroformate 7 (1.02 g corresponding to 3.48 mmol) in dioxane (6 mL). After 5 minutes of vigorous shaking methyl chloroformate (5 mL) was added to cap any excess amino groups and shaking was continued for another 5 minutes. Modified polyacrylamide gel beads 8 were then recovered by filtration and washed with 0.1M sodium phosphate buffer, pH 7, then a mixture of 0.1M sodium phosphate buffer, pH 7 and dimethylformamide (1:1, v/v), dimethylformamide and finally with the same solutions in reverse order.

Preparatio of Affinity Support

The modified polyacrylamide beads 8 (24 mL of packed beads) were suspended in 0.1M sodium phosphate buffer, pH 7 (10 mL) and treated with a solution of the ligand N-(2'-mercaptoethyl)lactamine 2 prepared as described in Example 2 (700 mg, 1.74 mmol) in water, pH 7. The mixture was shakened overnight and the affinity support probe 9 containing the ligand covalently linked to the polymeric beads was then recovered by filtration on a Büchner funnel and thoroughly washed with sodium phosphate buffer, pH 7. A sample of the affinity support 9 (0.3 mL) was used to prepare a small column and to measure the specific binding capacity of the affinity support beads for ricin. It was found that 1 mL of affinity support beads at pH 7 bound in excess of 1.0 mg of ricin in a specific fashion. All the specifically bound ricin could be eluted with buffer containing 0.2M lactose.

A column of affinity support beads 9 was activated with 2,4-dichloro-6-methoxytriazine (bifunctional cross-linking reagent) in the following way. A suspension of polyacrylamide beads containing the lactamine ligand (10 mL) was mixed with 0.1M sodium bicarbonate buffer (10 ml). To that was added a solution of 2,4-dichloro-6-methoxytriazine (0.24 g. 1.34 mmol) in dioxane (6.6 mL). The suspension was vigorously shaken for 1 min, and the excess triazine was then removed by extraction with diethyl ether (3×5 mL). The activated affinity support beads 10 were equilibrated with 0.1M sodium phosphate buffer, pH 6.5, and packed into a column.

Preparation of Lectin Affinity Support Complex

A solution of ricin (10 mg in 5 mL of 0.01M sodium phosphate buffer, pH 7 containing 0.15M sodium chloride) was passed twice through the activated affinity support column, which was then washed with three column volumes of 0.05M triethanolamine-HCl, pH 8.6 and left at ambient temperature for 24 hours. Ricin which was bound but not covalently cross-linked was removed from the beads by washing with 0.1M sodium phosphate buffer, pH 7 containing 0.2M lactose.

Severing of Blocked Lectin From Solid Support

Ricin retained by covalent linkage with the ligand was released from the solid support beads by photolysis in the following way. The beads were transferred from the column with 0.1M sodium phosphate buffer (10 mL) to a glass petri dish where the suspension formed a layer of not more than 0.5 cm thickness. The suspension was then irradiated for 10 minutes at a distance of 15 cm from a Black Ray Longwave U.V. Lamp (Model B-100 A. Ultraviolet Products. Inc., San Gabriel. Calif., emission peak at 365 nm, intensity at 15 cm was approximately 1.1 mW/cm$^2$) to cleave the linkage between the ligand and the solid support. The irradiated suspension was poured back into the column and the beads were thoroughly washed with 0.1M sodium phosphate buffer, pH 7. The combined washings (50 mL), which contained the released blocked ricin free from the solid support, were passed through a column of asialofetuin-TSK (2 mL, binding capacity for ricin: 4 mg/mL) to remove traces of ricin contaminants that may have been present. The final solution was concentrated to a volume of about 2 mL by ultrafiltration (YM-10 membrane, Amicon, Danvers, Mass.) and then passed through a small column of BioGel P-6 in 0.05M triethanolamine-HCl buffer, pH 8 containing sodium chloride (150 mM) and EDTA (1 mM). yielding 1.2 mg of pure ricin-ligand complex in 2.8 mL of buffer.

Covalent Linking of Monoclonal Antibody to Blocked Lectin

In order to link the blocked lectin covalently to antibody J5, anti-B4, anti-My9 or anti-N901, a sulfhydryl group was introduced into the blocked lectin with the cross-linking reagent 2-iminothiolane hydrochloride (Pierce Chemical Co.) and a maleimido group is introduced into the monoclonal antibody with the heterobifunctional cross-linking reagent SMCC, as described in detail below.

The solution of blocked ricin (2.8 mL) was cooled on ice. The ricin then was treated with a 0.5M solution of 2-iminothiolane HCl, pH 8 (0.044 mL), giving a final concentration of 2-iminothiolane of 8 mM. The reaction was stopped after 90 min on ice by gel filtration through a column of BioGel P-6 in 5 mM bis/tris-acetate buffer, pH 5.8, containing sodium chloride (50 mM) and EDTA (1 mM). In this way, an average of 0.8 sulfhydryl groups were introduced per molecule of blocked ricin.

Antibody J5 was modified with SMCC by adding to a 2 mg/mL solution of J5 in 0.1M sodium phosphate buffer. pH 7 (1.5 mL) 12 equivalents of SMCC (0.075 mg) in dry dioxane (0.02 mL). After incubation at 30° C. for 30 minutes, the reaction solution was passed through a column of Sephadex G-25 at 4° C. yielding modified J5 with an average of 1.5 maleimido groups per antibody molecule.

Anti-B4 was modified with SMCC as described in Example 13.

Anti-My9 was modified with SMCC as described in Example 18.

Anti-N901 was modified with SMCC as described in Example 13.

The solutions of modified blocked ricin (1–2 mg) and modified J5 (3 mg) were mixed and the pH was adjusted to 7 by adding 0.5M triethanolamine-HCl buffer, pH 8 (0.028 mL). Modified anti-B4, anti-My9 and anti-N901 can also be used. After standing overnight at 4° C., iodoacetamide was added to a final concentration of 5 mM and then the solution was concentrated by ultrafiltration (YM-10 filter, Amicon) to about 2 mL. The antibody was purified by filtration through a column of BioGel P-300 in phosphate-buffered saline (1.5 cm×96 cm).

Both the blocked ricin and the blocked ricin linked to the monoclonal antibody J5 displayed reduced nonspecific toxicity characteristics similar to those of the products of Example 26.

EXAMPLE 28

Figure 12A:
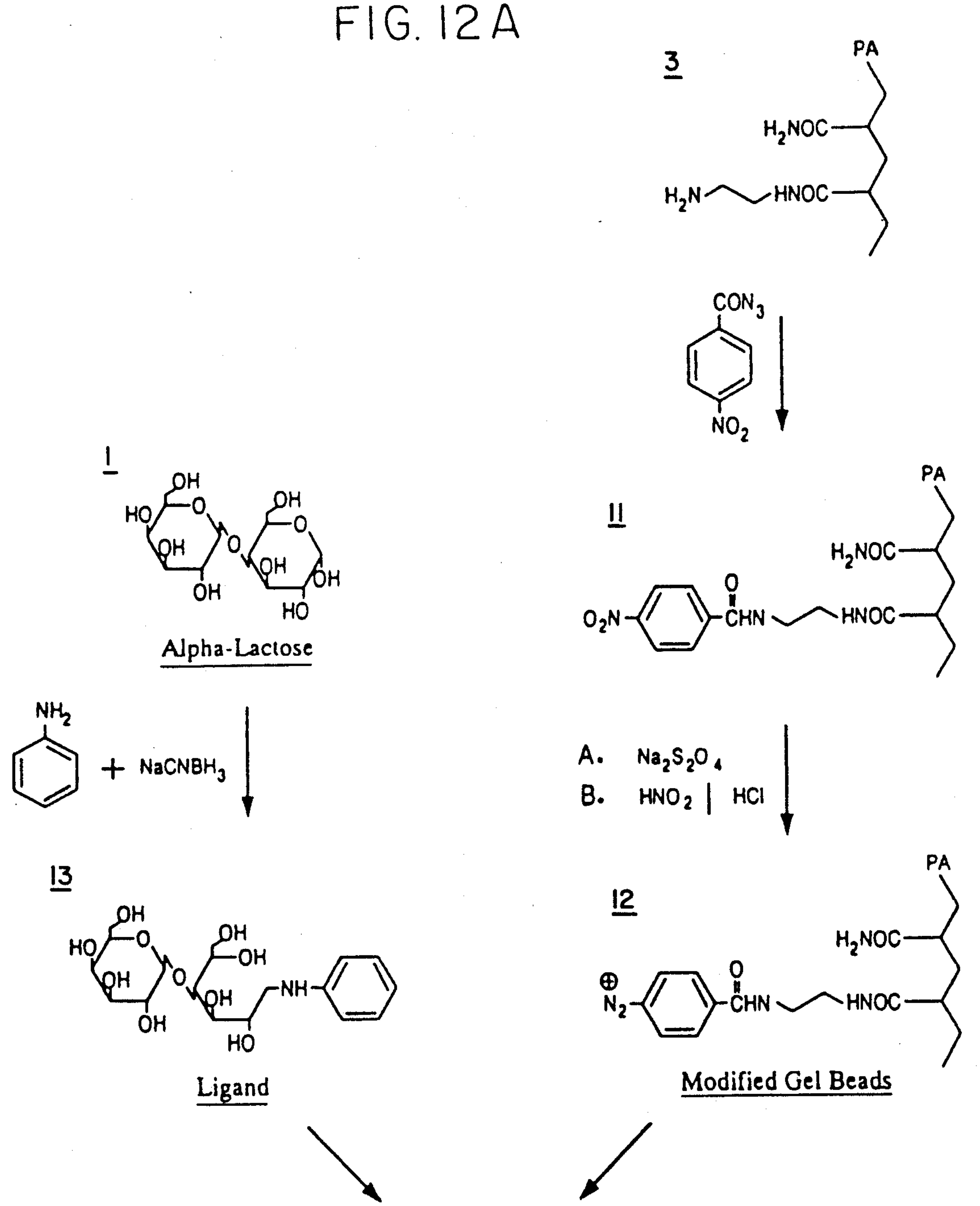
FIGS. 12(A) and 12(B) are schematic representations of the reactions leading to the production of the activated affinity support of Example 8.
Figure 12B:
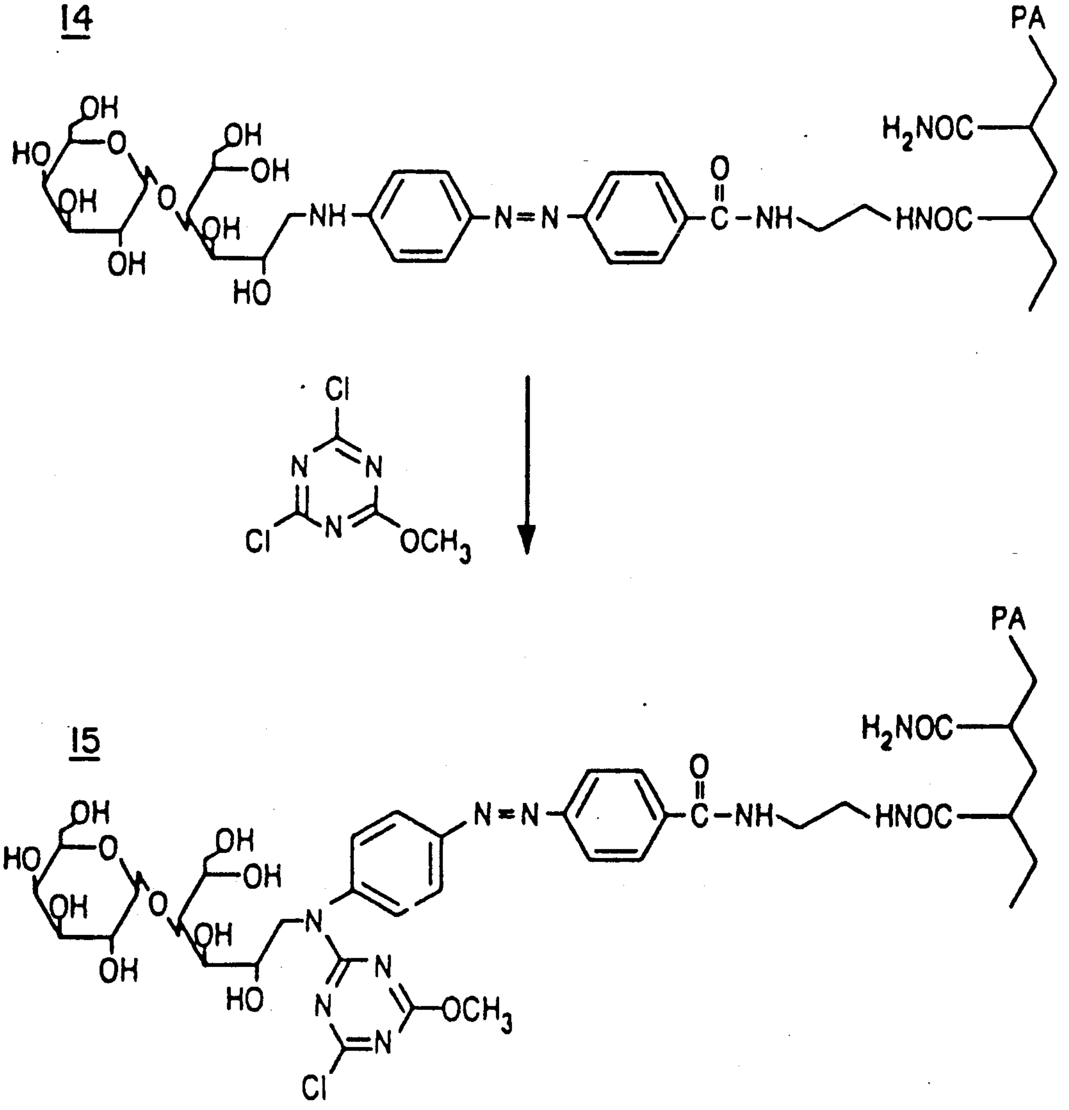

Preparation of Monoclonal Antibody-Blocked Ricin Employing Third Affinity Support In this example the ligand is linked via an azo functionality and can be released with 0.5M sodium dithionite, pH 8.5 (see, for example, Cohen, *Meth. Enz.* 33, 102–108 (1974)). The reaction sequence for making the affinity support is summarized in FIGS. 12(A) and 12(B).

Preparation of N-phenyllactamine

To a stirred solution of α-lactose (4.0 g. 11.1 mmol as the monohydrate) in water (40 mL) was added a solution of aniline (2.07 g. 22.2 mmol) in methanol (8 mL), and a solution of sodium cyanoborohydride (0.7 g. 11.1 mmol) in methanol (6 mL). The pH of the mixture was adjusted to 6.5 with acetic acid, and the solution was stirred at room temperature.

After 15 hr, methanol was removed by evaporation, and acetone (12 mL) was added to destroy excess sodium cyanoborohydride, and the solution was stirred at room temperature for 1 hour. This solution was then evaporated to dryness, the residue redissolved in water (75 mL) and the solution adjusted to pH 5.5 with acetic acid.

The solution was applied to a column (60 mL) of Amberlite IRA-118H ion-exchange resin, equilibrated in water. The column was washed with water (600 mL) and the sugar was eluted with a solution of 1M ammonium bicarbonate, giving 5.4 g of a white solid which contained N-phenyllactamine ligand 13 contaminated with some salt. N-phenyllactamine is also known as 1-deoxy-4-O-β-D-galactopyranosyl-1-(phenylamino)-D-glucitol.

Preparation of Solid Support

Carboxy-capped aminoethyl-polyacrylamide P-150 3 in 0.2M NaCl (12 mL of packed beads in a total volume of 20 mL) was added to p-nitrobenzoylazide (576 mg. 3 mmol) in THF (5 mL), and triethylamine (304 mg. 3 mmol). The gel was shakened gently for 20 minutes and then 304 mg (3 mmol) of triethylamine was then added. After shaking for 25 minutes, the p-nitrobenzoyl-substituted support beads 11 were washed successively with a mixture of THF and 0.2M NaCl solution (1:1, v/v), formamide and 0.2M NaCl solution.

The beads Were suspended in 100 mM NaHCO (10 mL) and shakened vigorously with methyl chloroformate (2 mL) for 5 minutes to cap any excess amino groups. The suspension was extracted with diethyl ether (2×15 mL) to remove excess chloroformate, and the beads were washed with 100 mM sodium phosphate buffer, pH 7. To a suspension of the gel in 100 mM sodium phosphate buffer. pH 7 (20 mL, final volume) was added sodium dithionite (2.61 g. 15 mmol). The suspension was maintained at 55° C. in a bath, being removed and shakened periodically. After 45 minutes, the p-aminobenzoyl-substituted support gel beads were washed with a solution of 0.2M NaCl. To a suspension of modified polyacrylamide gel beads (5 mL of packed beads) in 1M HCl (10 mL, final volume) at 0° C. was added cold sodium nitrite (699 mg, corresponding to 1 mmol) in water (1 mL). The suspension was shakened gently at 4° C. for 20 minutes and the beads were then washed quickly with a cold solution of 0.2M NaCl to provide p-diazobenzoyl-substituted support beads 12.

Preparation of Affinity Support

A solution of N-phenyllactamine ligand 13 (810 mg. 1.9 mmol) in saturated sodium borate (10 mL) was added to the cold diazo-modified support 12, which immediately turned a deep red color. The suspension was shakened gently at 4° C. overnight and was washed with 0.2M NaCl solution leaving a deep red-colored affinity support 14 in which the ligand was covalently linked to the solid support through an azo group. A portion of the affinity support 14 (0.05 mL) was used to prepare a small column with which the specific binding capacity was shown to be 0.5 mg of ricin per mL of packed beads.

It was established that the ricin was bound specifically by showing that the bound ricin could be eluted in two ways. Either the ricin-ligand specific interaction could be disrupted by competition with a high concentration of galactose or the ligand linkage to the solid support could be cleaved by treatment with a solution of 0.2–0.5M sodium dithionite, pH 8. In both cases, ricin or ricin-ligand complex was eluted quantitatively from the column. As further proof that treatment with dithionite released ricin by cleavage of the ligand from the solid support, the gel immediately lost its deep red color, which is due to the chromophore of the azo group.

The affinity support 14 was activated with the cross-linking reagent 2.4-dichloro-6-methoxytriazine in the following way. To a suspension of the affinity support beads 14 (5 mL volume packed beads in 100 mM sodium phosphate buffer, pH 7) in dry DMF (20 mL) was added 2,4-dichloro-6-methoxytriazine (1.8 g. 10.0 mmol) in dry DMF (10 mL). The suspension was agitated gently at room temperature for 22 hours. The activated affinity support beads 15 were then washed successively with DMF. DMF-100 mM sodium phosphate buffer, pH 7. and finally 100 mM sodium phosphate buffer, pH 7. and packed into a column.

Preparation of Blocked Lectin

A solution of ricin (5.7 mg in 3 mL 0.01M sodium phosphate buffer, pH 7, containing 0.15M sodium chloride) was applied to the activated affinity support column 15 and the flow-through reapplied twice. The column was washed with three column volumes of 0.05M triethanolamine-HCl buffer, pH 8.6, and left at ambient temperature for 24 hours. Ricin which was bound but not covalently cross-linked was removed by washing the column with 0.1M sodium phosphate buffer, pH 7, containing 0.5M galactose. The blocked ricin was released from the solid support by severing the covalent linkage in the following way. The column was washed with 0.05M triethanolamine-HCl buffer, pH 8.6 to remove residual galactose, and then with a solution of 0.2M sodium dithionite containing 0.3M sodium chloride, pH 8. The beads were then transferred to a separate container and stirred with the solution of 0.2M sodium dithionite, 0.3M sodium chloride, pH 8 for 20 minutes. The suspension was filtered and the beads were treated twice more with dithionite in the same way. The dithionite solutions were pooled, giving a solution of 12 mL containing approximately 0.8 mg of ricin-ligand complex free from the solid support.

The complex can be linked covalently to a monoclonal antibody such as J5. anti-B4, anti-My9 or anti-N901 using conventional bifunctional cross-linking agents.

Other lectins can be substituted for ricin with similar results. The monoclonal antibody-blocked complexes can be used to kill selected cells in vitro as well as in vivo.

EXAMPLE 29

In Vitro Tests of Specificity, Selectivity and Toxicity of Blocked Ricin and Conjugatse of Monoclonal Antibodies with Blocked Ricin

(a) Ribosome-inactivating Activity of Blocked Ricin and the Blocked Ricin Conjugates The inhibitory activity of the ricin A-chain of blocked ricin and antibody-conjugates of blocked ricin were measured in a rabbit reticulocyte lysate system, using the experimental protocol described in Lambert et al , *J. Biol. Chem.* 260, 12035-12041 (1985). The activity of ricin A-chain was compared with that of the ribosome-inactivating protein, gelonin. Ricin, blocked ricin, antibody conjugates of blocked ricin and gelonin were diluted to 4 μg/mL of ricin A-chain or gelonin in 10 mM potassium phosphate buffer, pH 7.4, containing NaCl (20 mM), bovine serum albumin (0.2 mg/mL) and 1% (v/v) 2-mercaptoethanol. These dilutions were incubated at 25° C. for 3 hours to allow for reduction of the disulfide bond linking the A-chain and B-chain as described by Olsnes et al., *Biochem.* 12, 3121-3126 (1973). The test samples were further diluted to 0.02 μg/mL in buffer without 2-mercaptoethanol and 1 μL samples used in the lysate assay system as described in Lambert et al. (cited above).

Figure 13A:
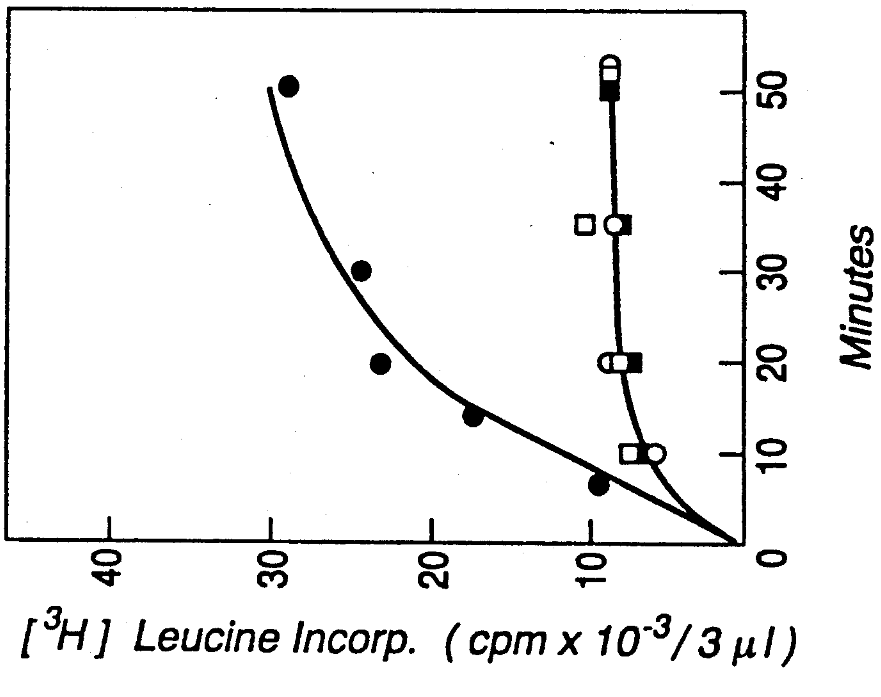
FIG. 13(A): closed circles, control assay; open circles, assay containing 20 pg of gelonin; closed squares, assay containing 20 pg of ricin A-chain; and open squares, assay containing 20 pg of ricin A-chain from blocked ricin.
Figure 13B:
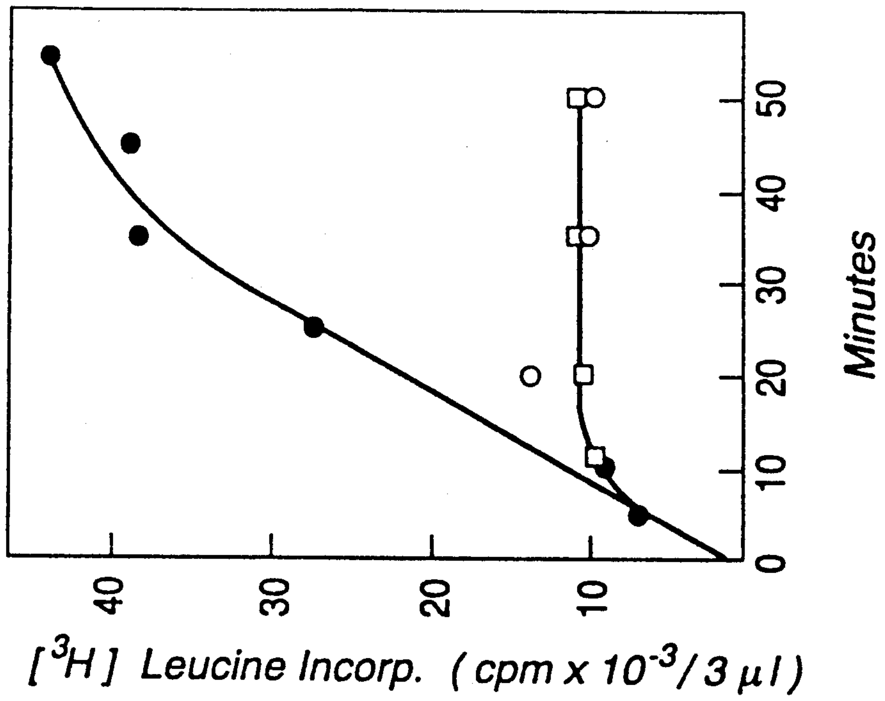
FIG. 13(B): closed circles, control assay; open circles, assay containing 20 pg of gelonin; and open squares, assay containing 20 pg of ricin A-chain from J5-blocked ricin conjugate.

The results shown in FIGS. 13(A) and 13(B) demonstrate that the A-chain of blocked ricin and of ricin are indistinguishable in their ability to inhibit protein synthesis in these assays, and they are equal to gelonin in their ribosome-inactivating activity. Also, after conjugation of blocked ricin to J5 by the procedure described in Example 20, the ricin A-chain from the conjugate still retained full activity, equal to gelonin. Thus the reaction of the activated affinity ligand C with ricin to produce blocked ricin does not affect the activity of the A-chain in inactivating ribosomes.

(b) Comparison of the Binding of Blocked Ricin and Ricin to Cell Surfaces

Blocked ricin that had been blocked with affinity ligand C and ricin were radiolabeled using the Bolton and Hunter reagent (Amersham) and the standard procedure described by Bolton et al., *Biochem. J.* 133, 529-539 (1973). The specific radioactivity of the proteins were 1.4×108 cpm/μg for blocked ricin and $2.4\times10^8$ cpm/μg for ricin (using a gamma counter, LKB, Gaithersburg. Md.).

Binding assays were performed in plastic tubes that had been preincubated with PBS containing 1% (w/v) bovine serum albumin Namalwa cells (ATCC CRL 1432) ($2\times10^6$ cells/tube) were incubated at 0° C. for 30 min in 100 μL of PBS containing 1% (w/v) bovine serum albumin and serial dilutions of radiolabelled ricin or blocked ricin, in the presence or absence of lactose. Cells were then washed three times with 2 mL of ice cold PBS containing 1% (w/v) bovine serum albumin. The radioactivity in tubes containing the cells was measured using a gamma counter (LKB). The results of a experiment are summarized below.

| SAMPLE | CONCENTRATION OF SAMPLE | COUNTS PER MIN ABOVE BACKGROUND (BACKGROUND = 60 cpm) | MOLECULES BOUND PER CELL |
|---|---|---|---|
| $^{125}$I-Blocked Ricin | $1\times10^{-7}$M | 28 | ~1000 |
| $^{125}$I-Blocked Ricin + 0.1M lactose | $1\times10^{-7}$M | 0 | <1000 |
| $^{125}$I-Ricin | $1\times10^{-7}$M | 6276 | 132,000 |
| $^{125}$I-Ricin + 0.1M lactose | $1\times10^{-7}$M | 183 | 3,900 |

The binding of blocked ricin is reduced by about 200-fold compared with ricin, as measured in this experiment. Thus, reaction of ricin with activated affinity ligand C not only blocks the binding of ricin to asialofetuin used in the affinity purification of blocked ricin, but also greatly reduces the binding of ricin by cells.

(c) Binding of Antibody-blocked Ricin Conjugates To Cells

Conjugates were tested for their ability to bind to the target cells specified by the particular antibody by using the technique of indirect immunofluoresence as described in detail in Lambert et al., *J. Biol. Chem.* 260, 12035–12041 (1985).

Conjugates were compared with the corresponding nonconjugated antibody as a control. The results of these studies showed that the conjugation of the antibodies to blocked ricin did not significantly impair the ability of the antibodies to bind to their cognate antigen expressed on target cells. There was no binding of any conjugate to cells that did not express the relevant antigen.

(d) Cytotoxicity of Blocked Ricin Conjugates

Cytotoxicity assays were done by the methods of Goldmacher et al. (J. Cell Biol. 102, 1312–1319 (1986) and *J. Imm.* 135, 3648–3651 (1985)) which provide direct assays of cell killing from the back-extrapolation of exponential growth curves and the measurement of colony-forming ability of cells treated with various substances for 24 hours. The surviving fractions established by these two methods were in good agreement and were used interchangably.

Figure 14:
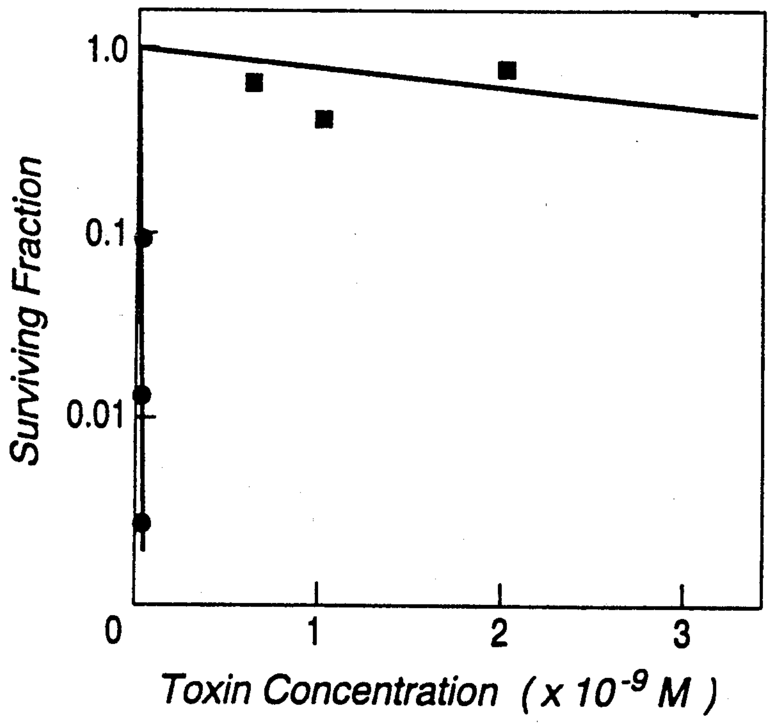
FIG. 14 shows the cytotoxicity of ricin and blocked ricin for Namalwa cells after 24 hours exposure to toxin. In the figure: closed circles, ricin; and closed squares, blocked ricin.

FIG. 14 shows the cytotoxicity of ricin and blocked ricin on Namalwa cells. The figure shows that ricin is highly toxic, with an $IC_{50}$ of less than 0.01 nM. while blocked ricin was much less toxic, with an $IC_{50}$ of about 3 nM.

Figure 15:
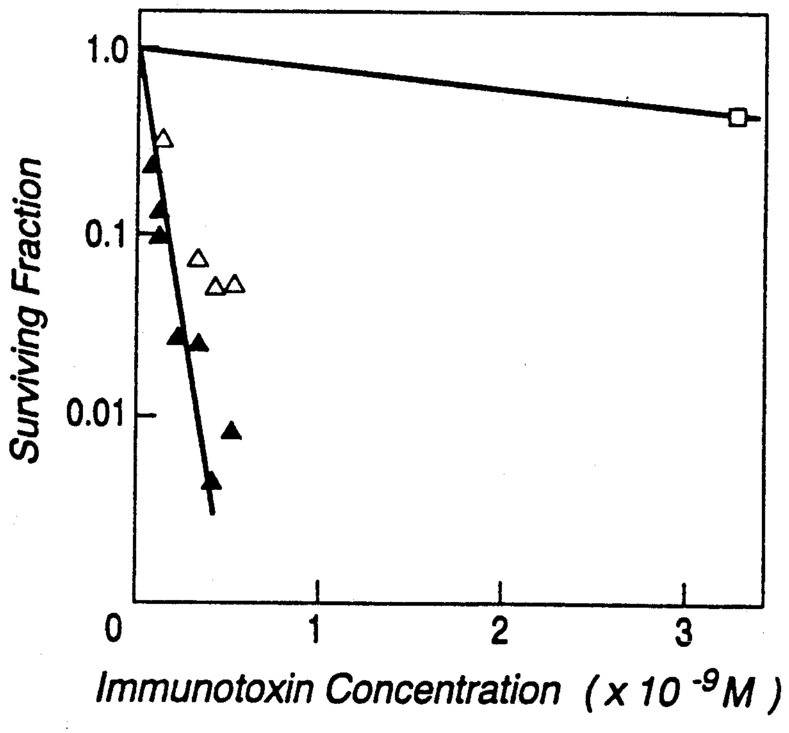
FIG. 15 shows the cytotoxicity of J5-blocked ricin for Namalwa cells after 24 hour exposure to conjugate. In the figure the closed triangles represent J5-blocked ricin; open triangles, J5-blocked ricin in the presence of 0.03M lactose; and open squares, J5-blocked ricin in the presence of 1 $\mu$M J5 antibody.

FIG. 15 shows the cytotoxicity of the J5-blocked ricin conjugate for Namalwa cells, which express CALLA to which J5 binds. When linked to J5. blocked ricin shows high toxicity for Namalwa cells, with an $IC_{50}$ value of about 0.05 nM. Unlike the toxicity exhibited by ricin the toxicity of the J5-blocked ricin conjugate was only slightly affected, if at all, by lactose. However, the cytotoxicity of J5-blocked ricin in the presence of J5 (1 μM) was greatly reduced, to levels comparable to those shown by blocked ricin alone, demonstrating that the enhanced toxicity of the conjugate was specific, mediated by the specific binding of the J5 antibody.

Figure 16:
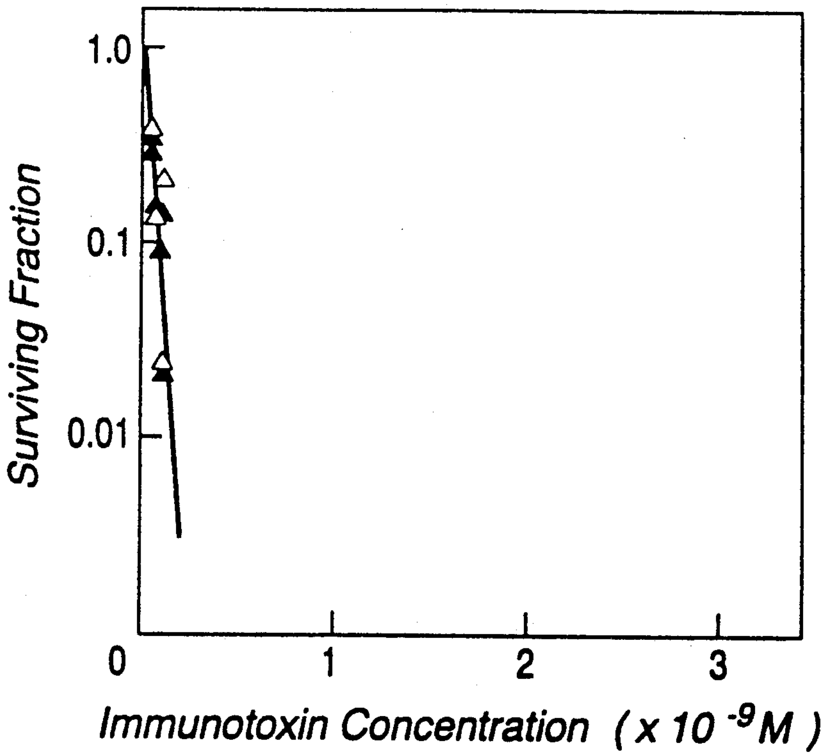
FIG. 16 shows the cytotoxicity of anti-B4-blocked ricin for Namalwa cells after 24 hour exposure to conjugate. In the figure: closed triangles, anti-B4-blocked ricin; and open triangles, anti-B4-blocked ricin in the presence of 0.03M lactose.

FIG. 16 shows the cytotoxicity of anti-B4-blocked ricin. The cytotoxicity of this conjugate for Namalwa cells which express the B4 antigen was high, with an $IC_{50}$ of about 0.03 nM, approaching the cytotoxicity of ricin. This toxicity was also not affected by co-incubation of cells with lactose together with the blocked ricin conjugate, as shown in FIG. 16, in contrast to the case for ricin alone as is shown in FIG. 14.

Figure 17:
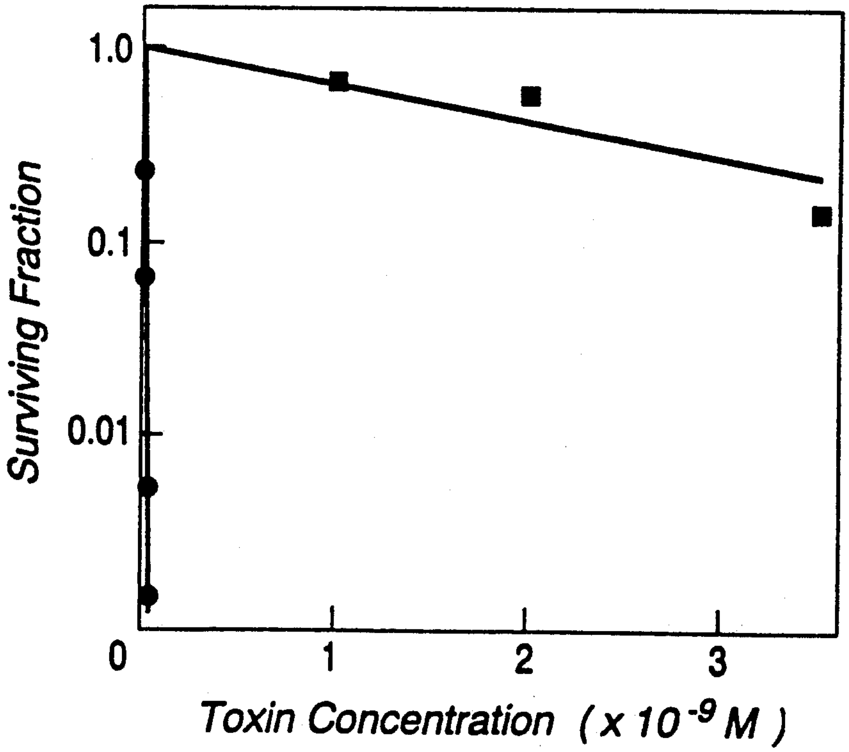
FIG. 17 shows the cytotoxicity of ricin and blocked ricin for Molt-4 cells after 24 hour exposure to toxins. In the figure: closed circles, ricin; and closed squares, blocked ricin.

FIG. 17 shows the toxicity of ricin and blocked ricin for Molt-4 cells (ATCC CRL 1582). As for Namalwa cells, ricin was very toxic for Molt-4 cells, with $IC_{50}$ values of less than 0.01 nM, while blocked ricin showed far less toxicity, with $IC_{50}$ values about 1.5 nM.

Figure 18:
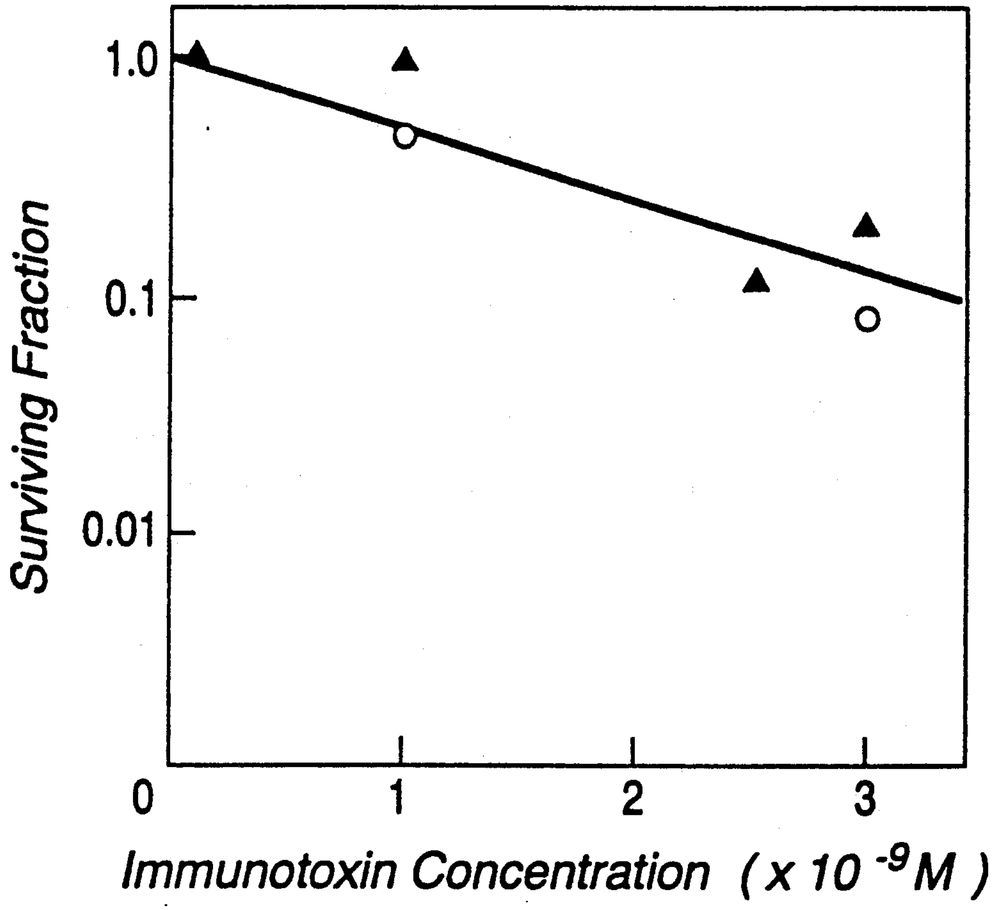
FIG. 18 shows the cytotoxicity of J5-blocked ricin (open circles) and anti-B4-blocked ricin (closed triangles) for Molt-4 cells, which do not express CALLA or B4.

FIG. 18 shows the cytotoxicity of J5-blocked ricin and anti-B4-blocked ricin for Molt-4 cells. Molt-4 cells do not express either relevant antigen (CALLA or B4), as was found in experiments similar to those reported in Goldmacher et al., *J. Imm.* 136, 320–325 (1986). The figure shows that the cytotoxicity of these conjugates for the Molt-4 cell line was about the same as that shown by the non-conjugated blocked ricin (compare FIG. 17 with FIG. 18). Thus, the enhanced toxicity of blocked ricin when the blocked ricin was linked to the antibodies J5 and anti-B4 was completely selective for the cell line expressing the particular antigens to which the antibody binds.

(e) Cytotoxocity of Conjugates With Blocked Abrin

Experiments with conjugates of monoclonal antibodies with blocked abrin demonstrated that such conjugates have similar properties to those containing blocked ricin. Conjugates of blocked abrin exhibited high toxicity that is specific for the antibody (excess non-conjugated antibody reduces toxicity) and selective for cell lines expressing the antigen specified by the antibody.

EXAMPLE 30

Specific Cytotoxicity of Anti-B4-Blocked Ricin (Anti-B4-bR) Toward Tumor-Derived Cell Lines In Vitro The cytotoxicity of anti-B4-bR toward two tumor-derived cell lines was tested in order to evaluate the specificity of the immunoconjugate.

The immunoconjugate used was anti-B4-bR, prepared according to Example 13, wherein the ligand was affinity ligand D. The immunoconjugate was purified by affinity chromatography, ion-exchange chromatography and gel filtration as described in Example 13.

Two well-known, publicly available cell lines were used, CD19-positive Namalwa cells, which is a Burkitt's lymphoma-derived line and CD19-negative Molt-4 cells.

The cells were cultured according to conventional methods in medium consisting of RPMI 1640 (GIBCO, Grand Island, N.Y.) supplemented with 10% (v/v) heat-inactivated (30 min. 56° C.) fetal calf serum (Flow Laboratories, McLean, Va.) and L-glutamine (2 mM) (sometimes. penicillin-G (50 U/mL) and streptomycin (50 μg/mL) were added) at 37° in a humidified atmosphere of 5% $CO_2$. Asynchronous exponentially growing cells were treated with the immunoconjugate at 37° C. for 24 hours, washed with warm (37° C.) medium, and placed in fresh warm medium for determination of the surviving fraction as described by Goldmacher et al., (*J. Imm.* 135, 3648 (1985)).

Briefly, after the treatments, cells were counted daily by using a Coulter counter. Cell concentration was adjusted to $3\times10^5$ cells/mL when necessary to maintain exponential growth.

The daily increase in the number of cells was used to calculate a relative cell number after correction for the dilution factor. An estimate of the number of proliferating cells was made by back-extrapolating the exponential growth curves of treated cultures to the end of the treatment period.

Figure 19B:
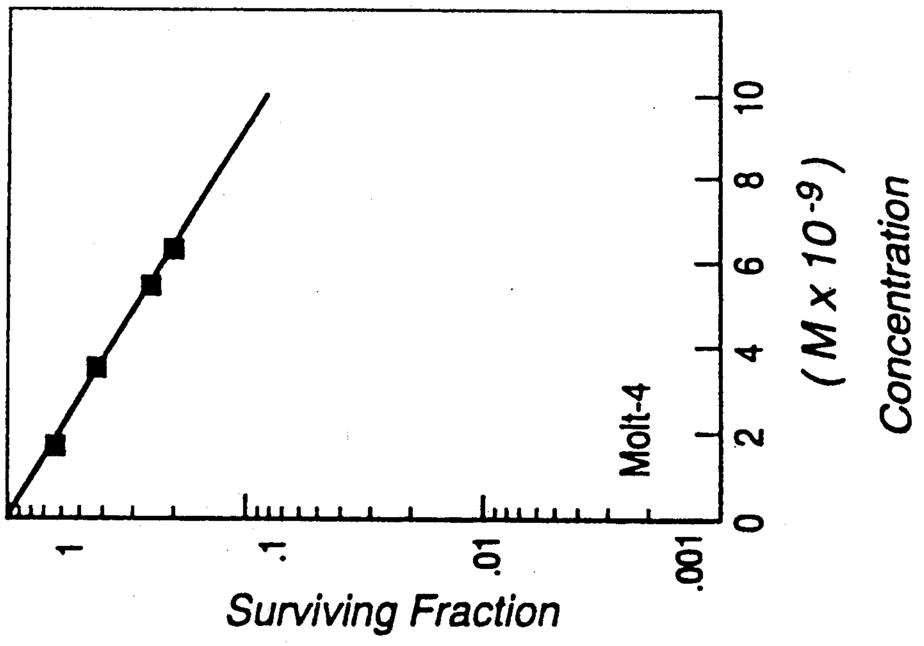
FIG. 19(A) and FIG. 19(B) are each graphs demonstrating the specific cytotoxicity of an immunoconjugate comprising anti-B4 monoclonal antibody and blocked ricin ("anti-B4-bR") for tumor-derived cell lines as measured by the in vitro cytotoxicity induced by the immunotoxin.
Figure 19A:
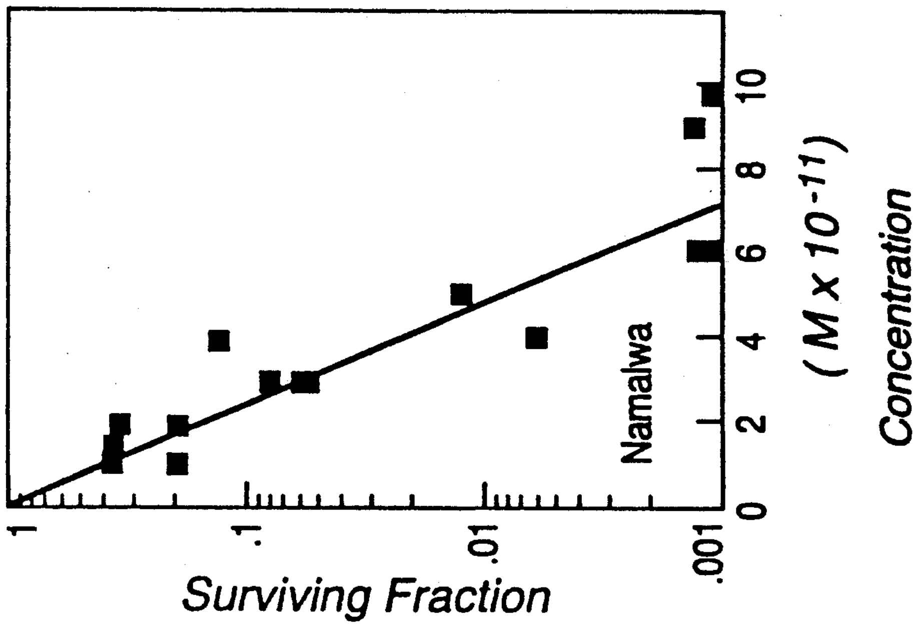

The results are shown in FIG. 19(A) and FIG. 9(B). The figures show that the CD19-positive Namalwa cells are at least 500-fold to 1000-fold more sensitive to the anti-B4-bR than are the CD19-negative Molt-4 cells. Accordingly, the anti-B4-bR is specific for CD19-positive cells.

EXAMPLE 31

Specific Cytotoxicity of Anti-B4-bR Toward Normal B Cells In Vitro and Comparison of Its Cytotoxicity to Normal T. Cells.

To determine the cytotoxicity of anti-B4-bR (prepared as described in Example 30) towards normal B cells vitro, the effect of anti-B4-bR on immunoglobulin (Ig) synthesis of Epstein-Barr virus (EBV)-activated peripheral blood lymphocytes (PBL) was measured.

Human PBL's were prepared according to conventional methods from heparinized blood of healthy donors by Ficoll-Paque gradient centrifugation using the manufacturer's protocol (Pharmacia, Piscataway, N.J.). The PBL's were activated with EBV by placing into culture $1\times10^5$ PBL in 0.2 mL of RPMI 1640 containing 10% fetal calf serum, L-glutamine (2 mM), penicillin (100 U/mL) and streptomycin (100 μg/mL) with a 1:10 dilution of supernatants from an EBV-producing cell culture. At culture initiation, the concentrations shown in FIG. 20(A) of anti B4-bR, anti-B4 or bR were added. Cultures were incubated for 8–10 days at 37° C. in a humidified atmosphere containing 5% $CO_2$.

In order to detect in vitro Ig synthesis. 96-well ELISA plates were precoated with unlabeled goat anti-mouse Ig (Southern Biotechnology Associates. Inc., Birmingham, Ala.). Supernatants from cultures were added to the wells and incubated overnight at 4° C. Wells were then aspirated, washed with borate-buffered saline (BBS) and filled with BBS containing 1% bovine serum albumin (BSA) to block non-specific binding. Wells were again aspirated, washed with BBS and filled with BBS containing horseradish peroxidase coupled goat anti-mouse Ig (IgG and IgM) from batches that were prescreened for low non-specific binding and for lack of reactivity with fetal calf serum and murine antibodies. After overnight incubation, wells were aspirated, washed with BBS and filled with BBS containing peroxidase substrate (ABTS. Boehringer Mannheim Biochemicals, Indianapolis. Ind.).

Immunoglobulin was quantified in each experiment by titration with Ig standards, namely purified human IgG from Southern Biotechnology Inc. The results are shown in FIG. 20(A).

Figure 20A:
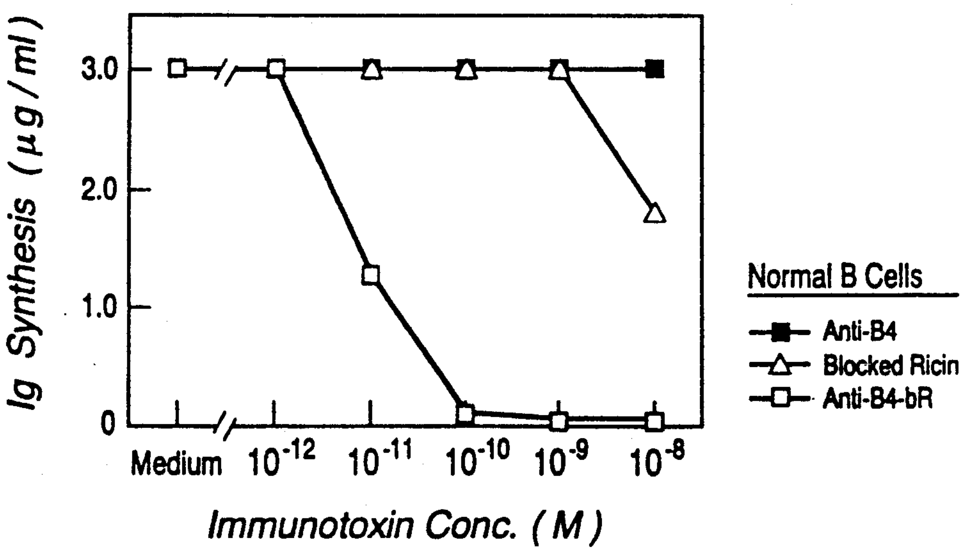
FIG. 20(A) and FIG. 20(B) are graphs showing the specific cytotoxicity of anti-B4-bR for normal B cells vitro and a comparison of anti-B4-bR cytotoxicity for normal T cells, respectively, as described in Example 31.

FIG. 20(A) shows that anti-B4-bR is very efficient in B cell killing as evidenced by total inhibition of Ig synthesis at concentrations higher than $10^{-11}$M. Anti-synthesis B4 antibody alone had no effect on Ig synthesis and free blocked ricin affects B cells only at thousand-fold higher concentrations.

The effect of anti-B4-bR on T cell proliferation was determined by exposing human PBL's, prepared as described above in this Example, to immunotoxin in the presence of 1 μg/mL of phytohemagglutinin (PHA). After culture for four days, the wells were pulsed with 1 μCi of [$^3$H]-thymidine for 18 hours and then the cells were harvested on glass fiber filters on a cell harvester and tritium incorporation was determined by scintillation counting. The results are shown in FIG. 20(B).

Figure 20B:
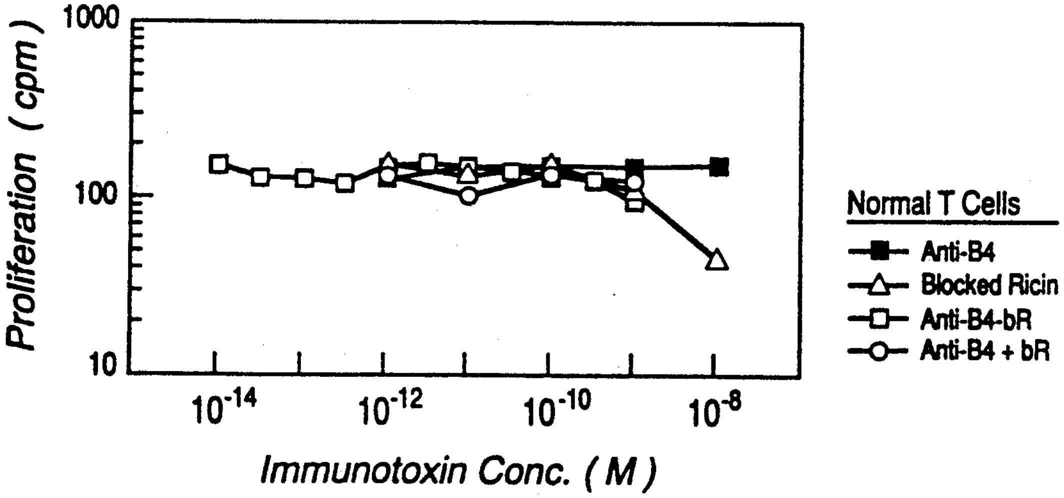
Figure 21A:
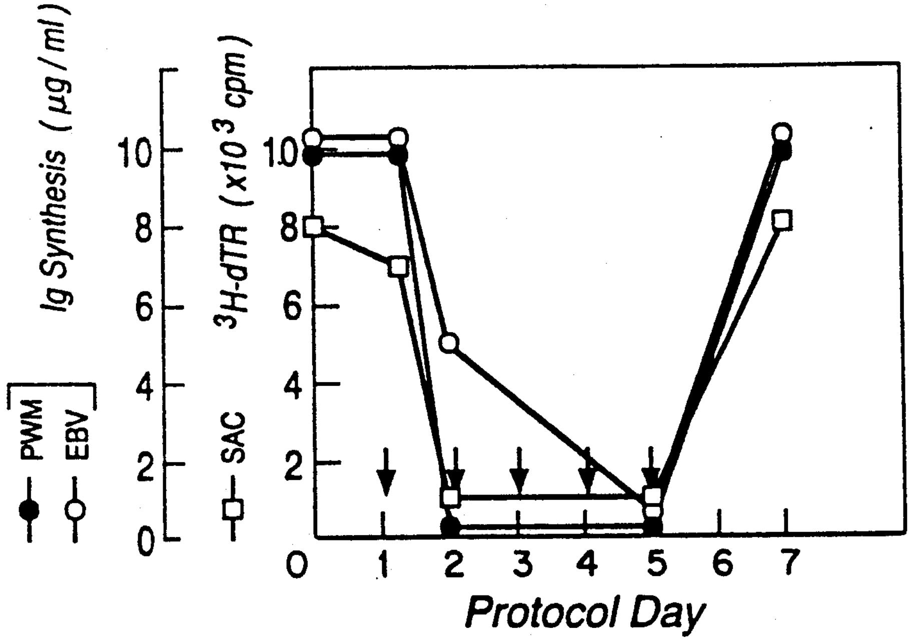
FIG. 21(A) shows B cell function in vitro from blood samples taken from patient A before, during and after treatment with anti-B4-bR. B cell function was determined either by quantitative immunoglobulin synthesis after activation by Epstein-Barr virus (EBV) or pokeweed mitogen (PWM) or by measuring thymidine ([$^3$H]-dTR) incorporation into DNA after activation with Staph. A Cowan particles (SAC).
Figure 21B:
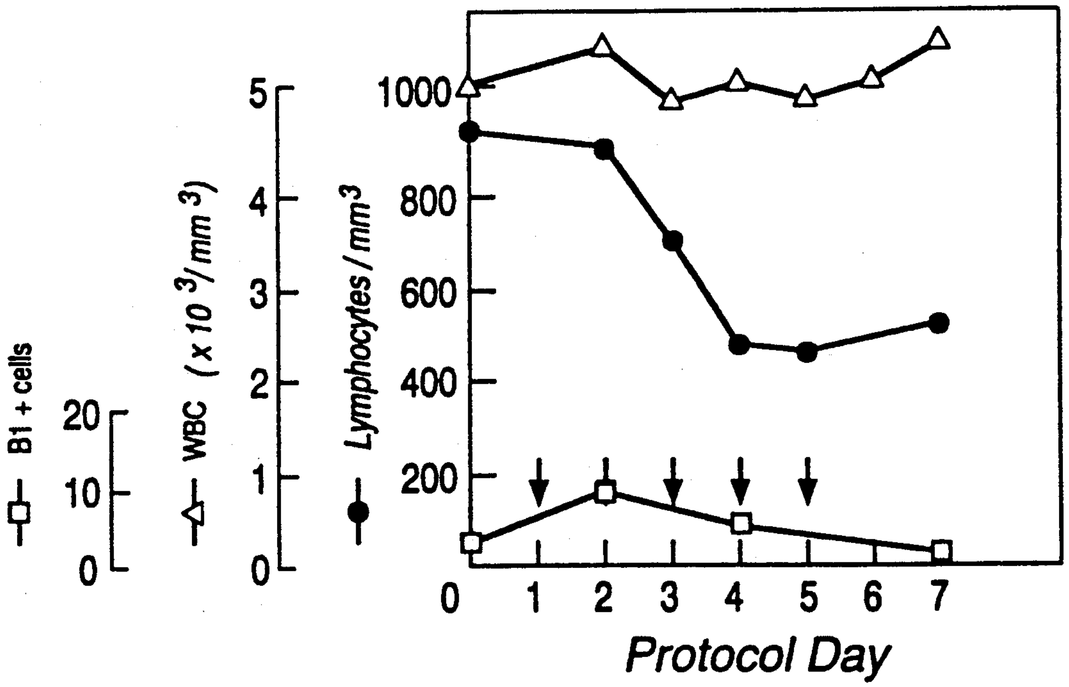
FIG. 21(B) shows lymphocyte counts, white blood cell counts (WBC) and B cell counts (B1-positive cells) in the blood of patient A during the course of treatment with anti-B4-bR.
Figure 21C:
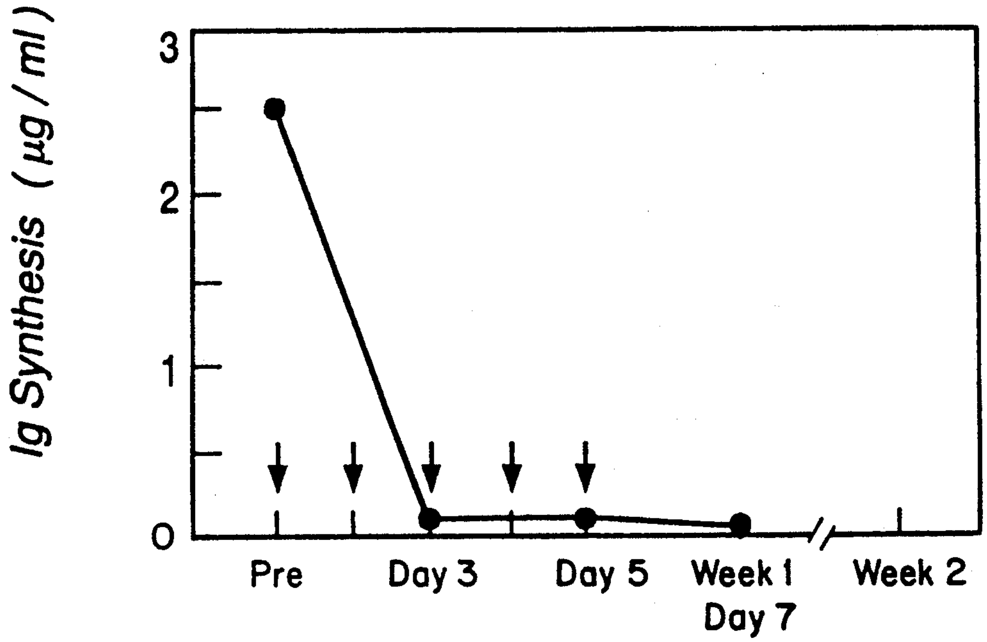
FIG. 21(C) and FIG. 21(D) show the in vivo effects of anti-B4-bR administration in patient B and patient C, respectively, as measured by assaying immunoglobulin synthesis in vitro with blood samples taken from patients B and C before, during and after treatment with anti-B4-bR. Immunoglobulin synthesis was assayed after activation with EBV. The ordinate represents immunoglobulin synthesized ($\mu$g/mL). The abscissa represents days.
Figure 21D:
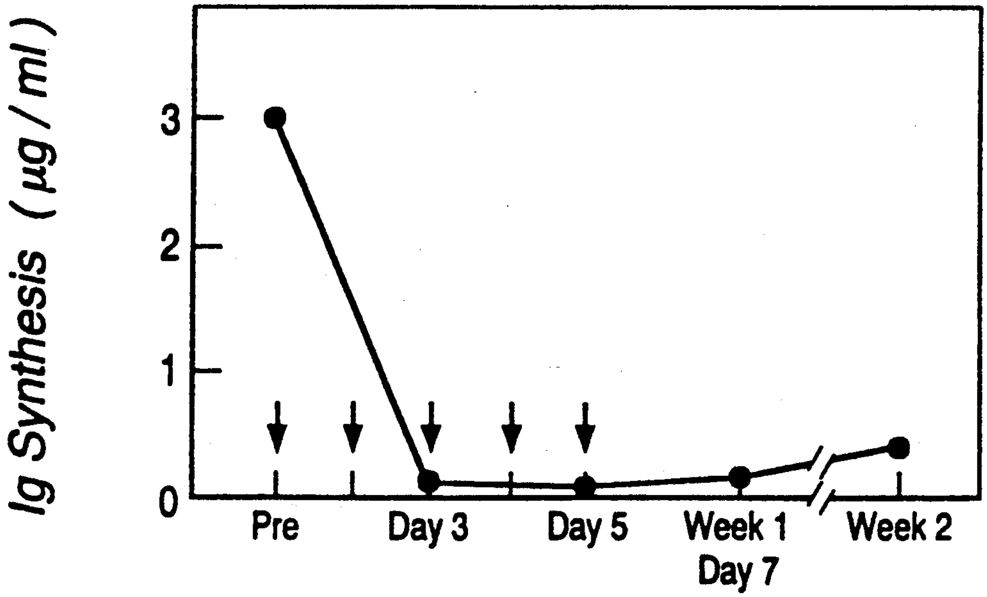

FIG. 20(B) shows that anti-B4-bR has no effect on T cell proliferation at concentrations of anti-B4-bR up to $10^{-9}$M. This demonstrates that the immunotoxin anti-B4-bR is specific for CD19-positive B cells.

EXAMPLE 32

In Vivo Effects of Anti-B4-bR

The in vivo effects of anti-B4-bR (prepared as described in Example 30) were determined as follows.

In a Phase I clinical trial conducted in accordance with US Food and Drug Administration regulations, patients with non-Hodgkin's lymphoma were given anti-B4-bR at various doses on five successive days. Blood samples received from the patients before, during, and after the treatment with the immunotoxin were tested for B cell function in vitro by either quantifying immunoglobulin synthesis after activation by EBV (see Example 31) or pokeweed mitogen (PWM) or by measuring tritiated thymidine ([$^3$H]-dTR) incorporation into DNA after activation with Staph A Cowan particles (SAC).

PBL's were prepared from heparinized blood by Ficoll-Paque gradient centrifugation (by the method described in Example 31) and $1\times10^5$ cells were aliquoted in 0.2 mL RPMI 1640 (Gibco) containing 10% fetal calf serum, L-glutamine (4mM), penicillin (10 U/mL) and streptomycin (100 μg/mL) into wells of a 96-well microtiter plate. Cells were then activated either with 0.02 mL of supernatant from an EBV-producing cell culture or with 0.002 mL from a 7.5% (w/v) stock solution of PWM (Gibco). Cultures were incubated at 37° C. for 8–10 days in a humidified atmosphere containing 5% $CO_2$ and immunoglobulin synthesis was analyzed by a quantitative ELISA as described in Example 31.

Activation with fixed SAC particles was done by adding 0.02 mL of a SAC suspension in PBS (SAC pellet was resuspended in 30–1000 times its volume). Cells were incubated at 37° C. in the presence of tritiated thymidine ([$^3$H]-TdR); 1 μCi/well) in a humidified atmosphere of 5% $CO_2$ and after 4–6 days, radioactivity incorporated into DNA was measured. The results are shown in FIGS. 20(A), 20(B), 20(C) and 20(D).

FIG. 20(A) shows that patient A received 1 μg/kg of anti-B4-bR on 5 successive days as indicated by the arrows in the figure. The figure shows that normal B cell function was transiently but completely obliterated during the course of the immunotoxin infusions. This decrease in immunoglobulin synthesis was not due to clearance of B cells from the circulation because immunoglobulin inhibition was maximal when significant numbers of B1-positive cells were still present as shown in FIG. 20(B).

FIG. 20(B) shows lymphocyte counts, white blood cell counts (WBC) and B cell counts (B1-positive cells) in the blood of patient A during the treatment course with anti-B4-bR. Inhibition of Ig synthesis was already complete on day 2. (FIG. 20(A)) but the B cell count on day 2 (B1-positive cells) was higher than on day 0 before treatment with anti-B4-bR. This indicates that the B cells present have lost their ability to proliferate and produce immunoglobulin and have not been simply cleared from circulation.

FIG. 20(C) and FIG. 20(D) show that patient B and patient C, respectively, received in their treatment regimen 5 μg/kg of anti-B4-bR on 5 successive days as indicated by the arrows. The figures show that normal B cell function was completely eliminated and was not restored even two weeks (patient C) after the start of the immunotoxin treatment. This set of experiments demonstrates with some confidence that B cells were killed in vivo.

EXAMPLE 33

Cytotoxicity of Anti-My9-Blocked Ricin Conjugate Against My9-Positive Cells

Normal human bone marrow mononuclear cells were obtained by conventional methods.

The bone marrow cells were cultured with various concentrations of anti-My9 antibody which was purified as described in Example 18, of anti-My9-blocked ricin (anti-My9-bR) which was prepared as described in Example 13 except using anti-My9 antibody in place of anti-B4 antibody, or of anti-B4-blocked ricin (anti-B4-bR) which was prepared as described in Example 13. The cells were cultured with the reagents for 24 hours.

The cells were then washed twice and assayed for residual CFU-GM and BFU-E cells using art-recognized methods such as those described in Sabbath et al., *J. Clin. Invest.* 75, 746–753 (1985) and in Griffin et al., *J. Imm.* 133, 1863–1868 (1984).

The results are summarized in Table 1 and Table 2.

TABLE 1

Results of CFU-GM colony assay after treatment of normal human bone marrow cells for 24 hours with anti-My9, anti-My9-bR or anti-B4-bR, respectively. Assays were performed as described in Sabbath et al. (J. Clin. Invest. 75, 746–753 (1985)).

| Treatment Method | Conc. (M) | CFU-GM colony counts (average of two parallel experiments) Day 7 | Day 14 |
|---|---|---|---|
| none | | 124 | ND* |
| none | | 120 | 38 |
| anti-My9 antibody | $10^{-9}$ | 108 | 30 |
| anti-My9-bR conjugate | $10^{-9}$ | 14 | 2 |
| | $10^{-10}$ | 73 | 20 |
| | $10^{-11}$ | 104 | 33 |
| anti-B4-bR conjugate | $10^{-9}$ | 96 | 36 |

*Not done.

TABLE 2

Results of CFU-GM, CFU-E & BFU-E colony assays after treatment of normal human bone marrow cells for 24 hours with anti-My9-bR or anti-B4-bR, respectively. Assays were performed as described in Sabbath et al. (J. Clin. Invest. 75, 746–753 (1985).

| Treatment Method | Conc (M) | Colony Counts (average of two parallel experiments) day 7 CFU-GM | day 7 CFU-E | day 14 CFU-GM | day 14 BFU-E |
|---|---|---|---|---|---|
| none | | 48 | 20 | 9 | 12 |
| anti-My9-bR | $2 \times 10^{-9}$ | 0 | 20 | 0 | 13 |
| | $1 \times 10^{-9}$ | 0 | 24 | 0 | 13 |
| | $5 \times 10^{-10}$ | 1 | 21 | 0 | n.d.* |
| | $1 \times 10^{-10}$ | 15 | 23 | 2 | n.d. |
| anti-B4-bR | $2 \times 10^{-9}$ | 46 | 21 | 7 | 14 |

*Not done.

The results show that at concentrations of $10^{-9}$M, anti-My9-blocked ricin conjugate is very effective in killing normal CFU-GM whereas the anti-B4-blocked ricin control had no such effect. The anti-My9 antibody by itself used at the same concentration, had no effect on colony cell growth. Note that CFU-GM were counted at two different time points, 7 days of culture and 14 days of culture. The colonies counted on day 14 were less numerous and are believed to be derived from a less "mature"hematopoietic cell.

With a second normal marrow the same protocol was followed. On this occasion there was complete loss of day 7 and day 14 CFU-GM at concentrations of $5 \times 10^{-10}M$ and higher of anti-My9-bR (Table 2). Erythroid progenitor cells (day 7 CFU-E and day 14 BFU-E) were not killed by this treatment.

Previous studies have shown that expression of the My9 antigen is variable from person to person on early stem cells of the erythroid series, and probably is expressed at very low density on some erythroid precursor cells from some individuals.

The same protocol was followed with AML cells of four patients except that before plating of the cells, the cells were treated at 37° C. for 24 hours with either, a) medium alone (served as the control); b) medium with $10^{-9}$M anti-My9-bR; c) medium containing $10^{-10}$M anti-My9-bR; or d) medium containing $10^{-9}$M anti-B4-bR. Also, two separately prepared anti-My9-bR conjugates were used. The anti-My9-bR conjugates were prepared as described in Example 13, except that anti-My9 was used in place of anti-B4.

Three of the four patients were known to express the My9 antigen and the fourth patient was not tested previously. After 24 hours of exposure to the immunoconjugate ($1 \times 10^{-9}$M anti-My9-blocked ricin), there was essentially complete killing of clonogenic AML cells in three of the four individuals (see FIG. 22). This included the one individual whose expression of My9 antigen had not previously been tested.

Anti-B4-blocked ricin at the same concentration was used as control and had no effect on colony formation.

Figure 22:
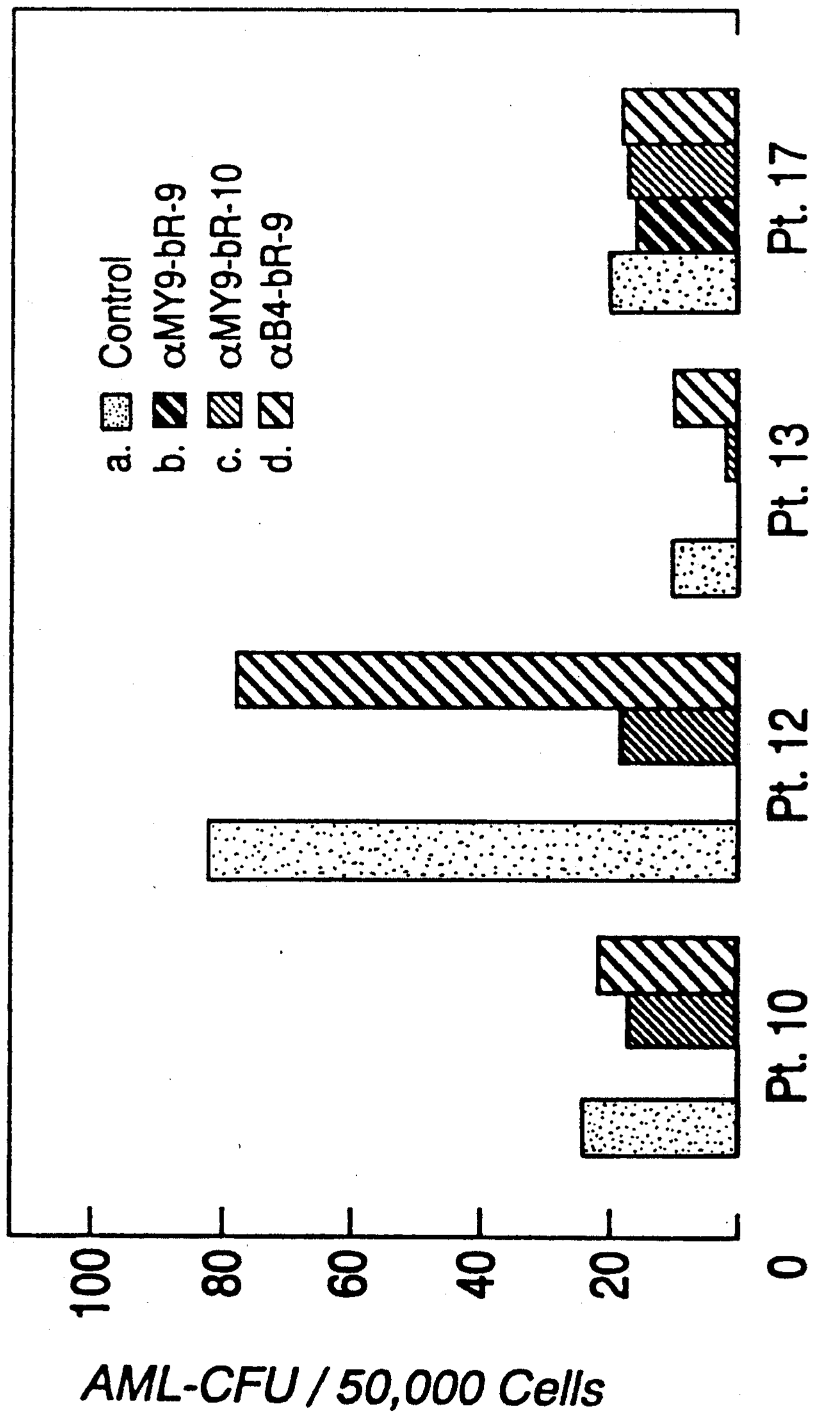
FIG. 22 depicts the results of L-CFU assays with cells from AML patients. The ordinate represents AML-colony forming units (AML-CFU) per 50,000 cells. The abscissa indicates the patient from which the AML cells were derived. In the figure a represents the control (medium alone); b represents medium containing $10^{-9}$M anti-My9-blocked ricin (anti-My9-bR); c represents medium containing $10^{-9}$M anti-My9-bR prepared separately from that used in b (another lot); and d represents medium that contains $10^{-9}$M anti-B4-blocked ricin (anti-B4-bR).

In FIG. 22, the ordinate represents AML-colony forming units (AML-CFU) per 50,000 cells. The abscissa indicates the patient from which the AML cells were derived. In the figure a represents the control (medium alone); b represents medium containing $10^{-9}$M anti-My9-bR; c represents medium containing $10^{-10}$M anti-My9-bR prepared separately from that used in b; and d represents medium containing $10^{-9}$M anti-B4-bR. These data show that anti-My9-bR is very efficient in killing the proliferative leukemia stem cells which maintain the leukemia in vivo.

It is believed that the elimination of these cells is necessary and sufficient to treat AML and CML in blast crisis. The destruction of healthy My9-positive cells at the same time is not a major concern, because they get replaced from the pluripotent stem cells, which are not affected by this treatment.

The effectiveness and specificity of anti-My9-bR for the killing of My9-positive cells was also demonstrated in vitro with tumor cell lines.

Asynchronous exponentially growing populations of cells were treated with the conjugate at 37° C. for 24 hours, washed, and placed into fresh medium for the determination of the surviving factions as described in detail by Goldmacher et al. (*J. Imm.* 135, 3648, (1985)).

Figure 23B:
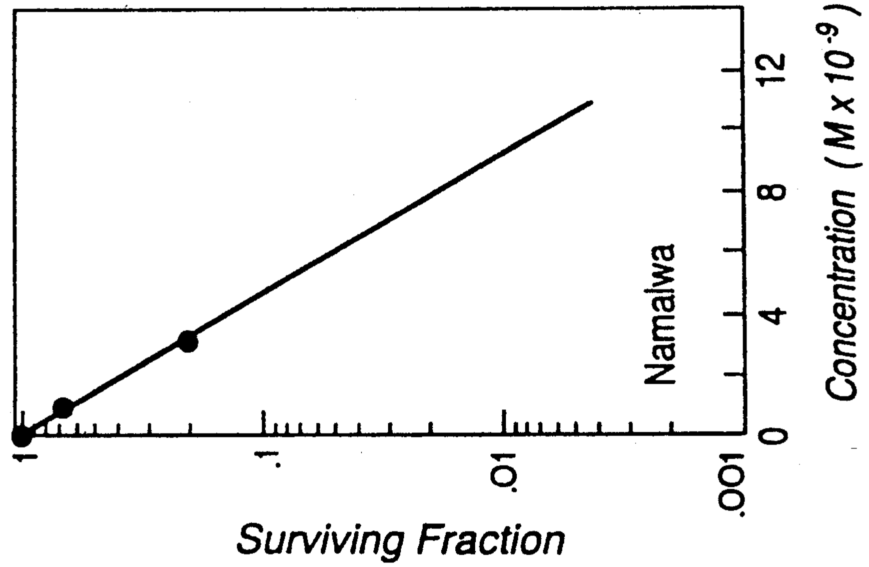
FIG. 23 comprises two graphs showing cytotoxicity induced by anti-My9-bR in My9-positive HL-60 cells (FIG. 23(A)) and in My9-negative Namalwa cells (FIG. 23(B)). In both figures, the ordinate represents the fraction of cells surviving after addition of anti-My9-bR and the abscissa represents the concentration of anti-My9-bR.
Figure 23A:
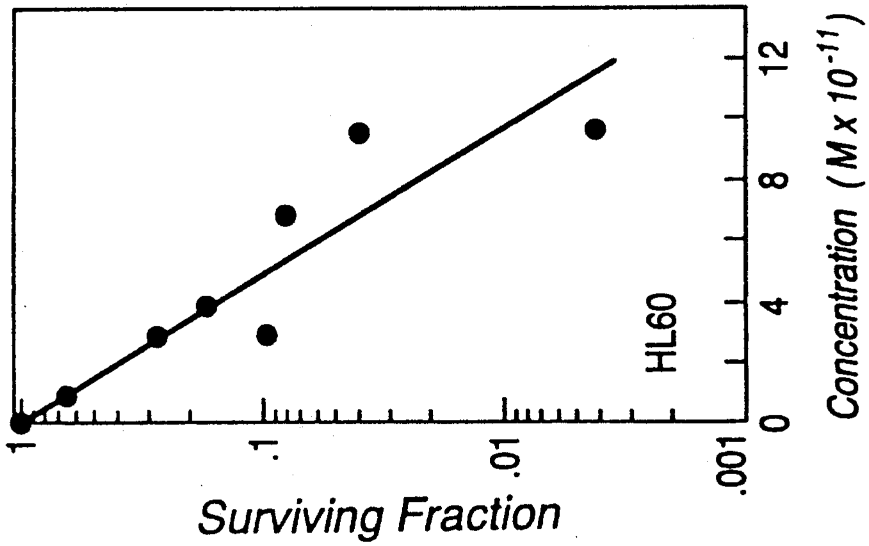

The results are shown in FIG. 23A for My9-positive HL-60 cells and FIG. 23B for My9-negative Namalwa cells. In both figures, the ordinate represents the fraction of cells surviving after the addition of anti-My9-bR and the abscissa represents the concentration of anti-Myg-bR.

FIGS. 23A and 23B show that cells of the My9-positive cell line HL-60 are killed very efficiently ($ID_{50} = 1.5 \times 10^{-11}$ after a 24 hour exposure to the conjugate) and that the My9-negative cells of the line Namalwa are resistant to anti-My9-bR and are killed only at much higher concentration ($ID_{50} = 2 \times 10^{-9}$M)

The most effective therapy for AML and CML in blast crisis is currently chemotherapy (Champlin & Gale. *Blood* 69, 1551 (1987) and De Vita et al., supra), which is severely limited by its toxic side effects and by the induction of drug resistance.

Anti-My9-blocked ricin is a targeted toxin and therefore less toxic side effects would be expected (in vitro. 2–3 logs of target specificity can be demonstrated, see FIG. 23). Drug resistance is caused either by amplification of the gene of the targeted protein or by expression of a multidrug transport protein in the cell membrane. Neither mechanism is applicable for anti-My9-bR. Also, in vitro, the present inventors could show five logs of cell kill without the generation of resistant cells.

EXAMPLE 34

In Vitro Cytotoxicity of Anti-N901-Blocked Ricin Immunoconjugate Against N901-Positive SCLC SW-2 Cells and N901-Negative Namalwa Cells Anti-N901 antibody, purified as described in Example 18, was conjugated with blocked ricin as described in Example 13 except using anti-N901 in place of anti-B4 antibody.

Asynchronous exponentially growing populations of cells were treated with the conjugate at 37° C. for 24 hours, washed and placed into fresh medium for the determination of the surviving factions as described in detail by Furth et al. (*Anal. Biochem.* 110, 1–8 (1981)).

Figure 24B:
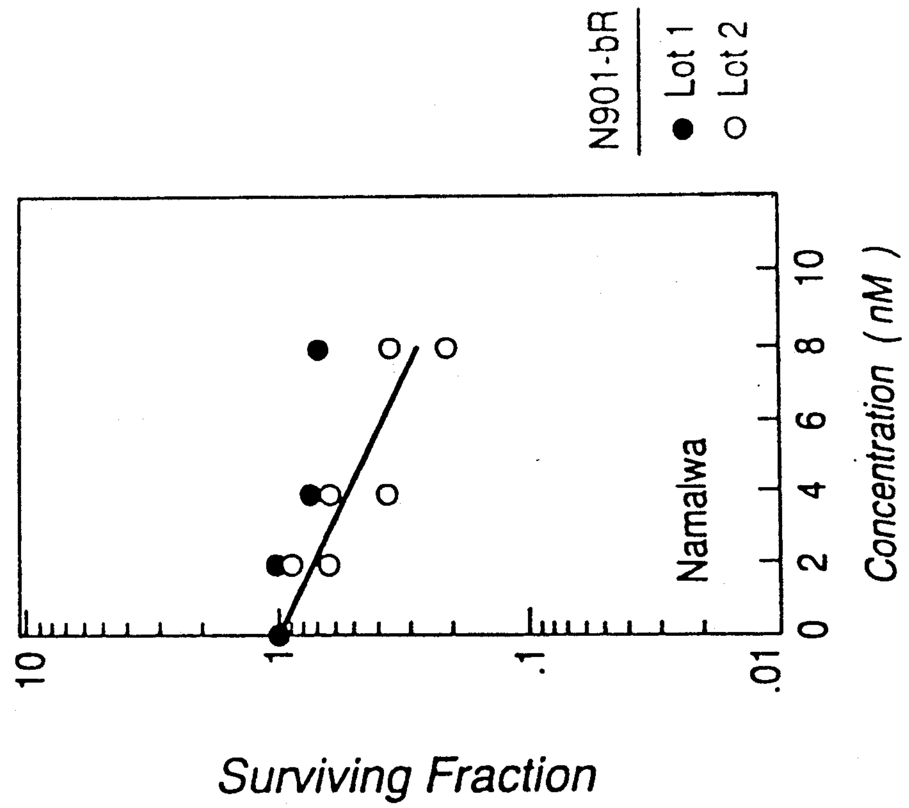
FIG. 24 depicts two graphs showing the effectiveness of anti-N901-blocked ricin immunoconjugate on N901-positive SW-2 cells (A) and on N901-negative Namalwa cells (B). On each graph the ordinate represents the fraction of cells surviving after exposure to the immunoconjugate and the abscissa represents the concentration of the immunoconjugate. For each cell type, two different lots of immunoconjugates were tested as represented in the figure by the open and filled circles.
Figure 24A:
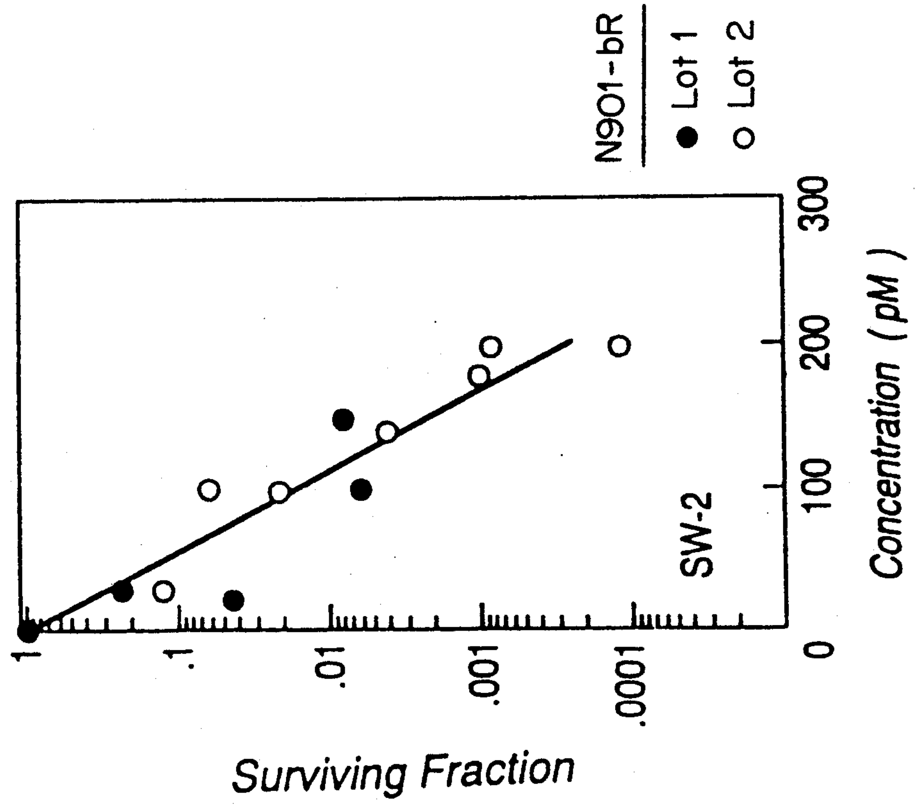

The results are shown in FIG. 24(A) for activity with N901-positive SW-2 cells and in FIG. 24(B) with N901-negative Namalwa cells. In both figures, the ordinate represents the fraction of cells surviving after addition of anti-N901-bR and the abscissa represents the concentration of anti-N901-bR.

FIG. 24 shows that cells of the N901-positive cell line SW-2 are killed efficiently ($IC_{37}=2.3\times10^{-11}M$ after a 24 hour exposure to the conjugate) and that cells of the N901-negative cells of the line Namalwa are resistant to N901-bR and are killed only at much higher concentrations of immunoconjugate ($IC_{37}=6\times10^{-9}M$).

While the invention has been described in detail and with reference to specific embodiments thereof, it will be apparent to one skilled in the art that various changes and modifications can be made therein without departing from the spirit and scope thereof.

What is claimed is:

1. A blocked lectin comprising one or more affinity ligands specifically bound to binding sites of a lectin covalently linked by means of a reactive group present on each of the ligands to said lectin such that one or more binding sites of said lectin is blocked, provided that said reactive group is not a photoactivatable group.

2. The blocked lectin of claim 1, wherein at least one of said covalently linked affinity ligands comprises a moiety capable of covalently linking said ligand to a cell-binding agent.

3. The blocked lectin of claim 1, wherein said lectin comprises a moiety capable of covalently linking said lectin to a cell-binding agent.

4. The blocked lectin of any one of claims 1, 2 or 3 wherein said affinity ligands comprise a sugar specific for a lectin.

5. The blocked lectin of any one of claims 1, 2 or 3, wherein said affinity ligands comprise a sugar specific for a cytotoxic lectin.

6. The blocked lectin of any one of claims 1, 2 or 3 wherein said affinity ligands comprise a sugar specific for ricin or abrin.

7. The blocked lectin of any one of claims 1, 2 or 3, wherein said affinity ligands comprise at least one terminal galactose derivative.

8. The blocked lectin of any one of claims 1, 2 or 3, wherein said reactive group that covalently links said ligands to said lectin is a protein cross-linking agent.

9. The blocked lectin of claim 8, wherein said protein cross-linking agent is a cyanuric chloride or a dichlorotriazine.

10. The blocked lectin of claim 2, wherein said moiety capable of linking said ligand to a cell-binding agent is:

$$X-S-S+CH_2+_n\overset{\overset{O}{\|}}{C}{}^{*} \text{ or } X-S-S+CH_2+_n\overset{\overset{+NH_2}{\|}}{C}{}^{*}$$

wherein X is alkyl or aryl, n is an integer of 1 or more and * denotes the group that is linked to the ligand.

11. The blocked lectin of any one of claims 1, 2 or 3, wherein said one or more affinity ligands is selected from the group consisting of an oligosaccharide derived from a glycoprotein and a glycopeptide derived from a glycoprotein.

12. The blocked lectin of any one of claims 1, 2, or 3, wherein said one or more affinity ligands is selected from the group consisting of an oligosaccharide derived from fetuin and a glycopeptide derived from fetuin.

13. The blocked lectin of any one of claims 1, 2 or 3, wherein said lectin is a cytotoxic lectin.

14. The blocked lectin of claim 13, wherein said cytotoxic lectin is one member selected from the group consisting of ricin, abrin, modeccin, volkensin, viscumin, Shigella toxin and derivatives thereof.

15. The blocked lectin of claim 14, wherein said cytotoxic lectin is ricin or abrin.

16. A cell-binding agent-blocked lectin conjugate comprising:

(1) a blocked lectin comprising one or more affinity ligands specifically bound to binding sites of a lectin covalently linked by means of a reactive group present on each of the ligands to said lectin such that one or more binding sites of said lectin is blocked , provided that said reactive group is not a photoactivatable group; and (2) a cell-binding agent covalently linked to:

(a) one of said covalently linked affinity ligands on the lectin via a moiety present on said affinity ligand capable of forming a covalent linkage to said cell-binding agent; or (b) said lectin via a moiety present on said lectin capable of forming a covalent linkage to a cell-binding agent.

17. The cell-binding agent-blocked lectin conjugate of claim 16, wherein said affinity ligands comprise a sugar specific for a lectin.

18. The cell-binding agent-blocked lectin conjugate of claim 16, wherein said affinity ligands comprise a sugar specific for a cytotoxic lectin.

19. The cell-binding agent-blocked lectin conjugate of claim 16, wherein said affinity ligands comprise a sugar specific for ricin or abrin.

20. The cell-binding agent-blocked lectin conjugate of claim 16, wherein said affinity ligands comprise at least one terminal galactose derivative.

21. The cell-binding agent-blocked lectin conjugate of claim 16, wherein said reactive group capable of covalently linking said ligand to said lectin is a protein cross-linking agent.

22. The cell-binding agent-blocked lectin conjugate of claim 21, wherein said protein cross-linking agent is cyanuric chloride, or a dichlorotriazine.

23. A method of preparing a blocked lectin comprising one or more affinity ligands specifically bound to binding sites of a lectin covalently linked by means of a reactive group present on each of the ligands to said lectin such that one or more binding sites of said lectin is blocked, said method comprising the steps of:

(1) binding at least a region of one or more activated affinity ligands having affinity for said binding sites of said lectin to said lectin; and (2) covalently linking with ligands to said lectin via a reactive group on said ligands to thereby block one or more of the binding sites of said lectin, provided that if said method is conducted with all reactants free in solution, said reactive group is not a photoactivatable group.

24. The method of claim 23, wherein said method is conducted with all reactants free in solution.

25. The method of claim 24, further comprising the steps of: '(3) recovering said blocked lectin from non-blocked lectin.

26. The method of claim 25, wherein said step (3) comprises an immunoaffinity step that uses a monoclonal antibody that distinguishes will blocked lectin from said non-blocked lectin.

27. The method of claim 23, wherein said blocked lectin is formed on a solid support via covalent linkage of said activated affinity ligand to said support, further comprising making an affinity support prior to said step (1) by:

(a) covalently linking said one or more affinity ligands to a solid support via a reactive group present on said affinity ligands; and (b) activating said affinity ligands to form a reactive group capable of covalently linking at least one of said one or more ligands to the lectin, provided that said covalent linking (a) and said activating (b) can be carried out in either order.

28. The method of claim 27, wherein said covalent linking (a) is carried out prior to said activating (b).

29. The method of claim 27, further comprising a step (3) of severing said covalent linkage between said one or more ligands and said solid support to release therefrom said blocked lectin.

30. The method of claim 29, further comprising a step of:

(4) recovering said blocked lectin from non-blocked lectin.

31. The method of claim 30, wherein said step (4) comprises an immunoaffinity step that uses a monoclonal antibody that distinguishes said blocked lectin from said non-blocked lectin.

32. The method of any one of claims 23, 24, 25, 26, 27, 28, 29, 30 or 31, wherein said affinity ligands comprise a sugar specific for a lectin.

33. The method of any one of claims 23, 24, 25, 26, 27, 28, 29, 30 or 31, wherein said affinity ligands comprise a sugar specific for a cytotoxic lectin.

34. The method of any one of claims 23, 24, 25, 26, 27, 28, 29, 30 or 31, wherein said affinity ligands comprise a sugar specific for ricin or abrin.

35. The method of any one of claims 23, 24, 25, 26, 27, 28, 29, 30 or 31, wherein said affinity ligands comprise at least one terminal galactose derivative.

36. The method of any one of claims 23, 24, 25, 26, 27, 28, 29, 30 or 31, wherein said reactive group that covalently links said ligands to said lectin is a protein cross-linking agent.

37. The method of any one of claims 24, 25 or 26, wherein said reactive group that covalently links said ligands to said lectin is cyanuric acid or a dichlorotriazine.

38. The method of any one of claims 23, 24, 25, 26, 27, 28, 29, 30 or 31, wherein said one or more affinity ligands is selected from the group consisting of an oligosaccharide derived from a glycoprotein and a glycopeptide derived from a glycoprotein.

39. The method of any one of claims 23, 24, 25, 26, 27, 28, 29, 30 or 31, wherein said one or more affinity ligands is selected from the group consisting of an oligosaccahride derived from fetuin and a glycopeptide derived from fetuin.

40. The method of any one of claims 23, 24, 25, 26, 27, 28, 29, 30 or 31, wherein said lectin is a cytotoxic lectin.

41. The method of claim 40, wherein said cytotoxic lectin is one member selected from the group consisting of ricin, abrin, modeccin, volkensin, viscumin, Shigella toxin and derivatives thereof.

42. The method of claim 41, wherein said cytotoxic lectin is ricin or abrin.

43. The method of claim 23, wherein said blocked lectin is formed on a solid support via covalent linkage of said activated affinity ligand to said support, further comprising making an affinity support prior to said step (1) by:

(a) covalently linking said one or more affinity ligands to a solid support via a reactive group present on said affinity ligands; and (b) activating said affinity ligands to form a reactive group capable of covalently linking at least one of said one or more ligands to the lectin, provided that said reactive group for covalently linking said affinity ligands to said lectin is not a photoactivatable group, and provided that said covalent linking (a) and said activating (b) can be carried out in either order.

44. The method of claim 43, wherein said covalent linking (a) is carried out prior to said activating (b).

45. The method of claim 43, further comprising the step of:

(3) severing said covalent linkage between said one or more ligands and said solid support to release therefrom said blocked lectin.

46. The method of claim 45, further comprising the step of:

(4) recovering said blocked lectin from non-blocked lectin.

47. The method claim 46, wherein said step (4) comprises an immunoaffinity step that uses a monoclonal antibody that distinguishes said blocked lectin from said non-blocked lectin.

48. The method of any one of claims 43, 44, 45, 46 or 47 wherein said affinity ligands comprise a sugar specific for a lectin.

49. The method of any one of claims 43, 44, 45, 46 or 47, wherein said affinity ligands comprise a sugar specific for a cytotoxic lectin.

50. The method of any one of claims 43, 44, 45 46 or 47, wherein said affinity ligands comprise a sugar specific for ricin or abrin.

51. The method of any one of claims 43, 44, 45, 46 or 47, wherein said affinity ligands comprise at least one terminal galactose derivative.

52. The method of any one of claims 43, 44, 45, 46 or 47, wherein said reactive group that covalently links said ligands to said lectin is a protein cross-linking agent.

53. The method of any one of claim 43, 44, 45, 46 or 47, wherein said lectin is a cytotoxic lectin.

54. The method of claim 53, wherein said cytotoxic lectin is one member selected from the group consisting of ricin, abrin, modeccin, volkensin, viscumin, Shigella toxin and derivatives thereof.

55. The method of claim 54, wherein said cytotoxic lectin is ricin or abrin.

56. A method of preparing a cell-binding agent-blocked lectin conjugate comprising:

(1) a blocked lectin comprising one or more affinity ligands specifically bound to binding sites of a lectin covalently linked by means of a reactive group present on each of the ligands to said lectin such that one or more binding sites of said lectin is blocked; and (2) a cell-binding agent covalently linked to:

(a) one of said covalently linked affinity ligands on the lectin via a moiety present on the affinity ligands capable of forming a covalent linkage to the cell-binding agent; or (b) to said lectin via a moiety present on the lectin capable of forming a covalent linkage to a cell-binding agent, said method comprising the steps of:

(1) binding at least a region of one or more activated affinity ligands having affinity for said binding sites of said lectin to said lectin;

(2) covalently linking said bound ligands to said lectin via a reactive group on said ligands to thereby block one or more of the binding sites of said lectin provided that if said steps (1) and (2) are conducted with all reactants free in solution, said reactive group is not a photoactivatable group; and (3) covalently linking a cell-binding agent to:

(a) one of said affinity ligands; or (b) said lectin.

57. The method of claim 56, wherein said steps (1) and (2) are conducted with all reactants free in solution.

58. The method of claim 57, further comprising the step (2) following said step (2) of:

(2a) recovering said blocked lectin from non-blocked lectin.

59. The method of claim 58, wherein said step (2a) comprises an immunoaffinity step that uses a monoclonal antibody that distinguishes said blocked lectin from said non-blocked lectin.

60. The method of claim 57, wherein said step (3) is conducted prior to said step (1) and comprises covalently linking said cell-binding agent to said lectin.

61. The method of claim 57, wherein said step (3) is conducted prior to said step (1) and comprises covalently linking said cell-binding agent to said affinity ligands.

62. The method of any one of claims 57, 58 or 59, wherein the affinity ligand comprises cyanuric chloride or a dichlorotriazine as the reactive group for forming a covalent linkage to the lectin and a pyridyldisulfide moiety for forming a covalent linkage to said cell-binding agent, to thereby form a cell-binding agent-blocked cytotoxic lectin conjugate wherein said cell-binding agent is covalently linked to the affinity ligand.

63. The method of claim 56, wherein said method further comprises making an affinity support prior to said step (1) by:

(a) covalently linking said one or more affinity ligands to a solid support via a reactive group present on said affinity ligands: and (b) activating said affinity ligands, provided that said covalent linking (a) and said activating (b) can be carried out in either order.

64. The method of claim 63, wherein said covalent linking (a) is carried out prior to said activating (b).

65. The method of claim 63, further comprising a step of:

(4) severing said covalent linkage between said one or more ligands and said solid support to release therefrom said cell-binding agent-blocked lectin conjugate.

66. The method of claim 63, further comprising the step (2a) following said step (2) of:

(2a) severing said covalent linkage between said one or more affinity ligands and said solid support to release therefrom said blocked lectin.

67. The method of claim 66, further comprising the step (2b) following said step (2a) of:

(2b) recovering said blocked lectin from said non-blocked lectin.

68. The method of claim 67, wherein said step (2b) comprises an immunoaffinity step that uses a monoclonal antibody that distinguishes said blocked lectin from said non-blocked lectin.

69. The method of claim 56, wherein said method further comprises making an affinity support prior to said step (1) by:

(a) covalently linking said one or more affinity ligands to a solid support via a reactive group present on said affinity ligands: and (b) activating said affinity ligands to form a reactive group capable of covalently linking at least one of said one or more ligands to the lectin, provided that said reactive group for covalently linking said ligands to said lectin is not a photoactivatable group and provided that said covalent linking (a) and said activating (b) can be carried out in either order.

70. The method of claim 69, wherein said covalent linking (a) is carried out prior to said activating (b).

71. The method of claim 69, further comprising a step of:

(4) severing said covalent linkage between one or more ligands and said solid support to release therefrom said cell-binding agent-blocked lectin conjugate.

72. The method of claim 69, further comprising the step (2a) following said step (2)of:

(2a) severing said covalent linkage between said at least one or more affinity ligands and said solid support to release therefrom said blocked lectin.

73. The method of claim 72 further comprising the step (2b) following said step (2a) of:

(2b) recovering said blocked lectin from said non-blocked lectin.

74. The method of claim 73, wherein said step (2b) comprises an immunoaffinity step that uses a monoclonal antibody that distinguishes said blocked lectin from said non-blocked lectin.

75. The method of any one of claims 56, 57, 60, 63, 65, 66, 69, 71 or 72, wherein said cell-binding agent comprises at least one binding site of a monoclonal antibody.

76. The method of claim 75, wherein said cell-binding agent comprises at least one CD1-binding site of an anti-CD1 antibody.

77. The method of claim 75 wherein said anti-CD19 antibody is anti-B4.

78. The method of claim 75, wherein said cell-binding agent comprises at least one CD33-binding site of an anti-CD33 antibody.

79. The method of claim 78, wherein said anti-CD33 antibody is anti-My9.

80. The method of claim 75, wherein said cell-binding agent comprises at least one CD56-binding site of an anti-CD56 antibody.

81. The method of claim 80 wherein said anti-CD56 antibody is anti-N901.

82. The method of any one of claims 56, 57, 60, 63, 65, 66, 69, 71 or 72, wherein said cell-binding agent is one member selected from the group consisting of hormones, lymphokines, growth factors and colony simulating factors.

83. The method of any one of claims 56, 57, 60 63, 65, 66, 69, 71 or 72, wherein said lectin is a cytotoxic lectin.

84. The method of claim 83, wherein said cytotoxic lectin is one member selected from the group consisting of ricin, abrin, modeccin, volkensin, viscumin, Shigella toxic and derivatives thereof.

85. The method of claim 84, wherein said cytotoxic lectin is ricin or abrin.

86. The cell-binding agent-blocked lectin conjugate of claim 16, wherein said moiety (2) (a) for forming a covalent linkage to said cell-binding agent is:

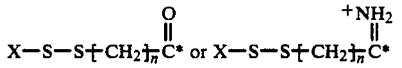

wherein X is alkyl or aryl, n is an integer of 1 or more and * denotes the group that is linked to the ligand.

87. The cell-binding agent-blocked lectin conjugate of claim 16, wherein said one or more affinity ligands is selected from the group consisting of an oligosaccharide derived from a glycoprotein and a glycopeptide derived from a glycoprotein.

88. The cell-binding agent-blocked lectin conjugate of claim 16, wherein said one or more affinity ligands is selected from the group consisting of an oligosaccharide derived from fetuin and a glycopeptide derived from fetuin.

89. The cell-binding agent-blocked lectin conjugate of claim 16, wherein said lectin is a cytotoxic lectin.

90. The cell-binding agent-blocked lectin conjugate of claim 89, wherein said cytotoxic lectin is one member selected from the group consisting of ricin, abrin, modeccin, volkensin, viscumin, Shigella toxin and derivatives thereof.

91. The cell-binding agent-blocked lectin conjugate of claim 90, wherein said cytotoxic lectin is ricin or abrin.

92. The cell-binding agent-blocked lectin conjugate of claim 16, wherein said cell-binding agent comprises at least one binding site of a monoclonal antibody.

93. The cell-binding agent-blocked lectin conjugate of claim 92, wherein said cell-binding agent comprises at least one CD19-binding site of an anti-CD19 antibody.

94. The cell-binding agent-blocked lectin conjugate of claim 93, wherein said anti-CD19 antibody is anti-B4.

95. The cell-binding agent-blocked lectin conjugate of claim 97, wherein said cell-binding agent comprises at least one CD33-binding site of an anti-CD33 antibody.

96. The cell-binding agent-blocked lectin conjugate of claim 95, wherein said anti-CD33 antibody is anti-My9.

97. The cell-binding agent-blocked lectin conjugate of claim 92, wherein said cell-binding agent comprises at least one CD56-binding site of an anti-CD56 antibody.

98. The cell-binding agent-blocked lectin conjugate of claim 97, wherein said anti-CD56 antibody is anti-N901.

99. The cell-binding agent-blocked lectin conjugate of claim 16, wherein said cell-binding agent is one member selected from the group consisting of hormones, lymphokines, growth factors and colony stimulating factors.

* * * * *

UNITED STATES PATENT AND TRADEMARK OFFICE
CERTIFICATE OF CORRECTION

PATENT NO. : 5,239,062

DATED : 24 August 1993

INVENTOR(S) : Walter A. BLATTLER et al.

It is certified that error appears in the above-identified patent and that said Letters Patent is hereby corrected as shown below:

Column 17, line 64, delete "$\nabla^{CH}2\_^{NH}\_^{CH}3$" and insert

— $\nabla CH_2$-NH-$CH_3$ —

Col. 23, line 68, delete "int" and insert -- into --.

Signed and Sealed this

Fifth Day of July, 1994

Attest:

BRUCE LEHMAN

Attesting Officer

Commissioner of Patents and Trademarks

UNITED STATES PATENT AND TRADEMARK OFFICE
Certificate

Patent No. 5,239,062 Patented: August 24, 1993

On petition requesting issuance of a certificate for correction of inventorship pursuant to 35 U. S. C. 256, it has been found that the above-identified patent, through error and without any deceptive intent, improperly sets forth the inventorship.

Accordingly, it is hereby certified that the correct inventorship of this patent is: Walter A. Blattler, John M. Lambert, Ravi V. J. Chari and Simon E. Moroney.

Signed and Sealed this Twenty-First Day of April, 1998.

STEPHEN WALSH
*Supervisory Patent Examiner*
Patent Examining Art Unit 1646

UNITED STATES PATENT AND TRADEMARK OFFICE
CERTIFICATE OF CORRECTION

PATENT NO. : 5,239,062

DATED : August 24, 1993

INVENTOR(S) : Walter A. Blattler, John M. Lambert, Ravi V.J. Chari and Simon E. Moroney It is certified that error appears in the above-indentified patent and that said Letters Patent is hereby corrected as shown below:

In Fig. 6 last line delete

"

Affinity Ligand D

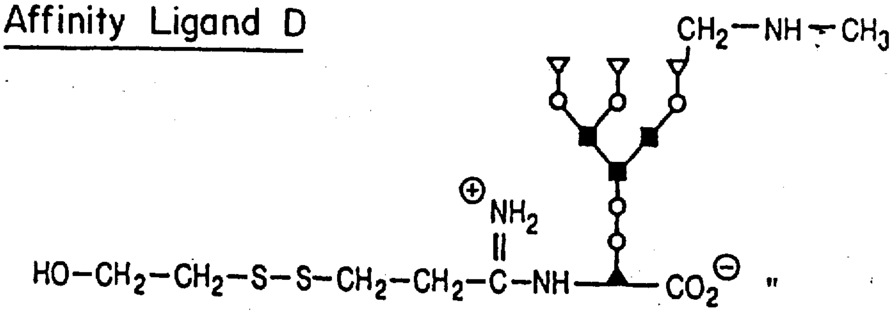

"

and insert therefore

UNITED STATES PATENT AND TRADEMARK OFFICE

CERTIFICATE OF CORRECTION

PATENT NO. : 5,239,062 Page 2 of 2

DATED : August 24, 1993

INVENTOR(S) : Walter A. Blattler, John M. Lambert, Ravi V.J. Chari and Simon E. Moroney It is certified that error appears in the above-indentified patent and that said Letters Patent is hereby corrected as shown below:

—

Affinity Ligand D

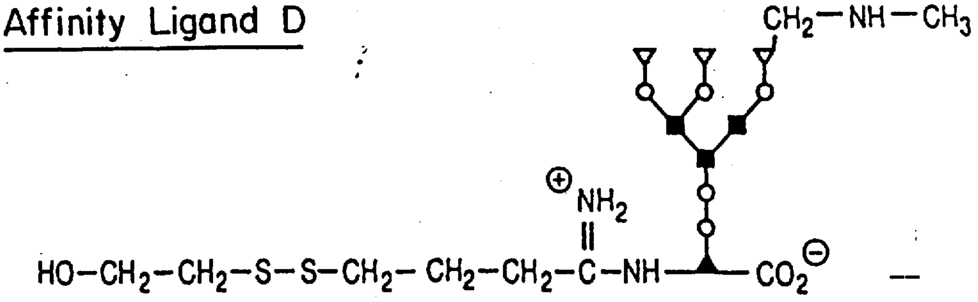

—

Signed and Sealed this

Twenty-seventh Day of October, 1998

Attest:

BRUCE LEHMAN

*Attesting Officer* *Commissioner of Patents and Trademarks*